US006600027B1

(12) United States Patent
Krishnan et al.

(10) Patent No.: US 6,600,027 B1
(45) Date of Patent: Jul. 29, 2003

(54) POLYNUCLEOTIDE MOLECULES ENCODING NEOSPORA PROTEINS

(75) Inventors: B. Rajendra Krishnan, East Lyme, CT (US); Rebecca Madura, Westerly, RI (US); Christine Yoder, Salem, CT (US); Becky Durtschi, Ledyard, CT (US); David A. Brake, East Lyme, CT (US)

(73) Assignees: Pfizer, Inc., New York, NY (US); Pfizer Products, Inc., Groton, CT (US)

( * ) Notice: Subject to any disclaimer, the term of this patent is extended or adjusted under 35 U.S.C. 154(b) by 0 days.

(21) Appl. No.: 09/276,438

(22) Filed: Mar. 25, 1999

Related U.S. Application Data

(60) Provisional application No. 60/112,282, filed on Dec. 15, 1998, and provisional application No. 60/079,389, filed on Mar. 26, 1998.

(51) Int. Cl.$^7$ ........................ C07H 21/02; C07H 21/04; C12P 21/06; C12N 1/20; C12N 15/00

(52) U.S. Cl. .................... 536/23.1; 536/23.4; 536/23.5; 536/24.32; 435/320.1; 435/252.3; 435/69.1

(58) Field of Search .............................. 536/23.1, 23.4, 536/23.5, 24.32; 435/320.1, 252.3, 69.1

(56) References Cited

U.S. PATENT DOCUMENTS

| | | | | |
|---|---|---|---|---|
| 5,643,718 A | | 7/1997 | Kim et al. | 435/6 |
| 5,707,617 A | | 1/1998 | Conrad et al. | 424/93.1 |
| 5,889,166 A | * | 3/1999 | Conrad et al. | |
| 5,942,394 A | * | 8/1999 | Ellis et al. | |
| 5,976,553 A | | 11/1999 | Kim et al. | 424/271.1 |
| 6,071,737 A | | 6/2000 | Marsh et al. | 435/258.1 |

FOREIGN PATENT DOCUMENTS

| | | |
|---|---|---|
| WO | 9525541 | 9/1995 |
| WO | 9717082 | 5/1997 |
| WO | 9739009 | 10/1997 |
| WO | 9742971 | 11/1997 |
| WO | 9808970 | 3/1998 |
| WO | 9853074 | 11/1998 |
| WO | 9920303 | 4/1999 |
| WO | 9961046 | 12/1999 |

OTHER PUBLICATIONS

Genbank, Accession No:A1579882.*

Genbank, Accession No: AW119278.*

Rudinger "Peptide Hormones" Edited by Parsons University Park Press, 1976.*

Hemphill et al Parasitology 115:581–90, Dec. 1997.*

Asbroek et al, 1990, Nature 348:174–175, "Targeted insertion of the neomycin phosphotransferase gene into the tubulin gene cluster of Trypanosoma brucei."

Barr et al., 1994, J. Vet. Diagn. Invest. 6:207–215, "Experimental reproduction of bovine fetal Neospora infection and death with a bovine Neospora isolate."

Cole et al., 1995, J. Parasitol. 81:730–732, "Vertical transmission of Neospora caninum in mice."

Conrad et al., 1993, Parasitol. 106:239–249, "In vitro isolation and characterization of a Neospora sp. from aborted bovine foetuses."

Cruz and Beverley, 1990, Nature 348:171–173, "Gene replacement in parasitic protozoa."

Donald and Roos, 1994, Mol. Biochem. Parasitol. 63:243–253, "Homologous recombination and gene replacement at the dihydrofolate reductase–thymidylate synthase locus in *Toxoplasma gondii*."

Dubey and Lindsay, 1993, Parasitol. Today 9:452–458 "Neosporosis."

Eid and Sollner–Webb, 1991, Proc. Natl. Acad. Sci. USA 88:2118–2121, "Stable integrative transformation of Trypanosoma brucei that occurs exclusively by homologous recombination."

Howe et al., 1997, Mol. Biochem. Parasitol. 86:29–36, "Expression of *Toxoplasma gondii* genes in the closely–related apicomplexan parasite *Neospora caninum.*"

Kim et al., 1993, Science 262:911–914, "Gene replacement in *Toxoplasma gondii* with chloramphenicol acetyltransferase as selectable marker."

Laban et al, 1990, Nature 343:572–574, "Stable Expression of the Bacterial neo$^r$ gene in *Leishmania enriettii.*"

LeBowitz et al., 1990, Proc. Natl. Acad. Sci. USA 87:9736–9740, "Development of a stable Leishmania expression vector and application to the study of parasite surface antigen genes."

Gwo–Shu et al., 1990, Science 250:1583–1586, "Homologous recombination and stable transformation in the parasitic protozoan Trypanosoma brucei."

Lindsay et al., 1995, J. Parasitol. 81:313–315, "Mouse model for central nervous system *Neospora caninum* infections."

Lindsay et al., 1995, Am. J. Vet. Res. 56:1176–1180, "Abortions, fetal deaths, and stillbirths in pregnant pygmy goats inoculated with tachyzoites of *Neospora caninum*."

Lindsay and Dubey, 1989, J. Parasitol. 75:772–779, "*Neospora caninum* (Protozoa: Apicomplexa) infections in mice."

(List continued on next page.)

*Primary Examiner*—Nita Minnifield

(74) *Attorney, Agent, or Firm*—Scully, Scott, Murphy & Presser

(57) ABSTRACT

The present invention provides isolated polynucleotide molecules comprising nucleotide sequences encoding GRA1, GRA2, SAG1, MIC1 and MAG1 proteins from *Neospora caninum*, as well as recombinant vectors, transformed host cells, and recombinantly-expressed proteins. The present invention further provides a polynucleotide molecule comprising the nucleotide sequence of the bidirectional GRA1IMAGI promoter of *N. caninum*. The present invention further provides genetic constructs based on the polynucleotide molecules of the present invention that are useful in preparing modified strains of Neospora cells for use in vaccines against neosporosis.

14 Claims, No Drawings

OTHER PUBLICATIONS

Lindsay and Dubey, 1989, J. Parasitol. 75:163–165, "In vitro development of *Neospora caninum* (Protozoa: Apicomplexa) from dogs."

Lindsay and Dubey, 1990, J. Parasitol. 76:410–413, "Infections in mice with tachyzoites and bradyzoites of *Neospora caninum* (Protozoa: Apicomplexa)."

Marsh et al., 1995, J. Parasitol. 81:530–535, "Sequence analysis and comparison of ribosomal DNA from bovine Neospora to similar coccidial parasites."

Messina et al., 1995, Gene 165:213–217, "Stable DNA transformation of *Toxoplasma gondii* using phleomycin selection."

Ryan et al, 1993, Proc. Natl. Acad. Sci. USA 90:8609–8613, "Isolation of virulence genes directing surface glycosyl–phosphatidylinositol synthesis by functional complementation of Leishmania."

Sibley et al., 1994, Proc. Natl. Acad. Sci. USA 91:5508–5512, "Stable DNA transformation in the obligate intracellular parasite *Toxoplasma gondii* by complementation of tryptophan auxotrophy."

Soldati and Boothroyd, 1993, Science 260:349–352, "Transient transfection and expression in the obligate intracellular parasite *Toxoplasma gondii*."

Titus et al., 1995, Proc. Natl. Acad. Sci. USA 92:10267–10271, "Development of a safe live Leishmania vaccine line by gene replacement."

Bülow R. et al., "Protection of Mice from Fatal *Toxoplasma gondii* Infection by Immunization with p30 Antigen in Liposomes", The Journal of Immunology 147(10):3496–3500 (1991) XP–002198881.

* cited by examiner

SEQUENCE LISTING

<160> NUMBER OF SEQ ID NOS: 34

<210> SEQ ID NO 1
<211> LENGTH: 1265
<212> TYPE: DNA
<213> ORGANISM: Neospora caninum
<220> FEATURE:
<221> NAME/KEY: CDS
<222> LOCATION: (205)..(777)

<400> SEQUENCE: 1

```
gtttcatcgt tgaactgccg aagagcttta tgttttgcc gcgacttctt tttctctccc      60
ctgaataaat tgtaccgtgg gtggcgtaca cgtctgaaca cgaactcggc tgggtttgct    120
tttgtggacg tgttttttccg gctcaaataa tttcattttc attgttcata cgtgtttgtg   180
atctctttta aggcattcag caag atg gtg cgt gtg agc gct att gtt ggg       231
                           Met Val Arg Val Ser Ala Ile Val Gly
                             1               5 gtt gca gcc tcg gtg gtt ctc tcc ctt tct tcc ggc gtg tac gcg gcc      279
Val Ala Ala Ser Val Val Leu Ser Leu Ser Ser Gly Val Tyr Ala Ala
 10              15                  20                  25 gag gga gcg gaa aaa ccc ttg gga ggc gaa ggt caa gcg cct acc ttg      327
Glu Gly Ala Glu Lys Pro Leu Gly Gly Glu Gly Gln Ala Pro Thr Leu
                 30                  35                  40 ttg tca atg cta ggt ggc ggg cgc gcg gga agg ggg ttg tca gtc gga      375
Leu Ser Met Leu Gly Gly Gly Arg Ala Gly Arg Gly Leu Ser Val Gly
             45                  50                  55 caa tca gta gac ctt gac ctg atg ggc aga cgc tac cga gtg acc aga      423
Gln Ser Val Asp Leu Asp Leu Met Gly Arg Arg Tyr Arg Val Thr Arg
         60                  65                  70 tcc gag ggt gcg cca gat gtg ctc gag atc tcc gtt ctg gac gcg gat      471
Ser Glu Gly Ala Pro Asp Val Leu Glu Ile Ser Val Leu Asp Ala Asp
     75                  80                  85 ggg aag gct tct cac atc ggc ttt gta agc att ccg gaa gtg atg gac      519
Gly Lys Ala Ser His Ile Gly Phe Val Ser Ile Pro Glu Val Met Asp
 90                  95                 100                 105 acc gtg gcg cgc atg cag aag gac gag gga att ttc ctt gat gcg tta      567
Thr Val Ala Arg Met Gln Lys Asp Glu Gly Ile Phe Leu Asp Ala Leu
                110                 115                 120 agt aaa gga gaa aca gta aag gag gcg atc gag gat gtt gct gca gcg      615
Ser Lys Gly Glu Thr Val Lys Glu Ala Ile Glu Asp Val Ala Ala Ala
            125                 130                 135 gaa ggt ctt tct ccc gag cag act gaa aac ctg gag gaa acg gtg gcc      663
Glu Gly Leu Ser Pro Glu Gln Thr Glu Asn Leu Glu Glu Thr Val Ala
        140                 145                 150 gct gta gcg act ctt gtt cgt gac gag atg gaa gtt ctt aaa gat cag      711
Ala Val Ala Thr Leu Val Arg Asp Glu Met Glu Val Leu Lys Asp Gln
    155                 160                 165 gag aag cta gaa gag gat gca gaa aag ctt gcg gga gat tta gaa gct      759
Glu Lys Leu Glu Glu Asp Ala Glu Lys Leu Ala Gly Asp Leu Glu Ala
170                 175                 180                 185 ctt caa ggg caa cat taa tttgcaaagg gattgtcatg tagccatatg              807
Leu Gln Gly Gln His
                190 ttcaatcgcc ctcaaaagtc gactggggtg ttttggcaca tgtctgcagt tggtttggat    867 cgacggcatg ggttagcgat ggagaaaacg gatcgatggt tgacagttgc cgaaggaaat    927 cggttgcgtc gtgtaaggaa agtgtcacgg gggcattgag atttggaggg gctccttgaag  987
```

-continued

| | |
|---|---|
| ccttcctcgg tggcaccaga ggggcagagc tcaacgcaag cgtggtatat ggagctggag | 1047 |
| cagtggccgc aacgcagcag ggcggcgtga attacgttgc gttagtgctg cgtgaaacg | 1107 |
| tcgtgttctc aacccgagta caatgtagtt tcaggtggtc gttgctcgaa tccgtgtgtc | 1167 |
| gcgcctgtgt tgtatagtgt ttcgcattat gtggagacgg ggacgttttt aaaaaatcaa | 1227 |
| aaatgtgtgg caaacctgaa aaaaaaaaa aaaaaaaa | 1265 |

<210> SEQ ID NO 2
<211> LENGTH: 190
<212> TYPE: PRT
<213> ORGANISM: Neospora caninum

<400> SEQUENCE: 2

```
Met Val Arg Val Ser Ala Ile Val Gly Val Ala Ala Ser Val Val Leu
 1               5                  10                  15
Ser Leu Ser Ser Gly Val Tyr Ala Ala Glu Gly Ala Glu Lys Pro Leu
            20                  25                  30
Gly Gly Glu Gly Gln Ala Pro Thr Leu Leu Ser Met Leu Gly Gly Gly
        35                  40                  45
Arg Ala Gly Arg Gly Leu Ser Val Gly Gln Ser Val Asp Leu Asp Leu
    50                  55                  60
Met Gly Arg Arg Tyr Arg Val Thr Arg Ser Glu Gly Ala Pro Asp Val
65                  70                  75                  80
Leu Glu Ile Ser Val Leu Asp Ala Asp Gly Lys Ala Ser His Ile Gly
                85                  90                  95
Phe Val Ser Ile Pro Glu Val Met Asp Thr Val Ala Arg Met Gln Lys
            100                 105                 110
Asp Glu Gly Ile Phe Leu Asp Ala Leu Ser Lys Gly Glu Thr Val Lys
        115                 120                 125
Glu Ala Ile Glu Asp Val Ala Ala Ala Glu Gly Leu Ser Pro Glu Gln
    130                 135                 140
Thr Glu Asn Leu Glu Glu Thr Val Ala Ala Val Ala Thr Leu Val Arg
145                 150                 155                 160
Asp Glu Met Glu Val Leu Lys Asp Gln Glu Lys Leu Glu Glu Asp Ala
                165                 170                 175
Glu Lys Leu Ala Gly Asp Leu Glu Ala Leu Gln Gly Gln His
            180                 185                 190
```

<210> SEQ ID NO 3
<211> LENGTH: 1774
<212> TYPE: DNA
<213> ORGANISM: Neospora caninum

<400> SEQUENCE: 3

| | |
|---|---|
| tgctagtact ggcgagtgaa atgcgacgct cactgtagcc tccagataca cgacctgttg | 60 |
| cggagctgac gctctcccca ctagagttca tgagcgatgg ggcgatggta gaccaacggt | 120 |
| ccctagcgct tcggctgttg cgcggcggct cttaagagcg ggacgaccgc ctttcaggtg | 180 |
| aaccgcctag tatcccaagc acacgaacat cccactcatg ggctggcgga actgctcgca | 240 |
| gcggttacgc aaaacacagtt gcgacgcaat gagccgtctc aagttgctgt cctcgtctca | 300 |
| tttcggatcg gttcccaggt cctccggtgc gtctctgtcg gaaggttatt gcaactccgt | 360 |
| tctgcgctgg gattagttta aatcatttca ttaatttgca gtttcatcgt tgaactgccg | 420 |
| aagagcttta tgtttttgcc gcgacttctt tttctctccc ctgaataaat tgtaccgtgg | 480 |
| gtggcgtaca cgtctgaaca cgaactcggc tgggtttgct tttgtggacg tgttttttccg | 540 |

-continued

```
gctcaaataa tttcattttc attgttcata cgtgtttgtg atctctttta aggcattcag    600
caagatggtg cgtgtgagcg ctattgttgg ggttgcagcc tcggtggttc tctcccttc     660
ttccggcgtg tacgcggccg agggagcgga aaaaccttg ggaggcgaag gtcaagcgcc     720
taccttgttg tcaatgctag gtggcgggcg cgcgggaagg gggttgtcag tcggacaatc    780
agtagacctt gacctgatgg gcagacgcta ccgagtgacc agatccgagg gtgcgccaga    840
tgtgctcgag atctcgtaag tagactactg gtgttcaacg aaaaaaagt acttgcgctg     900
tggaatgtcg tctgtgtgtt agctgcatca tgtgataagc aaacatttgt tttcgagcgt    960
gtgttgtctc gcgtgctttc agcgttctgg acgcggatgg gaaggcttct cacatcggct   1020
ttgtaagcat tccggaagtg atggacaccg tggcgcgcat gcagaaggac gagggaattt   1080
tccttgatgc gttaagtaaa ggagaaacag taaggaggc gatcgaggat gttgctgcag    1140
cggaaggtct ttctcccgag cagactgaaa acctggagga aacggtggcc gctgtagcga   1200
ctcttgttcg tgacgagatg gaagttctta aagatcagga gaagctagaa gaggatgcag   1260
aaaagcttgc gggagattta gaagctcttc aaggcaaca ttaatttgca aagggattgt    1320
catgtagcca tatgttcaat cgccctcaaa agtcgactgg ggtgttttgg cacatgtctg   1380
cagttggttt ggatcgacgg catgggttag cgatggagaa aacggatcga tggttgacag   1440
ttgccgaagg aaatcggttg cgtcgtgtaa ggaaagtgtc acggggcat tgagatttgg    1500
aggggctctt gaagccttcc tcggtggcac cagagggca gagctcaacg caagcgtggt   1560
atatggagct ggagcagtgg ccgcaacgca gcagggcggc gtgaattacg ttgcgttagt   1620
gctggcgtga acgtcgtgt tctcaacccg agtacaatgt agtttcaggt ggtcgttgct    1680
cgaatccgtg tgtcgcgcct tgttgtata gtgtttcgca ttatgtgtag acggggacgt   1740
ttttaaaaaa tcaaaaatgt gtggcaaacc tgaa                              1774
```

```
<210> SEQ ID NO 4
<211> LENGTH: 1031
<212> TYPE: DNA
<213> ORGANISM: Neospora caninum
<220> FEATURE:
<221> NAME/KEY: CDS
<222> LOCATION: (25)..(660)

<400> SEQUENCE: 4
```

```
aaatagggt ttcagcacca cacg atg ttc acg ggg aaa cgt tgg ata ctt          51
                             Met Phe Thr Gly Lys Arg Trp Ile Leu
                              1               5 gtt gtt gcc gtt ggc gcc ctg gtc ggc gcc tcg gta aag gca gcc gat         99
Val Val Ala Val Gly Ala Leu Val Gly Ala Ser Val Lys Ala Ala Asp
 10              15                  20                  25 ttt tct ggc agg gga acc gtc aat gga cag ccg gtt ggc agc ggt tat        147
Phe Ser Gly Arg Gly Thr Val Asn Gly Gln Pro Val Gly Ser Gly Tyr
                 30                  35                  40 tcc gga tat ccc cgt ggc gat gat gtt aga gaa tca atg gct gca ccc        195
Ser Gly Tyr Pro Arg Gly Asp Asp Val Arg Glu Ser Met Ala Ala Pro
             45                  50                  55 gaa gat ctg cca ggc gag agg caa ccg gag aca ccc acg gcg gaa gct        243
Glu Asp Leu Pro Gly Glu Arg Gln Pro Glu Thr Pro Thr Ala Glu Ala
         60                  65                  70 gta aaa cag gca gcg gca aaa gct tat cga tta ctc aag cag ttt act        291
Val Lys Gln Ala Ala Ala Lys Ala Tyr Arg Leu Leu Lys Gln Phe Thr
     75                  80                  85 gcg aag gtc gga cag gaa act gag aac gcc tac tac cac gtg aag aaa        339
```

```
Ala Lys Val Gly Gln Glu Thr Glu Asn Ala Tyr Tyr His Val Lys Lys
 90                  95                 100                 105 gcg aca atg aaa ggc ttt gac gtt gca aaa gac cag tcg tat aag ggc       387
Ala Thr Met Lys Gly Phe Asp Val Ala Lys Asp Gln Ser Tyr Lys Gly
            110                 115                 120 tac ttg gcc gtc agg aaa gcc aca gct aag ggc ctg cag agc gct ggc       435
Tyr Leu Ala Val Arg Lys Ala Thr Ala Lys Gly Leu Gln Ser Ala Gly
                125                 130                 135 aag agc ctt gag ctt aaa gag tcg gca ccg aca ggc act acg act gcg       483
Lys Ser Leu Glu Leu Lys Glu Ser Ala Pro Thr Gly Thr Thr Thr Ala
        140                 145                 150 gcg ccg act gaa aaa gtg ccc ccc agt ggc ccg cga tca ggt gaa gtt       531
Ala Pro Thr Glu Lys Val Pro Pro Ser Gly Pro Arg Ser Gly Glu Val
    155                 160                 165 cag cgt act cgt aaa gag caa aat gac gtg cag caa acc gca gag atg       579
Gln Arg Thr Arg Lys Glu Gln Asn Asp Val Gln Gln Thr Ala Glu Met
170                 175                 180                 185 ttg gct gag gaa att ctt gag gct ggg ctt aag aag gac gat gga gaa       627
Leu Ala Glu Glu Ile Leu Glu Ala Gly Leu Lys Lys Asp Asp Gly Glu
                190                 195                 200 gga cgg gga acg cca gaa gct gaa gtc aat taa gaaaatcact aaacgtcaag     680
Gly Arg Gly Thr Pro Glu Ala Glu Val Asn
            205                 210 ttctttatga ctgctgtaca ccaccacccc cctggactgc ttaagacagc taacaagcgt     740
tggatttcaa tatcctactt aaggtatgtg gggcggatgt cgtgtcacgg tgtgtatggc     800
gttaaaaaac ggcacacggc attaaatgca gtgcaagtat gaattgtgcg caggttgtgt     860
gtgacatttt tcggatgtcc tgggctttgt gtgcgtgcgt gggctgcgaa gagattagat     920
ttatttcttg cgattgcgat gcgtagtttg ttgcatcgtt atggtcatga aaaagtcta      980 acgacacaca taaacgatgg agcaaattaa aaaaaaaaa aaaaaaaaaa a              1031

<210> SEQ ID NO 5
<211> LENGTH: 211
<212> TYPE: PRT
<213> ORGANISM: Neospora caninum

<400> SEQUENCE: 5

Met Phe Thr Gly Lys Arg Trp Ile Leu Val Val Ala Val Gly Ala Leu
 1               5                  10                  15

Val Gly Ala Ser Val Lys Ala Ala Asp Phe Ser Gly Arg Gly Thr Val
                20                  25                  30

Asn Gly Gln Pro Val Gly Ser Gly Tyr Ser Gly Tyr Pro Arg Gly Asp
            35                  40                  45

Asp Val Arg Glu Ser Met Ala Ala Pro Glu Asp Leu Pro Gly Glu Arg
 50                  55                  60

Gln Pro Glu Thr Pro Thr Ala Glu Ala Val Lys Gln Ala Ala Ala Lys
 65                  70                  75                  80

Ala Tyr Arg Leu Leu Lys Gln Phe Thr Ala Lys Val Gly Gln Glu Thr
                85                  90                  95

Glu Asn Ala Tyr Tyr His Val Lys Lys Ala Thr Met Lys Gly Phe Asp
            100                 105                 110

Val Ala Lys Asp Gln Ser Tyr Lys Gly Tyr Leu Ala Val Arg Lys Ala
        115                 120                 125

Thr Ala Lys Gly Leu Gln Ser Ala Gly Lys Ser Leu Glu Leu Lys Glu
    130                 135                 140

Ser Ala Pro Thr Gly Thr Thr Thr Ala Ala Pro Thr Glu Lys Val Pro
```

|     |     |     |     |     |     |     |
| --- | --- | --- | --- | --- | --- | --- |
| 145 |     | 150 |     | 155 |     | 160 |

Pro Ser Gly Pro Arg Ser Gly Glu Val Gln Arg Thr Arg Lys Glu Gln
                165                 170                 175

Asn Asp Val Gln Gln Thr Ala Glu Met Leu Ala Glu Glu Ile Leu Glu
            180                 185                 190

Ala Gly Leu Lys Lys Asp Asp Gly Glu Gly Arg Gly Thr Pro Glu Ala
        195                 200                 205

Glu Val Asn
    210

<210> SEQ ID NO 6
<211> LENGTH: 1263
<212> TYPE: DNA
<213> ORGANISM: Neospora caninum
<220> FEATURE:
<221> NAME/KEY: CDS
<222> LOCATION: (130)..(1089)

<400> SEQUENCE: 6

```
tctgcgtgca gccttccgtt gttctcgctt gtatcacagg tgcctttgtc gtacataaac      60
attgtttcga ttgtagtcta gtcacaccgc actcgtttca tcactggcgc ttttgtttat     120 tcatcgaat atg ttt cct cgg gca gtg aga cgc gcc gtc tcg gtg ggt gtg     171
         Met Phe Pro Arg Ala Val Arg Arg Ala Val Ser Val Gly Val
           1               5                  10 ttc gcc gcg ccc gca ctg gtg gcg ttc ttt gac tgt gga act atg gca      219
Phe Ala Ala Pro Ala Leu Val Ala Phe Phe Asp Cys Gly Thr Met Ala
 15                  20                  25                  30 tca gaa aaa tca cct cta ctt gtc aat caa gtt gtc acc tgt gac aac      267
Ser Glu Lys Ser Pro Leu Leu Val Asn Gln Val Val Thr Cys Asp Asn
                 35                  40                  45 gaa gag aaa tca tca gtt gcc gtc cta cta tca ccg aag ctg aac cac      315
Glu Glu Lys Ser Ser Val Ala Val Leu Leu Ser Pro Lys Leu Asn His
             50                  55                  60 atc acg ctc aag tgc cct gac aat tcg acc gcc gtg ccc gct gct ctt      363
Ile Thr Leu Lys Cys Pro Asp Asn Ser Thr Ala Val Pro Ala Ala Leu
         65                  70                  75 ggt tat cca aca aac agg acc gtc tgc ccg gcg gag tcc gga ggt caa      411
Gly Tyr Pro Thr Asn Arg Thr Val Cys Pro Ala Glu Ser Gly Gly Gln
     80                  85                  90 act tgt aca ggc aag gag ata ccg ttg gaa agc ctg ctt ccc ggg gca      459
Thr Cys Thr Gly Lys Glu Ile Pro Leu Glu Ser Leu Leu Pro Gly Ala
 95                 100                 105                 110 aac gat agc tgg tgg tca ggt gtt gat atc aag act ggc gtt aag ctc      507
Asn Asp Ser Trp Trp Ser Gly Val Asp Ile Lys Thr Gly Val Lys Leu
                115                 120                 125 aca att cct gaa gcg agc ttc ccc aca aca tcc aag tcg ttc gac gtc      555
Thr Ile Pro Glu Ala Ser Phe Pro Thr Thr Ser Lys Ser Phe Asp Val
            130                 135                 140 ggc tgc gtc agc agt gat gcc agc aag agt tgt atg gtc aca gtc aca      603
Gly Cys Val Ser Ser Asp Ala Ser Lys Ser Cys Met Val Thr Val Thr
        145                 150                 155 gtg cca ccc aga gcc tca tcg ctt gtc aac ggt gtc gca atg tgc tct      651
Val Pro Pro Arg Ala Ser Ser Leu Val Asn Gly Val Ala Met Cys Ser
    160                 165                 170 tac ggt gca aac gaa act ctc ggc cct atc aca ttg tcc gag ggc gga      699
Tyr Gly Ala Asn Glu Thr Leu Gly Pro Ile Thr Leu Ser Glu Gly Gly
175                 180                 185                 190 tct tct acg atg acc ctc gtt tgc ggc acg gat ggg aag cca gtt cct      747
Ser Ser Thr Met Thr Leu Val Cys Gly Thr Asp Gly Lys Pro Val Pro
```

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 195 |     |     |     | 200 |     |     |     | 205 |     |     |     |      |
| cct | gat | cct | aag | cag | gtt | tgt | tct | ggg | acg | acc | gtc | aag | gat | tgt | aaa | 795  |
| Pro | Asp | Pro | Lys | Gln | Val | Cys | Ser | Gly | Thr | Thr | Val | Lys | Asp | Cys | Lys |      |
|     |     |     | 210 |     |     |     | 215 |     |     |     | 220 |     |     |     |     |      |
| gca | aaa | ccg | ttc | act | gat | gtt | ttc | cca | aaa | ttc | agt | gct | gat | tgg | tgg | 843  |
| Ala | Lys | Pro | Phe | Thr | Asp | Val | Phe | Pro | Lys | Phe | Ser | Ala | Asp | Trp | Trp |      |
|     |     | 225 |     |     |     | 230 |     |     |     | 235 |     |     |     |     |     |      |
| cag | gga | aaa | ccc | gac | act | aag | gat | ggt | gca | aaa | cta | acg | atc | aag | aaa | 891  |
| Gln | Gly | Lys | Pro | Asp | Thr | Lys | Asp | Gly | Ala | Lys | Leu | Thr | Ile | Lys | Lys |      |
|     | 240 |     |     |     | 245 |     |     |     | 250 |     |     |     |     |     |     |      |
| ggt | gca | ttt | cct | cca | aag | gag | gaa | aag | ttt | act | ctt | ggg | tgc | aag | agc | 939  |
| Gly | Ala | Phe | Pro | Pro | Lys | Glu | Glu | Lys | Phe | Thr | Leu | Gly | Cys | Lys | Ser |      |
| 255 |     |     |     | 260 |     |     |     | 265 |     |     |     | 270 |     |     |     |      |
| gta | tcg | agt | ccg | gag | gtt | tac | tgt | act | gtg | cag | gtg | gag | gca | gag | cgc | 987  |
| Val | Ser | Ser | Pro | Glu | Val | Tyr | Cys | Thr | Val | Gln | Val | Glu | Ala | Glu | Arg |      |
|     |     |     | 275 |     |     |     | 280 |     |     |     | 285 |     |     |     |     |      |
| gcg | agt | gca | ggg | atc | aag | tcg | tcg | gct | gaa | aat | gtt | ggt | cgc | gtt | tcc | 1035 |
| Ala | Ser | Ala | Gly | Ile | Lys | Ser | Ser | Ala | Glu | Asn | Val | Gly | Arg | Val | Ser |      |
|     |     | 290 |     |     |     | 295 |     |     |     | 300 |     |     |     |     |     |      |
| ctt | ttc | gct | gta | aca | att | gga | ctc | gta | ggc | tcg | ata | gcg | gct | ggc | gtc | 1083 |
| Leu | Phe | Ala | Val | Thr | Ile | Gly | Leu | Val | Gly | Ser | Ile | Ala | Ala | Gly | Val |      |
|     | 305 |     |     |     | 310 |     |     |     | 315 |     |     |     |     |     |     |      |

| gcg tga gtgacaatcg ttctgctcgc cattcataaa aataatgcaa gacatgttcg | 1139 |
|---|---|
| Ala | |
| 320 | |

| cgttcgtcat gtgtgtcttt atcataaaac aacatttact gattacttgt ggtggtttgc | 1199 |
|---|---|
| atatgtacaa tcccaaaaac tgctctactg taaagacgtt tagagtaaaa aaaaaaaaaa | 1259 |
| aaaa | 1263 |

<210> SEQ ID NO 7
<211> LENGTH: 319
<212> TYPE: PRT
<213> ORGANISM: Neospora caninum

<400> SEQUENCE: 7

Met Phe Pro Arg Ala Val Arg Arg Ala Val Ser Val Gly Val Phe Ala
 1               5                  10                  15

Ala Pro Ala Leu Val Ala Phe Phe Asp Cys Gly Thr Met Ala Ser Glu
            20                  25                  30

Lys Ser Pro Leu Leu Val Asn Gln Val Val Thr Cys Asp Asn Glu Glu
        35                  40                  45

Lys Ser Ser Val Ala Val Leu Leu Ser Pro Lys Leu Asn His Ile Thr
    50                  55                  60

Leu Lys Cys Pro Asp Asn Ser Thr Ala Val Pro Ala Ala Leu Gly Tyr
65                  70                  75                  80

Pro Thr Asn Arg Thr Val Cys Pro Ala Glu Ser Gly Gly Gln Thr Cys
                85                  90                  95

Thr Gly Lys Glu Ile Pro Leu Glu Ser Leu Pro Gly Ala Asn Asp
            100                 105                 110

Ser Trp Trp Ser Gly Val Asp Ile Lys Thr Gly Val Lys Leu Thr Ile
        115                 120                 125

Pro Glu Ala Ser Phe Pro Thr Ser Lys Ser Phe Asp Val Gly Cys
    130                 135                 140

Val Ser Ser Asp Ala Ser Lys Ser Cys Met Val Thr Val Thr Val Pro
145                 150                 155                 160

Pro Arg Ala Ser Ser Leu Val Asn Gly Val Ala Met Cys Ser Tyr Gly

-continued

```
                165                 170                 175

Ala Asn Glu Thr Leu Gly Pro Ile Thr Leu Ser Glu Gly Gly Ser Ser
            180                 185                 190

Thr Met Thr Leu Val Cys Gly Thr Asp Gly Lys Pro Val Pro Pro Asp
        195                 200                 205

Pro Lys Gln Val Cys Ser Gly Thr Thr Val Lys Asp Cys Lys Ala Lys
    210                 215                 220

Pro Phe Thr Asp Val Phe Pro Lys Phe Ser Ala Asp Trp Trp Gln Gly
225                 230                 235                 240

Lys Pro Asp Thr Lys Asp Gly Ala Lys Leu Thr Ile Lys Lys Gly Ala
                245                 250                 255

Phe Pro Pro Lys Glu Glu Lys Phe Thr Leu Gly Cys Lys Ser Val Ser
            260                 265                 270

Ser Pro Glu Val Tyr Cys Thr Val Gln Val Glu Ala Glu Arg Ala Ser
        275                 280                 285

Ala Gly Ile Lys Ser Ser Ala Glu Asn Val Gly Arg Val Ser Leu Phe
    290                 295                 300

Ala Val Thr Ile Gly Leu Val Gly Ser Ile Ala Ala Gly Val Ala
305                 310                 315

<210> SEQ ID NO 8
<211> LENGTH: 2069
<212> TYPE: DNA
<213> ORGANISM: Neospora caninum
<220> FEATURE:
<221> NAME/KEY: CDS
<222> LOCATION: (138)..(1520)

<400> SEQUENCE: 8
tcaatccttt cccgtgctaa cttgtaaaat cgctgctttc gttggttggt tttgtttcac      60
gtggctgtta agaggtcgac gcagctgttt aacccgtgcc cctggttctc caggtgatct     120
gcatcggatt tgcaaag atg ggc cag tcg gtg gtt ttc gtc atg ctt ttg        170
                   Met Gly Gln Ser Val Val Phe Val Met Leu Leu
                     1               5                  10 tcg gta ata ttt acc gct ggg gca aaa aca tac gga gaa gcg tcg caa       218
Ser Val Ile Phe Thr Ala Gly Ala Lys Thr Tyr Gly Glu Ala Ser Gln
            15                  20                  25 cca tcg gcc tca gca cgt tcg tta cag ggg gcc ctc gat aca tgg tgc       266
Pro Ser Ala Ser Ala Arg Ser Leu Gln Gly Ala Leu Asp Thr Trp Cys
        30                  35                  40 cag gag gtt ttt aaa aaa ctg tgc gat gac gga tat tca aaa atg tgt       314
Gln Glu Val Phe Lys Lys Leu Cys Asp Asp Gly Tyr Ser Lys Met Cys
     45                  50                  55 att cca gcc aac cag gta gtt gca cga caa ggc ctg ggt aga aaa gac       362
Ile Pro Ala Asn Gln Val Val Ala Arg Gln Gly Leu Gly Arg Lys Asp
 60                  65                  70                  75 caa caa aag ctc gta tgg cgg tgc tac gat tca gcg gcg ttt ctg gcc       410
Gln Gln Lys Leu Val Trp Arg Cys Tyr Asp Ser Ala Ala Phe Leu Ala
                 80                  85                  90 gaa ggc gac gaa aac aat gtc ctc agc tgc gtg gac gac tgt ggc gtt       458
Glu Gly Asp Glu Asn Asn Val Leu Ser Cys Val Asp Asp Cys Gly Val
            95                 100                 105 tcg ata ccg tgt cct ggc gga gtt gat agg gat aat agt acc cac gct       506
Ser Ile Pro Cys Pro Gly Gly Val Asp Arg Asp Asn Ser Thr His Ala
        110                 115                 120 acg cga cat gat gag ctt tcc caa tta atc aag gaa gga gta gtg cgc       554
Thr Arg His Asp Glu Leu Ser Gln Leu Ile Lys Glu Gly Val Val Arg
    125                 130                 135
```

```
tat tgc agt ggt ttc caa gcg gct gcc aac agc tac tgc aac aaa cga    602
Tyr Cys Ser Gly Phe Gln Ala Ala Ala Asn Ser Tyr Cys Asn Lys Arg
140                 145                 150                 155 tat cct ggg act gtt gcg agg aag tcg aag ggc ttc gga cac aag gaa    650
Tyr Pro Gly Thr Val Ala Arg Lys Ser Lys Gly Phe Gly His Lys Glu
                160                 165                 170 cca gtt aaa tgg aga tgt tac aag cca gag agc tta tta ttt tcg gtt    698
Pro Val Lys Trp Arg Cys Tyr Lys Pro Glu Ser Leu Leu Phe Ser Val
            175                 180                 185 ttt tct gag tgc gtg agt aac tgc gga aca acc tgg tcc tgc cct gga    746
Phe Ser Glu Cys Val Ser Asn Cys Gly Thr Thr Trp Ser Cys Pro Gly
        190                 195                 200 gga cga tta ggg aca gcg aca aat cta gac aaa aag cat ttc aca gat    794
Gly Arg Leu Gly Thr Ala Thr Asn Leu Asp Lys Lys His Phe Thr Asp
    205                 210                 215 gag tcc ggg att ctc cag gca ctc acc tct gtg ccg aaa gca tgt cca    842
Glu Ser Gly Ile Leu Gln Ala Leu Thr Ser Val Pro Lys Ala Cys Pro
220                 225                 230                 235 gta ggc ctt gtt tgc ctc ccg agg gat cag aat ccc ccg gcg tgt tta    890
Val Gly Leu Val Cys Leu Pro Arg Asp Gln Asn Pro Pro Ala Cys Leu
                240                 245                 250 gat gat aac ggc aac gtc cca gaa gag gag gga ggg cag ccc gta caa    938
Asp Asp Asn Gly Asn Val Pro Glu Glu Glu Gly Gly Gln Pro Val Gln
            255                 260                 265 ccg cgt gac acg aag ttg ccc gtt gat gat tcg gaa ccg acc gat gaa    986
Pro Arg Asp Thr Lys Leu Pro Val Asp Asp Ser Glu Pro Thr Asp Glu
        270                 275                 280 agt gaa act aca cct ggt gga ggt gat gat cag ccg agc cca aaa gag    1034
Ser Glu Thr Thr Pro Gly Gly Gly Asp Asp Gln Pro Ser Pro Lys Glu
    285                 290                 295 gac ggg gac aca gac tca cct gat gaa ggt gac cag tcc ggg ggt tca    1082
Asp Gly Asp Thr Asp Ser Pro Asp Glu Gly Asp Gln Ser Gly Gly Ser
300                 305                 310                 315 gag tgg tac aaa cag att ccg gaa atc cgt gtc atc ggt gac agc ctg    1130
Glu Trp Tyr Lys Gln Ile Pro Glu Ile Arg Val Ile Gly Asp Ser Leu
                320                 325                 330 caa gca atg ctc cac gct ggg cag cag ctg atg gtc acc tat agc tct    1178
Gln Ala Met Leu His Ala Gly Gln Gln Leu Met Val Thr Tyr Ser Ser
            335                 340                 345 ccc caa ctc cat gtt agt gtg gga tca tgt cac aaa ctc acg gtg aat    1226
Pro Gln Leu His Val Ser Val Gly Ser Cys His Lys Leu Thr Val Asn
        350                 355                 360 ttc tcc gat tat tat ttg tct ttt gac acc acc tca aag tcg ggg tcc    1274
Phe Ser Asp Tyr Tyr Leu Ser Phe Asp Thr Thr Ser Lys Ser Gly Ser
    365                 370                 375 gac gaa gtg gaa ctg gac gat gca gcg gga agc gga gag ctc acg ata    1322
Asp Glu Val Glu Leu Asp Asp Ala Ala Gly Ser Gly Glu Leu Thr Ile
380                 385                 390                 395 gga ctg gga agc agc ggc cgt gtg act gtt gtc ttc cag tat gcc aca    1370
Gly Leu Gly Ser Ser Gly Arg Val Thr Val Val Phe Gln Tyr Ala Thr
                400                 405                 410 aac ggt ggg gga aac aga tat gtt gct tac acc gtc gga gat tct gga    1418
Asn Gly Gly Gly Asn Arg Tyr Val Ala Tyr Thr Val Gly Asp Ser Gly
            415                 420                 425 tgc aaa aca att gaa gct gtt ctc ctt cac ggc ctg aat cct gga gcg    1466
Cys Lys Thr Ile Glu Ala Val Leu Leu His Gly Leu Asn Pro Gly Ala
        430                 435                 440 aag ctc gtt agg aat acg ata ggc gat aat tct ccg ggt gaa tct gaa    1514
Lys Leu Val Arg Asn Thr Ile Gly Asp Asn Ser Pro Gly Glu Ser Glu
```

```
                445             450             455
ttg taa cgactctttg tgttagtagt agccctccct atacagaatg ggagtgtatt   1570
Leu
460 acattttgtg atcaagggaa gaggagcgat cactacactt gatcacgcgt cgaggtcatt  1630 cgtgcgggc tgcagcttta tggtttgatc acgcaagaaa agaagcgcaa cacctgcaag   1690 tcgggcatgc gcgagggtcc catccttagt ttttttagt ttttttttg ccttcccgtc    1750 cgtccatatt tctcgggtct gtattttcta gcctgagatt ctagcctaga tccaatgcag  1810 tatgtcgcct gaagtcatgt taagtggtca gatgtttctg tctcagtgaa gaaaactgtg  1870 ttatggtgca ttctgtccga tttttatacgt aattcgtcgt acgttccatt gagttacgtg  1930 aggatgcgaa cgcagcaagt gatgtacgac aagttcgtag catggtgaca ctgtagaata  1990 caagtgtatt ttacagtcag gcggccggct actacacatt caagctgagt gacgtcgctt  2050 caaaaaaaaa aaaaaaaaa                                              2069

<210> SEQ ID NO 9
<211> LENGTH: 460
<212> TYPE: PRT
<213> ORGANISM: Neospora caninum

<400> SEQUENCE: 9

Met Gly Gln Ser Val Val Phe Val Met Leu Leu Ser Val Ile Phe Thr
  1               5                  10                  15

Ala Gly Ala Lys Thr Tyr Gly Glu Ala Ser Gln Pro Ser Ala Ser Ala
             20                  25                  30

Arg Ser Leu Gln Gly Ala Leu Asp Thr Trp Cys Gln Glu Val Phe Lys
         35                  40                  45

Lys Leu Cys Asp Asp Gly Tyr Ser Lys Met Cys Ile Pro Ala Asn Gln
     50                  55                  60

Val Val Ala Arg Gln Gly Leu Gly Arg Lys Asp Gln Lys Leu Val
 65                  70                  75                  80

Trp Arg Cys Tyr Asp Ser Ala Ala Phe Leu Ala Glu Gly Asp Glu Asn
                 85                  90                  95

Asn Val Leu Ser Cys Val Asp Asp Cys Gly Val Ser Ile Pro Cys Pro
            100                 105                 110

Gly Gly Val Asp Arg Asp Asn Ser Thr His Ala Thr Arg His Asp Glu
        115                 120                 125

Leu Ser Gln Leu Ile Lys Glu Gly Val Val Arg Tyr Cys Ser Gly Phe
    130                 135                 140

Gln Ala Ala Ala Asn Ser Tyr Cys Asn Lys Arg Tyr Pro Gly Thr Val
145                 150                 155                 160

Ala Arg Lys Ser Lys Gly Phe Gly His Lys Glu Pro Val Lys Trp Arg
                165                 170                 175

Cys Tyr Lys Pro Glu Ser Leu Leu Phe Ser Val Phe Ser Glu Cys Val
            180                 185                 190

Ser Asn Cys Gly Thr Thr Trp Ser Cys Pro Gly Gly Arg Leu Gly Thr
        195                 200                 205

Ala Thr Asn Leu Asp Lys Lys His Phe Thr Asp Glu Ser Gly Ile Leu
    210                 215                 220

Gln Ala Leu Thr Ser Val Pro Lys Ala Cys Pro Val Gly Leu Val Cys
225                 230                 235                 240

Leu Pro Arg Asp Gln Asn Pro Pro Ala Cys Leu Asp Asp Asn Gly Asn
                245                 250                 255
```

```
Val Pro Glu Glu Gly Gly Gln Pro Val Gln Pro Arg Asp Thr Lys
        260                 265                 270

Leu Pro Val Asp Asp Ser Glu Pro Thr Asp Glu Ser Glu Thr Thr Pro
        275                 280                 285

Gly Gly Gly Asp Asp Gln Pro Ser Pro Lys Glu Asp Gly Asp Thr Asp
        290                 295                 300

Ser Pro Asp Glu Gly Asp Gln Ser Gly Gly Ser Glu Trp Tyr Lys Gln
305                 310                 315                 320

Ile Pro Glu Ile Arg Val Ile Gly Asp Ser Leu Gln Ala Met Leu His
                325                 330                 335

Ala Gly Gln Gln Leu Met Val Thr Tyr Ser Ser Pro Gln Leu His Val
                340                 345                 350

Ser Val Gly Ser Cys His Lys Leu Thr Val Asn Phe Ser Asp Tyr Tyr
                355                 360                 365

Leu Ser Phe Asp Thr Thr Ser Lys Ser Gly Ser Asp Glu Val Glu Leu
        370                 375                 380

Asp Asp Ala Ala Gly Ser Gly Glu Leu Thr Ile Gly Leu Gly Ser Ser
385                 390                 395                 400

Gly Arg Val Thr Val Val Phe Gln Tyr Ala Thr Asn Gly Gly Gly Asn
                405                 410                 415

Arg Tyr Val Ala Tyr Thr Val Gly Asp Ser Gly Cys Lys Thr Ile Glu
                420                 425                 430

Ala Val Leu Leu His Gly Leu Asn Pro Gly Ala Lys Leu Val Arg Asn
                435                 440                 445

Thr Ile Gly Asp Asn Ser Pro Gly Glu Ser Glu Leu
        450                 455                 460

<210> SEQ ID NO 10
<211> LENGTH: 2278
<212> TYPE: DNA
<213> ORGANISM: Neospora caninum

<400> SEQUENCE: 10
atgggccagt cggtggtttt cgtcatgctt ttgtcggtaa tatttaccgc tggggcaaaa      60
acatacggag aaggtaagtc tccagctggt ttgtttgctt tgcaacaccc cccacctgga     120
gcgtctcgca actgtagatt gaagaaacta gtggacccgg ttgctggttc ttcaggtacc     180
gtagtacatt cattggcaac agtgtagtcc ttttcgcata gtagcaaggc gtcgaactgt     240
ttttagtccg gatacaatcg gacgttctgc attgcgtgcg aactgctgtg aggacacctt     300
ctgatgcacg gaactgattt tctggatttg tcgggtgttt gcagcgtcgc aaccatcggc     360
ctcagcacgt tcgttacagg gggccctcga tacatggtgc caggaggttt ttaaaaaact     420
gtgcgatgac ggatattcaa aaatgtgtat tccagccaac caggtagttg cacgacaagg     480
cctgggtaga aaagaccaac aaaagctcgt atggcggtgc tacgattcag cggcgtttct     540
ggccgaaggc gacgaaaaca atgtcctcag ctgcgtggac gactgtggcg tttcgatacc     600
gtgtcctggc ggagttgata gggataatag tacccacgct acgcgacatg atgagctttc     660
ccaattaatc aaggaaggag tagtgcgcta ttgcagtggt ttccaagcgg ctgccaacag     720
ctactgcaac aaacgatatc ctgggactgt tgcgaggaag tcgaagggct tcggacacaa     780
ggaaccagtt aaatggagat gttacaagcc agtaaggagg agctggctag attgcattag     840
tctgccctca ccacatcgtc agcgatcgct tcttgtgggg gataggagac atgatcctgg     900
gtcgcggaag agatgagcct ggtcctcgtc cgtgttagtg gcagcaaatt aaccccacgg     960
```

-continued

```
aggtggcagg gattatttag catagcgtat gtacgttttc ggtggagggc aggagcacga   1020
gataactgta gagatccacg gcctctgtgc ctttccagtt atgttcacac agttttacac   1080
tagctgatag cattcacata cgttttacga agttcccgac aaacaccaag aggaaagtgg   1140
gggaaatgtt agatttgagg tgcgtactgt tgttgatgtg ttttaggaga gcttattatt   1200
ttcggttttt tctgagtgcg tgagtaactg cggaacaacc tggtcctgcc ctggaggacg   1260
attaggtgag tttaagattc aggaatagca gaaatagtgc cacgaggtgc agcttcagcc   1320
tgtaacgctg cttcttcatc actcgtatcc tggacacccc gagaaaggca tcggattgtt   1380
tttcaggatt taccaaacaa acaatgatgc gagtcgagca gttattctgg gattttttt   1440 ctagaatgtg taagccagtt tcaatcgttg gctcatccgg catctttttc ctgttggcgc   1500
tcggttactt gcagggacag cgacaaatct agacaaaaag catttcacag atgagtccgg   1560
gattctccag gcactcacct ctgtgccgaa agcatgtcca gtaggccttg tttgcctccc   1620
gagggatcag aatccccggg cgtgtttaga tgataacggc aacgtccag aagaggaggg    1680 agggcagccc gtacaaccgc gtgacacgaa gttgcccgtt gatgattcgg aaccgaccga   1740
tgaaagtgaa actacacctg gtggaggtga tgatcagccg agcccaaaag aggacgggga   1800
cacagactca cctgatgaag gtgaccagtc cggggttca gagtggtaca aacagattcc    1860
ggaaatccgt gtcatcggtg acagcctgca agcaatgctc cacgctgggc agcagctgat   1920
ggtcacctat agctctcccc aactccatgt tagtgtggga tcatgtcaca aactcacagt   1980
gaatttctcc gattattatt tgtcttttga caccacctca aagtcggggt ccgacgaagt   2040
ggaactggac gatgcagcgg gaagcggaga gctcacgata ggactgggaa gcagcggccg   2100
tgtgactgtt gtcttccagt atgccacaaa cggtgggga aacagatatg ttgcttacac    2160
cgtcggagat tctggatgca aaacaattga agctgttctc cttcacggcc tgaatcctgg   2220
agcgaagctc gttaggaata cgataggcga taattctccg ggtgaatctg aattgtaa    2278
```

<210> SEQ ID NO 11
<211> LENGTH: 4242
<212> TYPE: DNA
<213> ORGANISM: Neospora caninum

<400> SEQUENCE: 11

```
cgggaattcg attccagccg agttcgtgtt cagacgtgta cgccacccac ggtacaattt     60
attcagggga gagaaaaaga agtcgcggca aaaacataaa gctcttcggc agttcaacga    120
tgaaactgca aattaatgaa atgatttaaa ctaatcccag cgcagaacgg agttgcaata    180
accttccgac agagacgcac cggaggacct gggaaccgat ccgaaatgag acgaggacag    240
caacttgaga cggctcattg cgtcgcaact gtgtttgcgt aaccgctgcg agcagttccg    300
ccagcccatg agtgggatgt tcgtgtgctt gggatactag gcggttcacc tgaaaggcgg    360
tcgtcccgct cttaagagcc gccgcgcaac agccgaagcg ctaggaccg ttggtctacc     420 atcgccccat cgctcatgaa ctctagtggg gagagcgtca gctccgcaac aggtcgtgta    480
tctggaggct acagtgagcg tcgcatttca ctcgccagta ctagcagcct tggcctttgg    540
tagcgttgcg atggcctatg ccagtgcgag gcgctaaac tactggcagt agacacacca     600
tctggtgagc tctycctatg tctaaaacgt gaagatgagc gcgtgtgtgc ggatgacaga    660
ggtatcaaga catctgtcag gtagaaattt cttttaaca gttgaacaat cgtttcgtga    720
ctctctggtg gtctgtctgt gtactagatg tactctttcc caagccgctc gaggaacata    780
```

```
cgtgaagcac ggtggtactt cctgtagcaa acatagcag gtaaaggtga tgtggttcga    840
aactgcagtg tgtactgtac tttgggggggt ggcgcacggt tgggcacgcc catttgctag   900
gggttcgggg aagggaaggg tgtgtggttg acggtttatc atcagagaaa ctggagtggg    960
gacaagatta taatacgtca agctgcaagc cgctgtagtt ggagaaagct gttttttgagg  1020
ggcatacttg tttgcgcgga tgatgtacgt atttcaccta aacatgttga aatacgctcg   1080
ctgagaaacg gaggcaaaat tcaggaggaa tggggaaggg tacccgtatg gtgagcacgc   1140
gttgcaaaag cacaagtagg agaacacgcg acatagaaca actcggcggc catgtgtgta   1200
aacggcatta acggatgttt ccaccttac acactctcga tgcgtgggac aatggagtcg    1260
atgaaaacga tgcatggttt ggttgcatga ctgtgcgcag cacaatggcg ttcggacgag   1320
gcaagagggg actgcacgct gcagtcatct taggcttctt tgtcctcctc gccacatcat   1380
ctgtaggatt gggccaaagg tgagtcaaag catgacgtgt tttgctacgt gtaggaacag   1440
cacgttgcgg ttcgaccact tgctcagtag ggtcatgcaa cactttgtgc tgattcaact   1500
ggtgtgcagg gtgcctcgct acccaagtgt ggagtcactc gaagaaagag ttgccgaggc   1560
tctagggcgc cgtagctccg cagcggccag tactcttcca gggagtgaca cgaacatgat   1620
atcagatggt cgcgcaggca gggatgaacc aacagcgagc ccagagcatc attccgtgga   1680
cgctccgacc acgtctgggg aaggcgaggc agatgctggg aaagtaacgc tgaggaacga   1740
tgagggcctt gagggtaata tctcagccga ccatgttcta catcccctc ctgacagtga   1800
acacgagggt ttgcaggaac cgggcacgac gcatcaggag gcgcaagaac cagacgcgag   1860
tgaagcaatg gactcttccg cgctaccact ttccacgtcg ggtaccacat cctaacgaag   1920
tcggttcaac accaggaaca gcgctgcctg ccccgatttt tagcattcca gagctctcac   1980
cggaggaagt tgtctacgtt ttacgggttc agggatcagg cgatttcgaa attagtttcc   2040
aagtaggccg ggtggtgagg cagttggaag ccatcaagag agcatacagg gaggctcacg   2100
ggaagctaga agctgaggag ctggagtcgg aaagggggacc gacggtttcg actcggacga   2160
aactagttga ctttatcaaa gaaaaccaga gacggctgag ggcggcgttt cagaaggtta   2220
agattcagca aaagttggag gagatcgagg aactgttgca gctgtcacac gcactaaaat   2280
ctctaggtgc ccgcctgaga ccctgccaaa aagtaattc cccaatggag gaagagattt    2340
gtcgtaagac gaaagctttg ggcgaaatgg ttgcccagaa agcggaggat cttcgtcagc   2400
atgcgtcaac tgtctcggct ctgctaggtc gcgaagctgt tgagagacag ttgcggcgtg   2460
tcgacagtga acaaccctat gaacaaacag acgccgggt tgcagccaga gcagaggaat   2520
ttcggaaggc actggagaaa gcagcttccg gtgcgagaca attcgtgggg accacagcgg   2580
acgaaatagt ggaggaagtg aaggaggatg ctcagtacct gcgtgatggt gcgaaagaag   2640
tgttgacgaa gagccagcgc gcgctagtag acgcgtttca ggcgatccaa agggctctac   2700
tggaggcgaa ggcaaaggag ctcgtagatg ccgcatcaaa ggaagctgaa gacgctcgta   2760
agatcttagc ggaacagcca gcgtgattcg ccgaggacga agttggtaat gcacggtgaa   2820
tgagggttgg tcatcccaat ccccagcttg atagcgtcac gtgggttttt cgccggggaa   2880
acgatcatta gggaggtgat gtatcgcagt aaacatgggc atatcagcac cagttttttt   2940
acatgtgagg gatgggatcc agtgtaggtg taagggacag ctgtcttca aatttgggct    3000
tcggttgccg ctcccgttct ttcagcatat gtacaggtat gtacagtgaa taagtgcgtg   3060
ggccaatgtg ctctcatcaa tcatgtacag aacatatgtt ttggtcatat ctatgcagcg   3120
cctgcatgag cccatgccgc tcgtgtttta cgaagccaga tgcggtgccg ccctgtccca   3180
```

-continued

```
gctacacatg ctgtgcacgg ggaacaacgg ccatgttgga aaagtcactg tttatataat    3240
gattgacaac taatgaaaaa gcactcaagc gggaaatgtt tcatgcggtc caaagagcag    3300 ggggaaagt cactgtttta taaatgattg tgacaactat ctaatgaaaa agcactcaag     3360
cgggaaatgt tcatgcggt ccaaagagta ggggcgggc gtggtactga tgattaccgc     3420
gtaacaatga ccacgccggc gcagatgtcg cagtgctgta gcgtttgatg ttcttttgta    3480
tggcggaagg gtgacaaggc aaacggcgag agtcgactta cagactcacc accgggcaac   3540
catcggttcc caggtcaata agctggacta ttgtcagcag atgcgatgat aacgcgtgcc   3600
atacataaag agcgtacccg tgctagttaa agatgcgcac gcggttctgt tggcagaggt   3660
cggaggcttg cctcatggag caaccgaggg ggcgcagttc tgtcttcgtg tcttccgttt   3720
gtgtgtttga gaacgaacag atacggcgta tgtgcttgcc ttggtcacag ggagctcacc   3780
acaaagcccg tgtagtcggg ggagtactgc tggacacagt ggcgagaata cgcgtgatca   3840
atgccggcaa tagagaaatc ggcatgaaat tgtgtagcgg atggcgttct gtatgtcgta   3900
caagcgaccc tggatcgtgt gtaccccct acgggcgggc tgccctgtga aggcaatata    3960
aaatgtaatc caatgattcg ttttcatgtt acaccagata ttcttaggac gatggtactg   4020
accatactag catctgagta gtagtctctc ggtgttcggt ggccaatcta cgactctagc   4080
aatgggttcc ctctctaccc taggttccgt agtgtgggca catcacatga tgactgtcga   4140
tccagaaatt gatacacgtg catgcttctc agctatgaca attatgattg ctattcctac   4200
agcagccaac cggatccgaa ttcttcgccc tatagtgaag tc                      4242

<210> SEQ ID NO 12
<211> LENGTH: 1892
<212> TYPE: DNA
<213> ORGANISM: Neospora caninum
<220> FEATURE:
<221> NAME/KEY: CDS
<222> LOCATION: (122)..(1381)

<400> SEQUENCE: 12
gaacaatcgt ttcgtgactc tctggtggtc tgtctgtgta ctagatgtac tctttcccaa     60
gccgctcgag gaacatacgt gaagcacggt ggtacttcct gtagcaaaac atagcagcac    120 a atg gcg ttc gga cga ggc aag agg gga ctg cac gct gca gtc atc tta   169
  Met Ala Phe Gly Arg Gly Lys Arg Gly Leu His Ala Ala Val Ile Leu
  1               5                  10                  15 ggc ttc ttt gtc ctc ctc gcc aca tca tct gta gga ttg ggc caa agg    217
Gly Phe Phe Val Leu Leu Ala Thr Ser Ser Val Gly Leu Gly Gln Arg
             20                  25                  30 gtg cct cgc tac cca agt gtg gag tca ctc gaa gaa aga gtt gcc gag    265
Val Pro Arg Tyr Pro Ser Val Glu Ser Leu Glu Glu Arg Val Ala Glu
         35                  40                  45 gct cta ggg cgc cgt agc tcc gca gcg gcc agt act ctt cca ggg agt    313
Ala Leu Gly Arg Arg Ser Ser Ala Ala Ser Thr Leu Pro Gly Ser
     50                  55                  60 gac acg aac atg ata tca gat ggt cgc gca ggc agg gat gaa cca aca    361
Asp Thr Asn Met Ile Ser Asp Gly Arg Ala Gly Arg Asp Glu Pro Thr
 65                  70                  75                  80 gcg agc cca gag cat cat tcc gtg gac gct ccg acc acg tct ggg gaa    409
Ala Ser Pro Glu His His Ser Val Asp Ala Pro Thr Thr Ser Gly Glu
                 85                  90                  95 ggc gag gca gat gct ggg aaa gta acg ctg agg aac gat gag ggc ctt    457
Gly Glu Ala Asp Ala Gly Lys Val Thr Leu Arg Asn Asp Glu Gly Leu
            100                 105                 110
```

```
gag ggt aat atc tca gcc gac cat gtt cta cat ccc cct cct gac agt      505
Glu Gly Asn Ile Ser Ala Asp His Val Leu His Pro Pro Pro Asp Ser
            115                 120                 125 gaa cac gag gtc ggt tca aca cca gga aca gcg ctg cct gcc ccg att      553
Glu His Glu Val Gly Ser Thr Pro Gly Thr Ala Leu Pro Ala Pro Ile
130                 135                 140 ttt agc att cca gag ctc tca ccg gag gaa gtt gtc tac gtt tta cgg      601
Phe Ser Ile Pro Glu Leu Ser Pro Glu Glu Val Val Tyr Val Leu Arg
145                 150                 155                 160 gtt cag gga tca ggc gat ttc gaa att agt ttc caa gta ggc cgg gtg      649
Val Gln Gly Ser Gly Asp Phe Glu Ile Ser Phe Gln Val Gly Arg Val
                165                 170                 175 gtg agg cag ttg gaa gcc atc aag aga gca tac agg gag gct cac ggg      697
Val Arg Gln Leu Glu Ala Ile Lys Arg Ala Tyr Arg Glu Ala His Gly
            180                 185                 190 aag cta gaa gct gag gag ctg gag tcg gaa agg gga ccg acg gtt tcg      745
Lys Leu Glu Ala Glu Glu Leu Glu Ser Glu Arg Gly Pro Thr Val Ser
        195                 200                 205 act cgg acg aaa cta gtt gac ttt atc aaa gaa aac cag aga cgg ctg      793
Thr Arg Thr Lys Leu Val Asp Phe Ile Lys Glu Asn Gln Arg Arg Leu
    210                 215                 220 agg gcg gcg ttt cag aag gtt aag att cag caa aag ttg gag gag atc      841
Arg Ala Ala Phe Gln Lys Val Lys Ile Gln Gln Lys Leu Glu Glu Ile
225                 230                 235                 240 gag gaa ctg ttg cag ctg tca cac gca cta aaa tct cta ggt gcc cgc      889
Glu Glu Leu Leu Gln Leu Ser His Ala Leu Lys Ser Leu Gly Ala Arg
                245                 250                 255 ctg aga ccc tgc caa aaa agt aat tcc cca atg gag gaa gag att tgt      937
Leu Arg Pro Cys Gln Lys Ser Asn Ser Pro Met Glu Glu Glu Ile Cys
            260                 265                 270 cgt aag acg aaa gct ttg ggc gaa atg gtt gcc cag aaa gcg gag gat      985
Arg Lys Thr Lys Ala Leu Gly Glu Met Val Ala Gln Lys Ala Glu Asp
        275                 280                 285 ctt cgt cag cat gcg tca act gtc tcg gct ctg cta ggt cgc gaa gct     1033
Leu Arg Gln His Ala Ser Thr Val Ser Ala Leu Leu Gly Arg Glu Ala
    290                 295                 300 gtt gag aga cag ttg cgg cgt gtc gac agt gaa caa ccc tat gaa caa     1081
Val Glu Arg Gln Leu Arg Arg Val Asp Ser Glu Gln Pro Tyr Glu Gln
305                 310                 315                 320 aca gac gcc ggg gtt gca gcc aga gca gag gaa ttt cgg aag gca ctg     1129
Thr Asp Ala Gly Val Ala Ala Arg Ala Glu Glu Phe Arg Lys Ala Leu
                325                 330                 335 gag aaa gca gct tcc ggt gcg aga caa ttc gtg ggg acc aca gcg gac     1177
Glu Lys Ala Ala Ser Gly Ala Arg Gln Phe Val Gly Thr Thr Ala Asp
            340                 345                 350 gaa ata gtg gag gaa gtg aag gag gat gct cag tac ctg cgt gat ggt     1225
Glu Ile Val Glu Glu Val Lys Glu Asp Ala Gln Tyr Leu Arg Asp Gly
        355                 360                 365 gcg aaa gaa gtg ttg acg aag agc cag cgc gcg cta gta gac gcg ttt     1273
Ala Lys Glu Val Leu Thr Lys Ser Gln Arg Ala Leu Val Asp Ala Phe
370                 375                 380 cag gcg atc caa agg gct cta ctg gag gcg aag gca aag gag ctc gta     1321
Gln Ala Ile Gln Arg Ala Leu Leu Glu Ala Lys Ala Lys Glu Leu Val
385                 390                 395                 400 gat gcc gca tca aag gaa gct gaa gac gct cgt aag atc tta gcg gaa     1369
Asp Ala Ala Ser Lys Glu Ala Glu Asp Ala Arg Lys Ile Leu Ala Glu
                405                 410                 415 cag cca gcg tga ttcgccgagg acgaagttgg taatgcacgg tgaatgaggg         1421
Gln Pro Ala
```

```
                420
ttggtcatcc caatccccag cttgatagcg tcacgtgggt ttttcgccgg ggaaacgatc    1481
attagggagg tgatgtatcg cagtaaacat gggcatatca gcaccagttt ttttacatgt    1541
gagggatggg atccagtgta ggtgtaaggg acagctgtct ttcaaatttg ggcttcggtt    1601
gccgctcccg ttctttcagc atatgtacag gtatgtacag tgaataagtg cgtgggccaa    1661
tgtgctctca tcaatcatgt acagaacata tgttttggtc atatctatgc agcgcctgca    1721
tgagcccatg ccgctcgtgt tttacgaagc cagatgcggt gccgccctgt cccagctaca    1781
catgctgtgc acggggaaca acggccatgt tggaaaagtc actgttttat aaatgattga    1841
caactaatga aaaagcactc aagcgggaaa tgtttcatgc ggtccaaaga g             1892
```

<210> SEQ ID NO 13
<211> LENGTH: 419
<212> TYPE: PRT
<213> ORGANISM: Neospora caninum

<400> SEQUENCE: 13

```
Met Ala Phe Gly Arg Gly Lys Arg Gly Leu His Ala Ala Val Ile Leu
 1               5                  10                  15

Gly Phe Phe Val Leu Leu Ala Thr Ser Ser Val Gly Leu Gly Gln Arg
                20                  25                  30

Val Pro Arg Tyr Pro Ser Val Glu Ser Leu Glu Glu Arg Val Ala Glu
            35                  40                  45

Ala Leu Gly Arg Arg Ser Ser Ala Ala Ser Thr Leu Pro Gly Ser
        50                  55                  60

Asp Thr Asn Met Ile Ser Asp Gly Arg Ala Gly Arg Asp Glu Pro Thr
 65                  70                  75                  80

Ala Ser Pro Glu His His Ser Val Asp Ala Pro Thr Thr Ser Gly Glu
                85                  90                  95

Gly Glu Ala Asp Ala Gly Lys Val Thr Leu Arg Asn Asp Glu Gly Leu
            100                 105                 110

Glu Gly Asn Ile Ser Ala Asp His Val Leu His Pro Pro Asp Ser
        115                 120                 125

Glu His Glu Val Gly Ser Thr Pro Gly Thr Ala Leu Pro Ala Pro Ile
130                 135                 140

Phe Ser Ile Pro Glu Leu Ser Pro Glu Glu Val Val Tyr Val Leu Arg
145                 150                 155                 160

Val Gln Gly Ser Gly Asp Phe Glu Ile Ser Phe Gln Val Gly Arg Val
                165                 170                 175

Val Arg Gln Leu Glu Ala Ile Lys Arg Ala Tyr Arg Glu Ala His Gly
            180                 185                 190

Lys Leu Glu Ala Glu Leu Glu Ser Glu Arg Gly Pro Thr Val Ser
        195                 200                 205

Thr Arg Thr Lys Leu Val Asp Phe Ile Lys Glu Asn Gln Arg Arg Leu
210                 215                 220

Arg Ala Ala Phe Gln Lys Val Lys Ile Gln Lys Leu Glu Glu Ile
225                 230                 235                 240

Glu Glu Leu Leu Gln Leu Ser His Ala Leu Lys Ser Leu Gly Ala Arg
                245                 250                 255

Leu Arg Pro Cys Gln Lys Ser Asn Ser Pro Met Glu Glu Ile Cys
            260                 265                 270

Arg Lys Thr Lys Ala Leu Gly Glu Met Val Ala Gln Lys Ala Glu Asp
        275                 280                 285
```

```
Leu Arg Gln His Ala Ser Thr Val Ser Ala Leu Leu Gly Arg Glu Ala
    290                 295                 300

Val Glu Arg Gln Leu Arg Arg Val Asp Ser Glu Gln Pro Tyr Glu Gln
305                 310                 315                 320

Thr Asp Ala Gly Val Ala Ala Arg Ala Glu Glu Phe Arg Lys Ala Leu
                325                 330                 335

Glu Lys Ala Ala Ser Gly Ala Arg Gln Phe Val Gly Thr Thr Ala Asp
            340                 345                 350

Glu Ile Val Glu Val Lys Gly Asp Ala Gln Tyr Leu Arg Asp Gly
        355                 360                 365

Ala Lys Glu Val Leu Thr Lys Ser Gln Arg Ala Leu Val Asp Ala Phe
    370                 375                 380

Gln Ala Ile Gln Arg Ala Leu Leu Glu Ala Lys Ala Lys Glu Leu Val
385                 390                 395                 400

Asp Ala Ala Ser Lys Glu Ala Asp Ala Arg Lys Ile Leu Ala Glu
                405                 410                 415

Gln Pro Ala

<210> SEQ ID NO 14
<211> LENGTH: 20
<212> TYPE: DNA
<213> ORGANISM: Neospora caninum

<400> SEQUENCE: 14
aattaaccct cactaaaggg                                           20

<210> SEQ ID NO 15
<211> LENGTH: 22
<212> TYPE: DNA
<213> ORGANISM: Neospora caninum

<400> SEQUENCE: 15
gtaatacgac tcactatagg gc                                        22

<210> SEQ ID NO 16
<211> LENGTH: 20
<212> TYPE: DNA
<213> ORGANISM: Neospora caninum

<400> SEQUENCE: 16
gccgcgactt cttttctct                                            20

<210> SEQ ID NO 17
<211> LENGTH: 20
<212> TYPE: DNA
<213> ORGANISM: Neospora caninum

<400> SEQUENCE: 17
ctcgatcgcc tcctttactg                                           20

<210> SEQ ID NO 18
<211> LENGTH: 20
<212> TYPE: DNA
<213> ORGANISM: Neospora caninum

<400> SEQUENCE: 18
tgctagtact ggcgagtgaa                                           20

<210> SEQ ID NO 19
```

```
<211> LENGTH: 20
<212> TYPE: DNA
<213> ORGANISM: Neospora caninum

<400> SEQUENCE: 19
caggtttgcc acacattttt                                                    20

<210> SEQ ID NO 20
<211> LENGTH: 21
<212> TYPE: DNA
<213> ORGANISM: Neospora caninum

<400> SEQUENCE: 20
atgtttcctc ctcgggcagt g                                                  21

<210> SEQ ID NO 21
<211> LENGTH: 23
<212> TYPE: DNA
<213> ORGANISM: Neospora caninum

<400> SEQUENCE: 21
tcacgcgacg ccagccgcta tcg                                                23

<210> SEQ ID NO 22
<211> LENGTH: 20
<212> TYPE: DNA
<213> ORGANISM: Neospora caninum

<400> SEQUENCE: 22
gccctgacaa ttcgaccgcc                                                    20

<210> SEQ ID NO 23
<211> LENGTH: 21
<212> TYPE: DNA
<213> ORGANISM: Neospora caninum

<400> SEQUENCE: 23
cccacaacat ccaagtcgtt c                                                  21

<210> SEQ ID NO 24
<211> LENGTH: 20
<212> TYPE: DNA
<213> ORGANISM: Neospora caninum

<400> SEQUENCE: 24
gttttgcacc atccttagtg                                                    20

<210> SEQ ID NO 25
<211> LENGTH: 19
<212> TYPE: DNA
<213> ORGANISM: Neospora caninum

<400> SEQUENCE: 25
gagagtttgc tttgcaccg                                                     19

<210> SEQ ID NO 26
<211> LENGTH: 21
<212> TYPE: DNA
<213> ORGANISM: Neospora caninum

<400> SEQUENCE: 26
ccagccgagt tcgtgttcag a                                                  21
```

<210> SEQ ID NO 27
<211> LENGTH: 24
<212> TYPE: DNA
<213> ORGANISM: Neospora caninum

<400> SEQUENCE: 27
caacgtggat ccgattcaag cttc                                    24

<210> SEQ ID NO 28
<211> LENGTH: 20
<212> TYPE: DNA
<213> ORGANISM: Neospora caninum

<400> SEQUENCE: 28
aaagctcttc ggcagttcaa                                         20

<210> SEQ ID NO 29
<211> LENGTH: 18
<212> TYPE: DNA
<213> ORGANISM: Neospora caninum

<400> SEQUENCE: 29
ccgcgctacc actttcca                                           18

<210> SEQ ID NO 30
<211> LENGTH: 18
<212> TYPE: DNA
<213> ORGANISM: Neospora caninum

<400> SEQUENCE: 30
gtaatacgac tcactata                                           18

<210> SEQ ID NO 31
<211> LENGTH: 19
<212> TYPE: DNA
<213> ORGANISM: Neospora caninum

<400> SEQUENCE: 31
ccgcaacgtg ctgttccta                                          19

<210> SEQ ID NO 32
<211> LENGTH: 18
<212> TYPE: DNA
<213> ORGANISM: Neospora caninum

<400> SEQUENCE: 32
catcagagaa actggagt                                           18

<210> SEQ ID NO 33
<211> LENGTH: 24
<212> TYPE: DNA
<213> ORGANISM: Neospora caninum

<400> SEQUENCE: 33
ggccaagctt gctagtactg gcga                                    24

<210> SEQ ID NO 34
<211> LENGTH: 31
<212> TYPE: DNA
<213> ORGANISM: Neospora caninum

<400> SEQUENCE: 34
atccaatgca tcttgctgaa tgccttaaaa g                            31

POLYNUCLEOTIDE MOLECULES ENCODING NEOSPORA PROTEINS

This application claims benefit of 60/112,282 Dec. 15, 1998 and claims benefit of 60/079,389 Mar. 26, 1998.

1. FIELD OF THE INVENTION

The present invention is in the field of animal health, and is directed to vaccine compositions and diagnostics for disease. More particularly, the present invention relates to polynucleotide molecules comprising nucleotide sequences encoding GRA1, GRA2, SAG1, MIC1, and MAG1 proteins from Neospora, which polynucleotide molecules and proteins are useful in the production of vaccines against neosporosis, and as diagnostic reagents.

2. BACKGROUND OF THE INVENTION

Neospora is a pathogenic protozoan parasite of animals that has been recognized as a major cause of abortion, neonatal death, congenital infection, and encephalitic disease in mammals. Dubey and Lindsay, 1996, Vet. Parasitol. 67:1–59; Dubey and Lindsay, 1993, Parasitology Today, 9:452–458. *Neospora caninum* infects dogs, and congenitally infects pups, often leading to paralysis. Tachyzoites of *N. caninum* have been isolated from naturally infected pups. Lindsay and Dubey, 1989, J. Parasitol. 75:163–165. Neospora is a major cause of abortion in dairy and beef cattle. Cases of Neospora-related disease, i.e., neosporosis, have also been reported in goats, sheep and horses.

Although *N. caninum* is superficially similar to the pathogen, *Toxoplasma gondii*, *N. caninum* and *T. gondii* have been distinguished from each other both antigenically and ultrastructurally. Dubey and Lindsay, 1993, above. In addition, Neospora-like protozoan parasites isolated from the brains of aborted bovine fetuses and continuously cultured in vitro were shown to be antigenically and ultrastructurally distinct from both *T. gondii* and *Hammondia hammondi*, and were most similar to *N. caninum*. Conrad et al., 1993, Parasitology 106:239–249. Furthermore, analysis of nuclear small subunit ribosomal RNA genes revealed no nucleotide differences between strains of Neospora isolated from cattle and dogs, but showed consistent differences between Neospora and *T. gondii*. Marsh etal., 1995, J. Parasitol. 81:530–535.

The etiologic role of a bovine isolate of Neospora in bovine abortion and congenital disease has been confirmed. Barr et aL, 1994, J. Vet. Diag. Invest. 6:207–215. A rodent model of central nervous system neosporosis has been developed using inbred BALB/c mice infected with *N. caninum*. Lindsay et al., 1995, J. Parasitol. 81:313–315. In addition, models to study transplacental transmission of N. caninum in pregnant outbred and inbred mice have been described by Cole et aL, 1995, J. Parasitol. 81:730–732, and by Long et al., 1996, J. Parasitol. 82:608–611, respectively. An experimental *N. caninum* pygmy goat model that closely resembles naturally acquired Neospora-induced cattle abortion has been demonstrated. Lindsay et al., 1995, Am. J. Vet. Res. 56:1176–1180. An experimental N. caninum sheep model that closely resembles naturally acquired Neospora-induced cattle abortion has also been demonstrated. Buxton et al., 1997, J. Comp. Path. 117:1–16.

In *T. gondii*, electron dense granules comprising an excretory-secretory group of antigens are present in the cytoplasm of tachyzoites. These antigens have been designated as GRA proteins. The GRAL protein of *T. gondii* has been reported to have a molecular weight ranging from about 22–27 kDa, and the GRA2 protein of *T. gondii* has been reported to have a molecular weight of about 28 kDa. Sam-Yellowe, 1996, Parasitol. Today 12:308–315. Similar electron dense granules are present in the cytoplasm of *N. caninum* tachyzoites (Bjerkas et al., 1994, Clin. Diag. Lab. Immunol. 1:214–221; Hemphill et aL, 1998, Intl. J. Parasitol. 28:429–438).

*T. gondii* cells are also known to comprise a group of major surface antigens that have been designated as SAG. The SAG1 protein of *T. gondii* is reported to have a molecular weight of about 30 kDa. Kasper et al., 1983, J. Immunol. 130:2407–2412. Monoclonal antibodies directed against *T. gondii* SAG1 protein significantly blocked the ability of *T. gondii* tachyzoites to invade bovine kidney cells under tissue culture conditions. Grimwood and Smith, 1996, Intl. J. Parasitol. 26: 169–173. Because *T. gondii* SAG1 appears to play a role in the invasion process, it has been hypothesized that SAG1 may be necessary to support the virulence phenotype. Windeck and Gross, 1996, Parasitol. Res. 82:715–719. Consistent with this hypothesis is the observation that mice immunized with T. gondii SAG1 protein and then challenged with *T. gondii* had reduced toxoplasma cyst formation in their brains than did control mice. Debard et al., 1996, Infect. Immun., 64:2158–2166. *T. gondii* SAG1 may be functionally related to a similar molecule in *N. caninum* designated as NC-p36 described by Hemphill et al., 1997, Parasitol. 115:371–380.

Micronemes are intracelluar organelles located at the apical end of tachyzoites of both *T. gondii* and Neospora, and may play a role in host cell recognition and attachment to the host cell surface during invasion. Formaux etal., 1996, Curr. Top. Microbiol. Immunol. 219:55–58. At least 4 different microneme-associated (MIC) proteins have been identified in *T. gondii*. The MIC1 protein of *T. gondii* is about 60 kDa, binds to the surface of host cells, and has been reported to have partial homology to thrombospondin-related adhesive protein (TRAP) from *Plasmodium falciparum* which binds to human hepatocytes. Robson et al. 1995 EMBO J. 14:3883–3894.

The conversion of parasites from tachyzoites to bradyzoites is critical for chronic infection and persistence of *T. gondii*. A gene expressing an immunodominant, bradyzoite-specific 65 kD antigen, designated as MAG1, has been identified in *T. gondii*. Parmley et a/., 1994, Mol. Biochem. Parasitol. 66:283–296. MAG1 has been reported to be specifically expressed in bradyzoite cysts, but not in the tachyzoite stage. This specificity of expression may indicate the involvement of MAG1 in the conversion between tachyzoite and bradyzoite stages of the life cycle of the parasite. Bohne et al., 1996, Curr. Topics Microbiol. Immunol. 219:81–91.

Identification in Neospora of protein homologs of *T. gondii* GRA1, GRA2, SAG1, MIC1, and MAG1 proteins, and the nucleotide sequence of polynucleotide molecules encoding said Neospora proteins, will serve to facilitate the development of vaccines against neosporosis, as well as diagnostic reagents.

3. SUMMARY OF THE INVENTION

The present invention provides an isolated polynucleotide molecule comprising a nucleotide sequence encoding the GRA1 protein from *N. caninum*. In a preferred embodiment, the GRA1 protein has the amino acid sequence of SEQ ID NO:2. In a further preferred embodiment, the isolated GRA1-encoding polynucleotide molecule of the present invention comprises a nucleotide sequence selected from the group consisting of the nucleotide sequence of SEQ ID NO:1 from about nt 205 to about nt 777, the nucleotide sequence of the open reading frame (ORF) of the GRA1 gene, which is presented in SEQ ID NO:3 from about nt 605 to about nt 1304, and the nucleotide sequence of the GRA1-encoding ORF of plasmid pRC77 (ATCC 209685). In a non-limiting embodiment, the isolated GRA1-encoding polynucleotide molecule of the present invention comprises a nucleotide sequence selected from the group consisting of the nucleotide sequence of SEQ ID NO:1 and SEQ ID NO:3. The present invention further provides an isolated polynucleotide molecule having a nucleotide sequence that is homologous to the nucleotide sequence of a GRA1-encoding polynucleotide molecule of the present invention. The present invention further provides an isolated polynucleotide molecule comprising a nucleotide sequence that encodes a polypeptide that is homologous to the GRA1 protein of N. caninum. The present invention further provides a polynucleotide molecule consisting of a nucleotide sequence that is a substantial portion of any of the aforementioned GRA1-related polynucleotide molecules.

The present invention further provides an isolated polynucleotide molecule comprising a nucleotide sequence encoding the GRA2 protein from N. caninum. In a preferred embodiment, the GRA2 protein has the amino acid sequence of SEQ ID NO:5. In a further preferred embodiment, the isolated GRA2-encoding polynucleotide molecule of the present invention comprises a nucleotide sequence selected from the group consisting of the nucleotide sequence of the ORF of SEQ ID NO:4, which is from about nt 25 to about nt 660, and the nucleotide sequence of the GRA2-encoding ORF of plasmid pRC5 (ATCC 209686). In a non-limiting embodiment, the isolated GRA2-encoding polynucleotide molecule of the present invention comprises the nucleotide sequence of SEQ ID NO:4. The present invention further provides an isolated polynucleotide molecule having a nucleotide sequence that is homologous to the nucleotide sequence of a GRA2-encoding polynucleotide molecule of the present invention. The present invention further provides an isolated polynucleotide molecule comprising a nucleotide sequence that encodes a polypeptide that is homologous to the GRA2 protein of N. caninum. The present invention further provides a polynucleotide molecule consisting of a nucleotide sequence that is a substantial portion of any of the aforementioned GRA2-related polynucleotide molecules.

The present invention further provides an isolated polynucleotide molecule comprising a nucleotide sequence encoding the SAG1 protein from N. caninum. In a preferred embodiment, the SAG1 protein has the amino acid sequence of SEQ ID NO:7. In a further preferred embodiment, the isolated SAG1-encoding polynucleotide molecule of the present invention comprises a nucleotide sequence selected from the group consisting of the nucleotide sequence of the ORF of SEQ ID NO:6, which is from about nt 130 to about nt 1089, and the nucleotide sequence of the SAG1-encoding ORF of plasmid pRC102 (ATCC 209687). In a non-limiting embodiment, the isolated SAG1-encoding polynucleotide molecule of the present invention comprises the nucleotide sequence of SEQ ID NO:6. The present invention further provides an isolated polynucleotide molecule having a nucleotide sequence that is homologous to the nucleotide sequence of a SAG1-encoding polynucleotide molecule of the present invention. The present invention further provides an isolated polynucleotide molecule comprising a nucleotide sequence that encodes a polypeptide that is homologous to the SAG1 protein of N. caninum. The present invention further provides a polynucleotide molecule consisting of a nucleotide sequence that is a substantial portion of any of the aforementioned SAG 1-related polynucleotide molecules.

The present invention further provides an isolated polynucleotide molecule comprising a nucleotide sequence encoding the MIC1 protein from N. caninum. In a preferred embodiment, the MIC1 protein has the amino acid sequence of SEQ ID NO:9. In a further preferred embodiment, the isolated MIC1-encoding polynucleotide molecule of the present invention comprises a nucleotide sequence selected from the group consisting of the nucleotide sequence of the ORF of SEQ ID NO:8 from about nt 138 to about nt 1520, the nucleotide sequence of the ORF of the MIC1 gene, which is presented as SEQ ID NO:10, and the nucleotide sequence of the MIC1-encoding ORF of plasmid pRC340 (ATCC 209688). In a non-limiting embodiment, the isolated MIC1-encoding polynucleotide molecule of the present invention comprises a nucleotide sequence selected from the group consisting of the nucleotide sequence of SEQ ID NO:8, and the nucleotide sequence of SEQ ID NO:10. The present invention further provides an isolated polynucleotide molecule having a nucleotide sequence that is homologous to the nucleotide sequence of a MIC1-encoding polynucleotide molecule of the present invention. The present invention further provides an isolated polynucleotide molecule comprising a nucleotide sequence that encodes a polypeptide that is homologous to the MIC1 protein of N. caninum. The present invention further provides a polynucleotide molecule consisting of a nucleotide sequence that is a substantial portion of any of the aforementioned MIC1-related polynucleotide molecules.

The present invention further provides an isolated polynucleotide molecule comprising a nucleotide sequence encoding the MAG1 protein from N. caninum. The MAG1 protein has a putative amino acid sequence shown in SEQ ID NO:13. In a preferred embodiment, the isolated MAG1-encoding polynucleotide molecule of the present invention comprises a nucleotide sequence selected from the group consisting of the nucleotide sequence presented in SEQ ID NO:11 from about nt 1305 to about nt 2786, a cDNA molecule prepared therefrom, such as a cDNA molecule having the ORF of SEQ ID NO:12 from about nt 122 to about nt 1381, and the nucleotide sequence of the MAG1-encoding ORF present in plasmid bd304 (ATCC 203413). The present invention further provides a polynucleotide molecule having a nucleotide sequence of any ORF present in SEQ ID NO:11. In a non-limiting embodiment, the isolated MAG1-encoding polynucleotide molecule of the present invention comprises a nucleotide sequence selected from the group consisting of SEQ ID NO:11 and SEQ ID NO:12. The present invention further provides an isolated polynucleotide molecule having a nucleotide sequence that is homologous to the nucleotide sequence of a MAG1-encoding polynucleotide molecule of the present invention. The present invention further provides an isolated polynucleotide molecule comprising a nucleotide sequence that encodes a polypeptide that is homologous to the MAG1 protein of N. caninum. The present invention further provides a polynucleotide molecule consisting of a nucleotide sequence that is a substantial portion of any of the aforementioned MAG1-related polynucleotide molecules.

The present invention further provides a polynucleotide molecule comprising the nucleotide sequence of the promoters of the N. caninum GRA1 and MAG1 genes, which is presented in SEQ ID NO:11 from about nt 127 to about nt 703, and includes its complementary sequence.

The present invention further provides oligonucleotide molecules that hybridize to any of the polynucleotide molecules of the present invention, or that hybridize to a polynucleotide molecule having a nucleotide sequence that is the complement of any of the polynucleotide molecules of the present invention.

The present invention further provides compositions and methods for cloning and expressing any of the polynucleotide molecules of the present invention, including recombinant cloning vectors, recombinant expression vectors, transformed host cells comprising any of said vectors, and novel strains or cell lines derived therefrom. More particularly, the present invention provides a recombinant vector comprising a polynucleotide molecule having a nucleotide sequence encoding the GRA1, GRA2, SAG1, MIC1 or MAG1 protein of N. caninum. In specific, though non-limiting, embodiments, the present invention provides plasmid pRC77 (ATCC 209685) encoding GRA1; plasmid pRC5 (ATCC 209686) encoding GRA2; plasmid pRC102 (ATCC 209687) encoding SAG1; plasmid pRC340 (ATCC 209688) encoding MIC1; and plasmid bd304 (ATCC 203413) comprising the MAG1 gene sequence and the MAG1IGRA1 bidirectional promoter region.

The present invention further provides a substantially purified or isolated N. caninum polypeptide selected from the group consisting of GRA1, GRA2, SAG1, MIC1 and MAG1 proteins. In a preferred embodiment, the N. caninum GRA1 protein has the amino acid sequence of SEQ ID NO:2. In another preferred embodiment, the N. caninum GRA2 protein has the amino acid sequence of SEQ ID NO:5. In another preferred embodiment, the N. caninum SAG1 protein has the amino acid sequence of SEQ ID NO:7. In another preferred embodiment, the N. caninum MIC1 protein has the amino acid sequence of SEQ ID NO:9. In another preferred embodiment, the N. caninum MAG1 protein has the amino acid sequence of SEQ ID NO:13. The present invention further provides substantially purified or isolated polypeptides that are homologous to any of the aforementioned N. caninum proteins. The present invention further provides polypeptides which are fusion proteins comprising any of the aforementioned polypeptides fused to a carrier or fusion partner, as known in the art. The present invention further provides polypeptides consisting of a substantial portion of any of the aforementioned polypeptides. The polypeptides of the present invention are useful both in vaccine compositions to protect mammals against neosporosis and as diagnostic reagents.

The present invention further provides a method of preparing any of the aforementioned polypeptides, comprising culturing host cells transformed with a recombinant expression vector, said vector comprising a polynucleotide molecule comprising a nucleotide sequence encoding any of the aforementioned polypeptides, wherein the nucleotide sequence is in operative association with one or more regulatory elements, under conditions conducive to the expression of the polypeptide, and recovering the expressed polypeptide from the cell culture.

The present invention further provides antibodies specifically directed against a N.caninum GRA1, GRA2, SAG1, MIC1 or MAG1 protein.

The present invention further provides genetic constructs for use in mutating a Neospora GRA1, GRA2, SAG1, MIC1 or MAG1 gene to produce modified Neospora cells. Such modified Neospora cells are useful in vaccine compositions to protect mammals against neosporosis. In a preferred though non-limiting embodiment, a genetic construct of the present invention comprises a polynucleotide molecule comprising a nucleotide sequence that is otherwise the same as a nucleotide sequence encoding a GRA1, GRA2, SAG1, MIC1 or MAG1 protein from N. caninum, or a substantial portion thereof, but that further comprises one or more mutations, i.e., one or more nucleotide deletions, insertions and/or substitutions, that can serve to mutate the gene. Once transformed into cells of Neospora, the polynucleotide molecule of the genetic construct is specifically targeted, e.g., by homologous recombination, to the particular Neospora gene, and either deletes or replaces the gene or a portion thereof, or inserts into the gene. As a result of this recombination event, the Neospora gene is mutated. The resulting mutated gene is preferably partially or fully disabled in that it encodes either a partially defective or fully defective protein, or fails to encode a protein. The present invention further provides Neospora cells which have been modified by one or more of said gene mutations, and methods of preparing modified Neospora cells using a genetic construct of the present invention.

The present invention further provides a vaccine against neosporosis, comprising an immunologically effective amount of a polypeptide of the present invention, or an immunologically effective amount of a polynucleotide molecule of the present invention, or an immunologically effective amount of modified Neospora cells of the present invention; and a veterinarily acceptable carrier. In a preferred embodiment, the vaccine of the present invention comprises modified live cells of N. caninum that express a GRA1⁻, GRA2⁻, SAG1⁻, MIC1⁻ or MAG1⁻ phenotype, or a combination of said phenotypes. In a non-limiting embodiment, the vaccine is a combination vaccine for protecting a mammal against neosporosis and, optionally, one or more other diseases or pathological conditions that can afflict the mammal, which combination vaccine comprises an immunologically effective amount of a first component comprising a polypeptide, polynucleotide molecule, or modified Neospora cells of the present invention; an immunologically effective amount of a second component that is different from the first component, and that is capable of inducing, or contributing to the induction of, a protective response against a disease or pathological condition that can afflict the mammal; and a veterinarily acceptable carrier.

The present invention further provides a method of preparing a vaccine against neosporosis, comprising combining an immunologically effective amount of a N. caninum polypeptide of the present invention, or an immunologically effective amount of a polynucleotide molecule of the present invention, or an immunologically effective amount of modified Neospora cells of the present invention, with a veterinarily acceptable carrier, in a form suitable for administration to a mammal.

The present invention further provides a method of vaccinating a mammal against neosporosis, comprising administering to the mammal an immunologically effective amount of a vaccine of the present invention.

The present invention further provides a kit for vaccinating a mammal against neosporosis, comprising a first container having an immunologically effective amount of a polypeptide of the present invention, or an immunologically effective amount of a polynucleotide molecule of the present invention, or an immunologically effective amount of modified Neospora cells of the present invention; and a second container having a veterinarily acceptable carrier or diluent.

4. DETAILED DESCRIPTION OF THE INVENTION

4.1. Polynucleotide Molecules

An isolated polynucleotide molecule of the present invention can have a nucleotide sequence derived from any species or strain of Neospora, but is preferably from a pathogenic species of Neospora such as *N. caninum*. A non-limiting example of a strain of *N. caninum* from which a polynucleotide molecule of the present invention can be isolated or derived is strain NC-1, which is available in host MARC-145 monkey kidney cells under Accession No. CRL-12231 from the American Type Culture Collection (ATCC), located at 10801 University Blvd, Manassas, Va., 20110, USA. Strain NC-1 is also described in Dubey et al., 1988, J. Am. Vet. Med. Assoc. 193:1259–63, which publication is incorporated herein by reference. Alternatively, pathogenic strains or species of Neospora for use in practicing the present invention can be isolated from organs, tissues or body fluids of infected animals using standard isolation techniques such as those described in the publications reviewed above.

As used herein, the terms "polynucleotide molecule," "polynucleotide sequence," "coding sequence," "open-reading frame (ORF)," and the like, are intended to refer to both DNA and RNA molecules, which can either be single-stranded or double-stranded, and that can include one or more prokaryotic sequences, cDNA sequences, genomic DNA sequences including exons and introns, and chemically synthesized DNA and RNA sequences, and both sense and corresponding anti-sense strands. As used herein, the term "ORF" refers to the minimal nucleotide sequence required to encode a particular Neospora protein, i.e., either a GRA1, GRA2, SAG1, MIC1 or MAG1 protein, without any intervening termination codons.

Production and manipulation of the polynucleotide molecules and oligonucleotide molecules disclosed herein are within the skill in the art and can be carried out according to recombinant techniques described, among other places, in Maniatis et al., 1989, *Molecular Cloning, A Laboratory Manual*, Cold Spring Harbor Laboratory Press, Cold Spring Harbor, N.Y.; Ausubel et al., 1989, *Current Protocols In Molecular Biology*, Greene Publishing Associates & Wiley Interscience, N.Y.; Sambrook et al., 1989, *Molecular Cloning: A Laboratory Manual,* 2d ed., Cold Spring Harbor Laboratory Press, Cold Spring Harbor, N.Y.; Innis et al. (eds), 1995, *PCR Strategies*, Academic Press, Inc., San Diego; and Erlich (ed), 1992, *PCR Technology,* Oxford University Press, New York, all of which are incorporated herein by reference.

4.1.1. GRA1-Related Polynucleotide Molecules

References herein below to the nucleotide sequences shown in SEQ ID NOS:1 and 3, and to substantial portions thereof, are intended to also refer to the corresponding nucleotide sequences and substantial portions thereof, respectively, as present in plasmid pRC77 (ATCC 209685), unless otherwise indicated. In addition, references herein below to the amino acid sequences shown in SEQ ID NO:2, and to substantial portions and peptide fragments thereof, are intended to also refer to the corresponding amino acid sequences, and substantial portions and peptide fragments thereof, respectively, encoded by the corresponding GRA1-encoding nucleotide sequence present in plasmid pRC77 (ATCC 209685), unless otherwise indicated.

The present invention provides an isolated polynucleotide molecule comprising a nucleotide sequence encoding the GRA1 protein from *N. caninum.* In a preferred embodiment, the GRA1 protein has the amino acid sequence of SEQ ID NO:2. In a further preferred embodiment, the isolated GRA1-encoding polynucleotide molecule of the present invention comprises a nucleotide sequence selected from the group consisting of the nucleotide sequence of SEQ ID NO:1 from about nt 205 to about nt 777, the nucleotide sequence of the open reading frame (ORF) of the GRA1 gene, which is presented in SEQ ID NO:3 from about nt 605 to about nt 1304, and the nucleotide sequence of the GRA1-encoding ORF of plasmid pRC77 (ATCC 209685). In a non-limiting embodiment, the isolated GRA1-encoding polynucleotide molecule of the present invention comprises a nucleotide sequence selected from the group consisting of the nucleotide sequence of SEQ ID NO:1 and SEQ ID NO:3. The GRA1 gene presented in SEQ ID NO:3 comprises an ORF from nt 605 to nt 855 and from nt 983 to nt 1304 with an intervening intron extending from nt 856 to nt 982. In addition, putative promoter motifs have been identified within 150 bp 5' of the mRNA start site that are similar to those found in *T. gondii* GRA genes (see Section 5.3, below).

The present invention further provides an isolated polynucleotide molecule having a nucleotide sequence that is homologous to the nucleotide sequence of a GRA1-encoding polynucleotide molecule of the present invention. The term "homologous" when used to refer to a GRA1-related polynucleotide molecule means a polynucleotide molecule having a nucleotide sequence: (a) that encodes the same protein as one of the aforementioned GRA1-encoding polynucleotide molecules of the present invention, but that includes one or more silent changes to the nucleotide sequence according to the degeneracy of the genetic code; or (b) that hybridizes to the complement of a polynucleotide molecule having a nucleotide sequence that encodes the amino acid sequence of the *N. caninum* GRA1 protein, under moderately stringent conditions, i.e., hybridization to filter-bound DNA in 0.5 M $NaHPO_4$, 7% sodium dodecyl sulfate (SDS), 1 mM EDTA at 65° C., and washing in 0.2×SSC/0.1% SDS at 42° C. (see Ausubel et al. (eds.), 1989, *Current Protocols in Molecular Biology,* Vol. I, Green Publishing Associates, Inc., and John Wiley & Sons, Inc., New York, at p. 2.10.3), and that is useful in practicing the present invention. In a preferred embodiment, the homologous polynucleotide molecule hybridizes to the complement of a polynucleotide molecule having a nucleotide sequence that encodes the amino acid sequence of the *N. caninum* GRA1 protein under highly stringent conditions, i.e., hybridization to filter-bound DNA in 0.5 M $NaHPO_4$, 7% SDS 1 mM EDTA at 65° C., and washing in 0.1×SSC/0. 1% SDS at 68° C. (Ausubel et al., 1989, above), and is useful in practicing the present invention. In a more preferred embodiment, the homologous polynucleotide molecule hybridizes under highly stringent conditions to the complement of a polynucleotide molecule consisting of a nucleotide sequence selected from the group consisting of the ORF of SEQ ID NO:1, which is from about nt 205 to about nt 777, and the ORF of the GRA1 gene, which is presented in SEQ ID NO:3 from about nt 605 to about nt 1304, and which is useful in practicing the present invention.

As used herein, a polynucleotide molecule is "useful in practicing the present invention" where the polynucleotide molecule can be used to amplify a Neospora-specific polynucleotide molecule using standard amplification techniques, or as a diagnostic reagent to detect the presence of a Neospora-specific polynucleotide in a fluid or tissue sample from a Neospora- infected animal.

Polynucleotide molecules of the present invention having nucleotide sequences that are homologous to the nucleotide sequence of a GRA1-encoding polynucleotide molecule of the present invention do not include polynucleotide molecules having the native nucleotide sequence of *T. gondii* encoding a *T. gondii* GRA protein, and further have no more than about 90%, and preferably no more than about 80%, sequence identity to such a *T. gondii* polynucleotide molecule, wherein sequence identity is determined by use of the BLASTN algorithm (GenBank, National Center for Biotechnology Information).

The present invention further provides an isolated polynucleotide molecule comprising a nucleotide sequence that encodes a polypeptide that is homologous to the *N. caninum* GRA1 protein. As used herein to refer to polypeptides that are homologous to the *N. caninum* GRA1 protein, the term "homologous" refers to a polypeptide otherwise having the amino acid sequence of the *N. caninum* GRA1 protein, but in which one or more amino acid residues have been conservatively substituted with a different amino acid residue, where the resulting polypeptide is useful in practicing the present invention. Conservative amino acid substitutions are well-known in the art. Rules for making such substitutions include those described by Dayhof, M. D., 1978, Nat. Biomed. Res. Found., Washington, D.C., Vol. 5, Sup. 3, among others. More specifically, conservative amino acid substitutions are those that generally take place within a family of amino acids that are related in acidity, polarity, or bulkiness of their side chains. Genetically encoded amino acids are generally divided into four groups: (1) acidic= aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan and tyrosine are also jointly classified as aromatic amino acids. One or more replacements within any particular group, e.g., of a leucine with an isoleucine or valine, or of an aspartate with a glutamate, or of a threonine with a serine, or of any other amino acid residue with a structurally related amino acid residue, e.g., an amino acid residue with similar acidity, polarity, bulkiness of side chain, or with similarity in some combination thereof, will generally have an insignificant effect on the function or immunogenicity of the polypeptide. In a preferred embodiment, the homologous polypeptide has at least about 70%, more preferably at least about 80%, and most preferably at least about 90% sequence identity to SEQ ID NO:2.

As used herein, a polypeptide is "useful in practicing the present invention" where the polypeptide can be used as a diagnostic reagent to detect the presence of Neospora-specific antibodies in a blood or serum sample from an animal that is currently infected, or that has been infected, with Neospora.

The present invention further provides a polynucleotide molecule consisting of a substantial portion of any of the aforementioned Neospora GRA1-related polynucleotide molecules of the present invention. As used herein, a "substantial portion" of a GRA1-related polynucleotide molecule means a polynucleotide molecule consisting of less than the complete nucleotide sequence of the GRA1-related polynucleotide molecule, but comprising at least about 5%, more preferably at least about 10%, and most preferably at least about 20%, of the nucleotide sequence of the GRA1-related polynucleotide molecule, and that is useful in practicing the present invention, as usefulness is defined above for polynucleotide molecules.

In addition to the nucleotide sequences of any of the aforementioned GRA1-related polynucleotide molecules, polynucleotide molecules of the present invention can further comprise, or alternatively may consist of, nucleotide sequences selected from those that naturally flank the GRA1 ORF or gene in situ in *N. caninum,* and include the nucleotide sequences shown in SEQ ID NO:1 from about nt 1 to about nt 204 and from about nt 778 to about nt 1265, or as shown in SEQ ID NO:3 from about nt 1 to about nt 604, and from about nt 1305 to about nt 1774, or substantial portions thereof.

4.1.2. GRA2-Related Polynucleotide Molecules

References herein below to the nucleotide sequence shown in SEQ ID NO:4, and to substantial portions thereof, are intended to also refer to the corresponding nucleotide sequence and substantial portions thereof, respectively, as present in plasmid pRC5 (ATCC 209686), unless otherwise indicated. In addition, references herein below to the amino acid sequence shown in SEQ ID NO:5, and to substantial portions and peptide fragments thereof, are intended to also refer to the corresponding amino acid sequence, and substantial portions and peptide fragments thereof, respectively, encoded by the corresponding GRA2-encoding nucleotide sequence present in plasmid pRC5 (ATCC 209686), unless otherwise indicated.

The present invention further provides an isolated polynucleotide molecule comprising a nucleotide sequence encoding the GRA2 protein from *N. caninum.* In a preferred embodiment, the GRA2 protein has the amino acid sequence of SEQ ID NO:5. In a further preferred embodiment, the isolated GRA2-encoding polynucleotide molecule of the present invention comprises a nucleotide sequence selected from the group consisting of the nucleotide sequence of the ORF of SEQ ID NO:4, which is from about nt 25 to about nt 660, and the nucleotide sequence of the GRA2-encoding ORF of plasmid pRC5 (ATCC 209686). In a non-limiting embodiment, the isolated GRA2-encoding polynucleotide molecule of the present invention comprises the nucleotide sequence of SEQ ID NO:4.

The present invention further provides an isolated polynucleotide molecule having a nucleotide sequence that is homologous to the nucleotide sequence of a GRA2-encoding polynucleotide molecule of the present invention. The term "homologous" when used to refer to a GRA2-related polynucleotide molecule means a polynucleotide molecule having a nucleotide sequence: (a) that encodes the same protein as one of the aforementioned GRA2-encoding polynucleotide molecules of the present invention, but that includes one or more silent changes to the nucleotide sequence according to the degeneracy of the genetic code; or (b) that hybridizes to the complement of a polynucleotide molecule having a nucleotide sequence that encodes the amino acid sequence of the *N. caninum* GRA2 protein, under moderately stringent conditions, i.e., hybridization to filter-bound DNA in 0.5 M NaHPO$_4$, 7% SDS, 1 mM EDTA at 65° C., and washing in 0.2xSSC/0.1% SDS at 42° C. (Ausubel et aL, 1989, above), and that is useful in practicing the present invention, as usefulness is defined above for polynucleotide molecules. In a preferred embodiment, the homologous polynucleotide molecule hybridizes to the complement of a polynucleotide molecule having a nucleotide sequence that encodes the amino acid sequence of the *N. caninum* GRA2 protein under highly stringent conditions, i.e., hybridization to filter-bound DNA in 0.5 M NaHPO$_4$, 7% SDS, 1 mM EDTA at 65° C., and washing in 0.1xSSC/ 0.1% SDS at68° C. (Ausubel etal., 1989, above), and is useful in practicing the present invention. In a more preferred embodiment, the homologous polynucleotide molecule hybridizes under highly stringent conditions to the complement of a polynucleotide molecule consisting of the nucleotide sequence of the ORF of SEQ ID NO:4, which is from about nt 25 to about nt 660, and is useful in practicing the present invention.

Polynucleotide molecules of the present invention having nucleotide sequences that are homologous to the nucleotide sequence of a GRA2-encoding polynucleotide molecule of the present invention do not include polynucleotide molecules having the native nucleotide sequence of T. gondii encoding a T. gondii GRA protein, and further have no more than about 90%, and preferably no more than about 80%, sequence identity to such a T gondii polynucleotide molecule, wherein sequence identity is determined by use of the BLASTN algorithm (GenBank, NCBI).

The present invention further provides an isolated polynucleotide molecule comprising a nucleotide sequence that encodes a polypeptide that is homologous to the N. caninum GRA2 protein. As used herein to refer to polypeptides that are homologous to the N. caninum GRA2 protein, the term "homologous" refers to a polypeptide otherwise having the amino acid sequence of the N. caninum GRA2 protein, but in which one or more amino acid residues have been conservatively substituted with a different amino acid residue, as defined above, where the resulting polypeptide is useful in practicing the present invention, as.usefulness is defined above for polypeptides. In a preferred embodiment, the homologous polypeptide has at least about 70%, more preferably at least about 80%, and most preferably at least about 90% sequence identity to SEQ ID NO:5.

The present invention further provides a polynucleotide molecule consisting of a substantial portion of any of the aforementioned Neospora GRA2-related polynucleotide molecules of the present invention. As used herein, a "substantial portion" of a GRA2-related polynucleotide molecule means a polynucleotide molecule consisting of less than the complete nucleotide sequence of the GRA2-related polynucleotide molecule, but comprising at least about 5%, more preferably at least about 10%, and most preferably at least about 20%, of the nucleotide sequence of the GRA2-related polynucleotide molecule, and that is useful in practicing the present invention, as usefulness is defined above for polynucleotide molecules.

In addition to the nucleotide sequences of any of the aforementioned GRA2-related polynucleotide molecules, polynucleotide molecules of the present invention can further comprise, or alternatively may consist of, nucleotide sequences that naturally flank the GRA2 gene or ORF in situ in N. caninum, and include the flanking nucleotide sequences shown in SEQ ID NO:4 from about nt 1 to about nt 24, and from about nt 661 to about nt 1031, or substantial portions thereof.

4.1.3. SAG1-Related Polynucleotide Molecules

References herein below to the nucleotide sequence shown in SEQ ID NO:6, and to substantial portions thereof, are intended to also refer to the corresponding nucleotide sequence and substantial portions thereof, respectively, as present in plasmid pRC102 (ATCC 209687), unless otherwise indicated. In addition, references herein below to the amino acid sequence shown in SEQ ID NO:7, and to substantial portions and peptide fragments thereof, are intended to also refer to the corresponding amino acid sequence, and substantial portions and peptide fragments thereof, respectively, encoded by the corresponding SAG1-encoding nucleotide sequence present in plasmid pRC102 (ATCC 209687), unless otherwise indicated.

The present invention further provides an isolated polynucleotide molecule comprising a nucleotide sequence encoding the SAG1 protein from N. caninum. In a preferred embodiment, the SAG1 protein has the amino acid sequence of SEQ ID NO:7. In a further preferred embodiment, the isolated SAG1-encoding polynucleotide molecule of the present invention comprises a nucleotide sequence selected from the group consisting of the nucleotide sequence of the ORF of SEQ ID NO:6, which is from about nt 130 to about nt 1089, and the nucleotide sequence of the SAG1-encoding ORF of plasmid pRC102 (ATCC 209687). In a non-limiting embodiment, the isolated SAG1-encoding polynucleotide molecule of the present invention comprises the nucleotide sequence of SEQ ID NO:6.

The present invention further provides an isolated polynucleotide molecule having a nucleotide sequence that is homologous to the nucleotide sequence of a SAG1-encoding polynucleotide molecule of the present invention. The term "homologous" when used to refer to a SAG1-related polynucleotide molecule means a polynucleotide molecule having a nucleotide sequence: (a) that encodes the same protein as one of the aforementioned SAG1-encoding polynucleotide molecules of the present invention, but that includes one or more silent changes to the nucleotide sequence according to the degeneracy of the genetic code; or (b) that hybridizes to the complement of a polynucleotide molecule having a nucleotide sequence that encodes the amino acid sequence of the N. caninum SAG1 protein, under moderately stringent conditions, i.e., hybridization to filter-bound DNA in 0.5 M NaHPO$_4$, 7% SDS, 1 mM EDTA at 65° C., and washing in 0.2×SSC/0.1% SDS at 42° C. (Ausubel et al., 1989, above), and that is useful in practicing the present invention, as usefulness is defined above for polynucleotide molecules. In a preferred embodiment, the homologous polynucleotide molecule hybridizes to the complement of a polynucleotide molecule having a nucleotide sequence that encodes the amino acid sequence of the N. caninum SAG1 protein under highly stringent conditions, i.e., hybridization to filter-bound DNA in 0.5 M NaHPO$_4$, 7% SDS, 1 mM EDTA at 65° C., and washing in 0.1×SSC/0.1% SDS at 68° C. (Ausubel etal., 1989, above), and is useful in practicing the present invention. In a more preferred embodiment, the homologous polynucleotide molecule hybridizes under highly stringent conditions to the complement of a polynucleotide molecule consisting of the nucleotide sequence of the ORF of SEQ ID NO:6, which is from about nt 130 to about nt 1089, and is useful in practicing the present invention.

Polynucleotide molecules of the present invention having nucleotide sequences that are homologous to the nucleotide sequence of a SAG1-encoding polynucleotide molecule of the present invention do not include polynucleotide molecules having the native nucleotide sequence of T. gondii encoding a T. gondii SAG1 protein, and further have no more than about 90%, and preferably no more than about 80%, sequence identity to such a T. gondii polynucleotide molecule, wherein sequence identity is determined by use of the BLASTN algorithm (GenBank, NCBI).

The present invention further provides an isolated polynucleotide molecule comprising a nucleotide sequence that encodes a polypeptide that is homologous to the N. caninum SAG1 protein. As used herein to refer to polypeptides that are homologous to the N. caninum SAG1 protein, the term "homologous" refers to a polypeptide otherwise having the amino acid sequence of the N. caninum SAG1 protein, but in which one or more amino acid residues have been conservatively substituted with a different amino acid residue, as defined above, where the resulting polypeptide is useful in practicing the present invention, as usefulness is defined above for polypeptides. In a preferred embodiment, the homologous polypeptide has at least about 70%, more preferably at least about 80%, and most preferably at least about 90% sequence identity to SEQ ID NO:7.

The present invention further provides a polynucleotide molecule consisting of a substantial portion of any of the aforementioned Neospora SAG1-related polynucleotide molecules of the present invention. As used herein, a "substantial portion" of a SAG1-related polynucleotide molecule means a polynucleotide molecule consisting of less than the complete nucleotide sequence of the SAG1-related polynucleotide molecule, but comprising at least about 5%, more preferably at least about 10%, and most preferably at least about 20%, of the nucleotide sequence of the SAG1-related polynucleotide molecule, and that is useful in practicing the present invention, as usefulness is defined above for polynucleotide molecules.

In addition to the nucleotide sequences of any of the aforementioned SAG1-related polynucleotide molecules, polynucleotide molecules of the present invention can further comprise, or alternatively may consist of, nucleotide sequences that naturally flank the SAG1 gene or ORF in situ in N. caninum, and include the flanking nucleotide sequences shown in SEQ ID NO:6 from about nt 1 to about nt 129 and from about nt 1090 to about nt 1263, or substantial portions thereof.

4.1.4. MIC1-Related Polynucleotide Molecules

References herein below to the nucleotide sequences shown in SEQ ID NOS:8 and 10, and to substantial portions thereof, are intended to also refer to the corresponding nucleotide sequences and substantial portions thereof, respectively, as present in plasmid pRC340 (ATCC 209688), unless otherwise indicated. In addition, references herein below to the amino acid sequences shown in SEQ ID NO:9, and to substantial portions and peptide fragments thereof, are intended to also refer to the corresponding amino acid sequences, and substantial portions and peptide fragments thereof, respectively, encoded by the corresponding MIC1-encoding nucleotide sequence present in plasmid pRC340 (ATCC 209688), unless otherwise indicated.

The present invention further provides an isolated polynucleotide molecule comprising a nucleotide sequence encoding the MIC1 protein from N. caninum. In a preferred embodiment, the MIC1 protein has the amino acid sequence of SEQ ID NO:9. In a further preferred embodiment, the isolated MIC1-encoding polynucleotide molecule of the present invention comprises a nucleotide sequence selected from the group consisting of the nucleotide sequence of the ORF of SEQ ID NO:8, which is from about nt 138 to about nt 1520, the nucleotide sequence of the ORF of the MIC1 gene, which is presented as SEQ ID NO:10, and the nucleotide sequence of the MIC1-encoding ORF of plasmid pRC340 (ATCC 209688). In a non-limiting embodiment, the isolated MIC1-encoding polynucleotide molecule of the present invention comprises a nucleotide sequence selected from the group consisting of the nucleotide sequence of SEQ ID NO:8 and SEQ ID NO:10.

The present invention further provides an isolated polynucleotide molecule having a nucleotide sequence that is homologous to the nucleotide sequence of a MIC1-encoding polynucleotide molecule of the present invention. The term "homologous" when used to refer to a MIC1-related polynucleotide molecule means a polynucleotide molecule having a nucleotide sequence: (a) that encodes the same protein as one of the aforementioned MIC1-encoding polynucleotide molecules of the present invention, but that includes one or more silent changes to the nucleotide sequence according to the degeneracy of the genetic code; or (b) that hybridizes to the complement of a polynucleotide molecule having a nucleotide sequence that encodes the amino acid sequence of the N. caninum MIC1 protein, under moderately stringent conditions, i.e., hybridization to filter-bound DNA in 0.5 M NaHPO$_4$, 7% SDS, 1 mM EDTA at 65° C., and washing in 0.2×SSC/0.1% SDS at 42° C. (Ausubel et al., 1989, above), and that is useful in practicing the present invention, as usefulness is defined above for polynucleotide molecules. In a preferred embodiment, the homologous polynucleotide molecule hybridizes to the complement of a polynucleotide molecule having a nucleotide sequence that encodes the amino acid sequence of the N. caninum MIC1 protein under highly stringent conditions, i.e., hybridization to filter-bound DNA in 0.5 M NaHPO$_4$, 7% SDS, 1 mM EDTA at 65° C., and washing in 0.1 ×SSC/0.1 % SDS at 68° C. (Ausubel et al., 1989, above), and is useful in practicing the present invention. In a more preferred embodiment, the homologous polynucleotide molecule hybridizes under highly stringent conditions to the complement of a polynucleotide molecule consisting of a nucleotide sequence selected from the group consisting of the ORF of SEQ ID NO:8 from about nt 138 to about nt 1520, and the ORF of the MIC1 gene, which is presented as SEQ ID NO:10, and is useful in practicing the present invention.

Polynucleotide molecules of the present invention having nucleotide sequences that are homologous to the nucleotide sequence of a MIC1-encoding polynucleotide molecule of the present invention do not include polynucleotide molecules having the native nucleotide sequence of T. gondii encoding a T. gondii MIC1 protein, and further have no more than about 90%, and preferably no more than about 80%, sequence identity to such a T. gondii polynucleotide molecule, wherein sequence identity is determined by use of the BLASTN algorithm (GenBank, NCBI).

The present invention further provides an isolated polynucleotide molecule comprising a nucleotide sequence that encodes a polypeptide that is homologous to the N. caninum MIC1 protein. As used herein to refer to polypeptides that are homologous to the N. caninum MIC1 protein, the term "homologous" refers to a polypeptide otherwise having the amino acid sequence of the N. caninum MIC1 protein, but in which one or more amino acid residues have been conservatively substituted with a different amino acid residue, as defined above, where the resulting polypeptide is useful in practicing the present invention, as usefulness is defined above for polypeptides. In a preferred embodiment, the homologous polypeptide has at least about 70%, more preferably at least about 80%, and most preferably at least about 90% sequence identity to SEQ ID NO:9.

The present invention further provides a polynucleotide molecule consisting of a substantial portion of any of the aforementioned Neospora MIC1-related polynucleotide molecules of the present invention. As used herein, a "substantial portion" of a MIC1-related polynucleotide molecule means a polynucleotide molecule consisting of less than the complete nucleotide sequence of the MIC1-related polynucleotide molecule, but comprising at least about 5%, more preferably at least about 10%, and most preferably at least about 20%, of the nucleotide sequence of the MIC1-related polynucleotide molecule, and that is useful in practicing the present invention, as usefulness is defined above for polynucleotide molecules.

In addition to the nucleotide sequences of any of the aforementioned MIC1-related polynucleotide molecules, polynucleotide molecules of the present invention can further comprise, or alternatively may consist of, nucleotide sequences that naturally flank the MIC1 ORF or gene in situ in *N. caninum*, and include the nucleotide sequences as shown in SEQ ID NO:8 from about nt 1 to about 137, and from about nt 1521 to about nt 2069, or substantial portions thereof.

4.1.5. MAG1-Related Polynucleotide Molecules

References herein below to the nucleotide sequence shown in SEQ ID NO:11, and to substantial portions thereof, are intended to also refer to the corresponding nucleotide sequences and substantial portions thereof, respectively, as present in plasmid bd304 (ATCC 203413), unless otherwise indicated. In addition, references herein below to the amino acid sequence shown in SEQ ID NO:13, and to substantial portions and peptide fragments thereof, are intended to also refer to the corresponding amino acid sequence, and substantial portions and peptide fragments thereof, respectively, encoded by the corresponding MAG1-encoding nucleotide sequence present in plasmid bd304 (ATCC 203413), unless otherwise indicated.

The present invention further provides an isolated polynucleotide molecule comprising a nucleotide sequence encoding the MAG1 protein from *N. caninum*. In a preferred embodiment, the MAG1 protein has the amino acid sequence of SEQ ID NO:13. In a further preferred embodiment, the isolated MAG1-encoding polynucleotide molecule of the present invention comprises a nucleotide sequence selected from the group consisting of the nucleotide sequence presented in SEQ ID NO:11 from about nt 1305 to about nt 2786, a cDNA molecule prepared therefrom, such as a cDNA molecule having the ORF of SEQ ID NO:12 from about nt 122 to about nt 1381, and the nucleotide sequence of the MAG1-encoding ORF present in plasmid bd304 (ATCC 203413). The present invention further provides a polynucleotide molecule having a nucleotide sequence of any ORF present in SEQ ID NO:11. In a non-limiting embodiment, the isolated MAG1-encoding polynucleotide molecule of the present invention comprises a nucleotide sequence selected from the group consisting of the nucleotide sequence of SEQ ID NO:11 and a cDNA deduced therefrom based on the putative exon/intron boundaries.

The present invention further provides an isolated polynucleotide molecule having a nucleotide sequence that is homologous to the nucleotide sequence of a MAG1-encoding polynucleotide molecule of the present invention. The term "homologous" when used to refer to a MAG1-related polynucleotide molecule means a polynucleotide molecule having a nucleotide sequence: (a) that encodes the same protein as one of the aforementioned MAG1-encoding polynucleotide molecules of the present invention, but that includes one or more silent changes to the nucleotide sequence according to the degeneracy of the genetic code; or (b) that hybridizes to the complement of a polynucleotide molecule having a nucleotide sequence that encodes the amino acid sequence of the *N. caninum* MAG1 protein, under moderately stringent conditions, i.e., hybridization to filter-bound DNA in 0.5 M NaHPO$_4$, 7% SDS, 1 mM EDTA at 65° C., and washing in 0.2×SSC/0.1% SDS at 42° C. (Ausubel et al., 1989, above), and that is useful in practicing the present invention, as usefulness is defined above for polynucleotide molecules. In a preferred embodiment, the homologous polynucleotide molecule hybridizes to the complement of a polynucleotide molecule having a nucleotide sequence that encodes the amino acid sequence of the *N. caninum* MAG1 protein under highly stringent conditions, i.e., hybridization to filter-bound DNA in 0.5 M NaHPO$_4$, 7% SDS, 1 mM EDTA at 65° C., and washing in 0.1×SSC/0.1 % SDS at 68° C. (Ausubel et al., 1989, above), and is useful in practicing the present invention. In a more preferred embodiment, the homologous polynucleotide molecule hybridizes under highly stringent conditions to the complement of a polynucleotide molecule consisting of a nucleotide sequence selected from the group consisting of the nucleotide sequence of the ORF of the MAG1 gene, which is presented in SEQ ID NO:11 from about nt 1305 to about nt 2786 and a cDNA molecule prepared therefrom based on the putative exon/intron boundaries, such as a cDNA molecule having the ORF of SEQ ID NO:12 from about nt 122 to about nt 1381, and is useful in practicing the present invention.

Polynucleotide molecules of the present invention having nucleotide sequences that are homologous to the nucleotide sequence of a MAG1-encoding polynucleotide molecule of the present invention do not include polynucleotide molecules having the native nucleotide sequence of *T. gondii* encoding a *T. gondii* MAG1 protein, and further have no more than about 90%, and preferably no more than about 80%, sequence identity to such a *T. gondii* polynucleotide molecule, wherein sequence identity is determined by use of the BLASTN algorithm (GenBank, NCBI).

The present invention further provides an isolated polynucleotide molecule comprising a nucleotide sequence that encodes a polypeptide that is homologous to the *N. caninum* MAG1 protein. As used herein to refer to polypeptides that are homologous to the *N. caninum* MAG1 protein, the term "homologous" refers to a polypeptide otherwise having the amino acid sequence of the *N. caninum* MAG1 protein, but in which one or more amino acid residues have been conservatively substituted with a different amino acid residue, as defined above, where the resulting polypeptide is useful in practicing the present invention, as usefulness is defined above for polypeptides. In a preferred embodiment, the homologous polypeptide has at least about 70%, more preferably at least about 80%, and most preferably at least about 90% sequence identity to SEQ ID NO:13.

The present invention further provides a polynucleotide molecule consisting of a substantial portion of any of the aforementioned Neospora MAG1-related polynucleotide molecules of the present invention. As used herein, a "substantial portion" of a MAG1-related polynucleotide molecule means a polynucleotide molecule consisting of less than the complete nucleotide sequence of the MAG1-related polynucleotide molecule, but comprising at least about 5%, more preferably at least about 10%, and most preferably at least about 20%, of the nucleotide sequence of the MAG1-related polynucleotide molecule, and that is useful in practicing the present invention, as usefulness is defined above for polynucleotide molecules. For example, a substantial portion of the polynucleotide molecule of SEQ ID NO:11 can comprise putative exon 1 from about nt 704 to about nt 820, or putative exon 2 from about nt 1301 to about nt 1399, or putative exon 3 from about nt 1510 to about nt 1808, or putative exon 4 from about nt 1921 to about nt 3297.

In addition to the nucleotide sequences of any of the aforementioned MAG1-related polynucleotide molecules, polynucleotide molecules of the present invention can further comprise, or alternatively may consist of, nucleotide sequences that naturally flank the MAG1 gene or ORF in situ in *N. caninum*, and include the nucleotide sequences as shown in SEQ ID NO:11 from about nt 1 to about nt 1304, and from about nt 2787 to about nt 4242, or that naturally flank the ORF of a cDNA molecule prepared therefrom based on the putative exon/intron boundaries, and include flanking sequences of the ORF of a cDNA molecule having the ORF of SEQ ID NO:12, from about nt 1 to about nt 121, and from about nt 1382 to about nt 1892, or substantial portions thereof.

4.2. Gra1Mag1 Promoter Region

The present invention further provides a polynucleotide molecule comprising the nucleotide sequence of the *N. caninum* GRA1 and MAG1 gene promoters. During the conduct of the experimental work disclosed herein, it was determined that the *N. caninum* GRA1 and MAG1 genes disclosed herein are naturally arranged in situ in a head-to-head orientation with an intervening nucleotide sequence of about 577 nt in length. This intervening nucleotide sequence, which is presented in SEQ ID NO:11 from nt 127 to nt 703, represents a putative bidirectional promoter region comprising the promoters of both the *N. caninum* GRA1 and MAG1 genes.

The GRA1lMAG1 bidirectional promoter region of the present invention, and functional portions thereof, are useful for a variety of purposes including for controlling the recombinant expression of either the GRA1 or MAG1 genes, or both genes, or of one or more other genes or coding sequences, in host cells of *N. caninum* or in host cells of any other species of Neospora or other member of the Apicomplexa, or in any other appropriate host cell. Such other genes or coding sequences can either be native or heterologous to the recombinant host cell. The promoter sequence can be fused to the particular gene or coding sequence using standard recombinant techniques as known in the art so that the promoter sequence is in operative association therewith, as "operative association" is defined below. By using the promoter, recombinant expression systems can be constructed and used to screen for compounds and transcriptional factors that can modulate the expression of the GRA1 and MAG1 genes of Neospora or other members of the Apicomplexa. In addition, such promoter constructs can be used to express heterologous polypeptides in Neospora or other members of the Apicomplexa.

4.3. Oligonucleotide Molecules

The present invention further provides oligonucleotide molecules that hybridize to any one of the aforementioned polynucleotide molecules of the present invention, or that hybridize to a polynucleotide molecule having a nucleotide sequence that is the complement of any one of the aforementioned polynucleotide molecules of the present invention. Such oligonucleotide molecules are preferably at least about 10 nucleotides in length, and more preferably from about 15 to about 30 nucleotides in length, and hybridize to one or more of the aforementioned polynucleotide molecules under highly stringent conditions, i.e., washing in 6×SSC/0.5% sodium pyrophosphate at about 37° C. for ~14-base oligos, at about 48° C. for ~17-base oligos, at about 55° C. for ~20-base oligos, and at about 60° C. for ~23-base oligos. Other hybridization conditions for longer oligonucleotide molecules of the present invention can be determined by the skilled artisan using standard techniques. In a preferred embodiment, an oligonucleotide molecule of the present invention is complementary to a portion of at least one of the aforementioned polynucleotide molecules of the present invention.

Specific though non-limiting embodiments of oligonucleotide molecules useful in practicing the present invention include oligonucleotide molecules selected from the group consisting of SEQ ID NOS:14–26 and 28–34, and the complements thereof.

The oligonucleotide molecules of the present invention are useful for a variety of purposes, including as primers in amplification of a Neospora-specific polynucleotide molecule for use, e.g., in differential disease diagnosis, or to encode or act as antisense molecules useful in gene regulation. Regarding diagnostics, suitably designed primers can be used to detect the presence of Neospora-specific polynucleotide molecules in a sample of animal tissue or fluid, such as brain tissue, lung tissue, placental tissue, blood, cerebrospinal fluid, mucous, urine, amniotic fluid, etc. The production of a specific amplification product can support a diagnosis of Neospora infection, while lack of an amplified product can point to a lack of infection. Methods for conducting amplifications, such as the polymerase chain reaction (PCR), are described, among other places, in Innis et al. (eds), 1995, above; and Erlich (ed), 1992, above. Other amplification techniques known in the art, e.g., the ligase chain reaction, can alternatively be used. The sequences of the polynucleotide molecules disclosed herein can also be used to design primers for use in isolating homologous genes from other species or strains of Neospora or other members of the Apicomplexa.

4.4. Recombinant Expression Systems

4.4.1. Cloning And Expression Vectors

The present invention further provides compositions for cloning and expressing any of the polynucleotide molecules of.the present invention, including cloning vectors, expression vectors, transformed host cells comprising any of said vectors, and novel strains or cell lines derived therefrom. In a preferred embodiment, the present invention provides a recombinant vector comprising a polynucleotide molecule having a nucleotide sequence encoding the GRA1, GRA2, SAG1, MIC1 or MAG1 protein of *N. caninum*. In specific though non-limiting embodiments, the present invention provides plasmid pRC77 (ATCC 209685), which encodes the *N. caninum* GRA1 protein; plasmid pRC5 (ATCC 209686), which encodes the *N. caninum* GRA2 protein; plasmid pRC102 (ATCC 209687), which encodes the *N. caninum* SAG1 protein; plasmid pRC340 (ATCC 209688), which encodes the *N. caninum* MIC1 protein; and plasmid bd304 (ATCC 203413), which encodes the *N. caninum* MAG1 protein, and which also comprises the bidirectional promoter region described above.

Recombinant vectors of the present invention, particularly expression vectors, are preferably constructed so that the coding sequence for the polynucleotide molecule of the invention is in operative association with one or more regulatory elements necessary for transcription and translation of the coding sequence to produce a polypeptide. As used herein, the term "regulatory element" includes but is not limited to nucleotide sequences that encode inducible and non-inducible promoters, enhancers, operators and other elements known in the art that serve to drive and/or regulate expression of polynucleotide coding sequences. Also, as used herein, the coding sequence is in "operative association" with one or more regulatory elements where the regulatory elements effectively regulate and allow for the transcription of the coding sequence or the translation of its mRNA, or both.

Methods are well-known in the art for constructing recombinant vectors containing particular coding sequences in operative association with appropriate regulatory elements, and these can be used to practice the present invention. These methods include in vitro recombinant techniques, synthetic techniques, and in vivo genetic recombination. See, e.g., the techniques described in Maniatis et al., 1989, above; Ausubel et al., 1989, above; Sambrook et al., 1989, above; Innis et al., 1995, above; and Erlich, 1992, above.

A variety of expression vectors are known in the art which can be utilized to express the GRA1, GRA2, SAG1, MIC1, and MAG1 coding sequences of the present invention, including recombinant bacteriophage DNA, plasmid DNA, and cosmid DNA expression vectors containing the particular coding sequences. Typical prokaryotic expression vector plasmids that can be engineered to contain a polynucleotide molecule of the present invention include pUC8, pUC9, pBR322 and pBR329 (Biorad Laboratories, Richmond, Calif.), pPL and pKK223 (Pharmacia, Piscataway, N.J.), pQE50 (Qiagen, Chatsworth, Calif.), and pGEM-T EASY (Promega, Madison, Wis.), among many others. Typical eukaryotic expression vectors that can be engineered to contain a polynucleotide molecule of the present invention include an ecdysone-inducible mammalian expression system (Invitrogen, Carlsbad, Calif.), cytomegalovirus promoter-enhancer-based systems (Promega, Madison, Wis.; Stratagene, La Jolla, Calif.; Invitrogen), and baculovirus-based expression systems (Promega), among others.

The regulatory elements of these and other vectors can vary in their strength and specificities. Depending on the host/vector system utilized, any of a number of suitable transcription and translation elements can be used. For instance, when cloning in mammalian cell systems, promoters isolated from the genome of mammalian cells, e.g., mouse metallothionein promoter, or from viruses that grow in these cells, e.g., vaccinia virus 7.5 K promoter or Moloney murine sarcoma virus long terminal repeat, can be used. Promoters obtained by recombinant DNA or synthetic techniques can also be used to provide for transcription of the inserted sequence. In addition, expression from certain promoters can be elevated in the presence of particular inducers, e.g., zinc and cadmium ions for metallothionein promoters. Non-limiting examples of transcriptional regulatory regions or promoters include for bacteria, the β-gal promoter, the T7 promoter, the TAC promoter, λ left and right promoters, trp and lac promoters, trp-lac fusion promoters, etc.; for yeast, glycolytic enzyme promoters, such as ADH-II and -II promoters, GPK promoter, PGI promoter, TRP promoter, etc.; and for mammalian cells, SV40 early and late promoters, adenovirus major late promoters, among others. The present invention further provides a polynucleotide molecule comprising the nucleotide sequence of the promoters of both the GRA1 and MAG1 genes of N. caninum, which can be used to express any of the coding sequences of the present invention in Neospora or other members of the Apicomplexa.

Specific initiation signals are also required for sufficient translation of inserted coding sequences. These signals typically include an ATG initiation codon and adjacent sequences. In cases where the polynucleotide molecule of the present invention including its own initiation codon and adjacent sequences are inserted into the appropriate expression vector, no additional translation control signals may be needed. However, in cases where only a portion of a coding sequence is inserted, exogenous translational control signals, including the ATG initiation codon, may be required. These exogenous translational control signals and initiation codons can be obtained from a variety of sources, both natural and synthetic. Furthermore, the initiation codon must be in phase with the reading frame of the coding regions to ensure in- frame translation of the entire insert.

Expression vectors can also be constructed that will express a fusion protein comprising a protein or polypeptide of the present invention. Such fusion proteins can be used, e.g., to raise antisera against a Neospora protein, to study the biochemical properties of the Neospora protein, to engineer a Neospora protein exhibiting different immunological or functional properties, or to aid in the identification or purification, or to improve the stability, of a recombinantly-expressed Neospora protein. Possible fusion protein expression vectors include but are not limited to vectors incorporating sequences that encode β-galactosidase and trpE fusions, maltose-binding protein fusions, glutathione-S-transferase fusions and polyhistidine fusions (carrier regions). Methods are well-known in the art that can be used to construct expression vectors encoding these and other fusion proteins.

The fusion protein can be useful to aid in purification of the expressed protein. In non-limiting embodiments, e.g., a GRA1-maltose-binding fusion protein can be purified using amylose resin; a GRA1-glutathione-S-transferase fusion protein can be purified using glutathione-agarose beads; and a GRA1-polyhistidine fusion protein can be purified using divalent nickel resin. Alternatively, antibodies against a carrier protein or peptide can be used for affinity chromatography purification of the fusion protein. For example, a nucleotide sequence coding for the target epitope of a monoclonal antibody can be engineered into the expression vector in operative association with the regulatory elements and situated so that the expressed epitope is fused to a Neospora protein of the present invention. In a non-limiting embodiment, a nucleotide sequence coding for the FLAG™ epitope tag (International Biotechnologies Inc.), which is a hydrophilic marker peptide, can be inserted by standard techniques into the expression vector at a point corresponding, e.g., to the amino or carboxyl terminus of the GRA1 protein. The expressed GRA1 protein-FLAG™ epitope fusion product can then be detected and affinity-purified using commercially available anti-FLAG™ antibodies.

The expression vector can also be engineered to contain polylinker sequences that encode specific protease cleavage sites so that the expressed Neospora protein can be released from the carrier region or fusion partner by treatment with a specific protease. For example, the fusion protein vector can include a nucleotide sequence encoding a thrombin or factor Xa cleavage site, among others.

A signal sequence upstream from and in reading frame with the Neospora coding sequence can be engineered into the expression vector by known methods to direct the trafficking and secretion of the expressed protein. Non-limiting examples of signal sequences include those from α-factor, immunoglobulins, outer membrane proteins, penicillinase, and T-cell receptors, among others.

To aid in the selection of host cells transformed or transfected with a recombinant vector of the present invention, the vector can be engineered to further comprise a coding sequence for a reporter gene product or other selectable marker. Such a coding sequence is preferably in operative association with the regulatory elements, as described above. Reporter genes that are useful in practicing the invention are well-known in the art and include those encoding chloramphenicol acetyltransferase (CAT), green fluorescent protein, firefly luciferase, and human growth hormone, among others. Nucleotide sequences encoding selectable markers are well-known in the art, and include those that encode gene products conferring resistance to antibiotics or anti-metabolites, or that supply an auxotrophic requirement. Examples of such sequences include those that encode thymidine kinase activity, or resistance to methotrexate, ampicillin, kanamycin, chloramphenicol, zeocin, pyrimethamine, aminoglycosides, or hygromycin, among others.

4.4.2. Transformation Of Host Cells

The present invention further provides transformed host cells comprising a polynucleotide molecule or recombinant vector of the present invention, and cell lines derived therefrom. Host cells useful in practicing the invention can be eukaryotic or prokaryotic cells. Such transformed host cells include but are not limited to microorganisms, such as bacteria transformed with recombinant bacteriophage DNA, plasmid DNA or cosmid DNA vectors, or yeast transformed with a recombinant vector, or animal cells, such as insect cells infected with a recombinant virus vector, e.g., baculovirus, or mammalian cells infected with a recombinant virus vector, e.g., adenovirus or vaccinia virus, among others. For example, a strain of E. coli can be used, such as, e.g., the DH5α strain available from the ATCC, Rockville, Md., USA (Accession No. 31343), or from Stratagene (La Jolla, Calif.). Eukaryotic host cells include yeast cells, although mammalian cells, e.g., from a mouse, hamster, cow, monkey, or human cell line, among others, can also be utilized effectively. Examples of eukaryotic host cells that can be used to express a recombinant protein of the invention include Chinese hamster ovary (CHO) cells (e.g., ATCC Accession No. CCL-61), NIH Swiss mouse embryo cells NIH/3T3 (e.g., ATCC Accession No. CRL-1658), and Madin-Darby bovine kidney (MDBK) cells (ATCC Accession No. CCL-22).

The recombinant vector of the invention is preferably transformed or transfected into one or more host cells of a substantially homogeneous culture of cells. The vector is generally introduced into host cells in accordance with known techniques, such as, e.g., by protoplast transformation, calcium phosphate precipitation, calcium chloride treatment, microinjection, electroporation, transfection by contact with a recombined virus, liposome-mediated transfection, DEAE-dextran transfection, transduction, conjugation, or microprojectile bombardment, among others. Selection of transformants can be conducted by standard procedures, such as by selecting for cells expressing a selectable marker, e.g., antibiotic resistance, associated with the recombinant expression vector.

Once an expression vector is introduced into the host cell, the integration and maintenance of the polynucleotide molecule of the present invention, either in the host cell genome or episomally, can be confirmed by standard techniques, e.g., by Southern hybridization analysis, restriction enzyme analysis, PCR analysis including reverse transcriptase PCR (rt-PCR), or by immunological assay to detect the expected protein product. Host cells containing and/or expressing a polynucleotide molecule of the present invention can be identified by any of at least four general approaches that are well-known in the art, including: (i) DNA-DNA, DNA-RNA, or RNA-antisense RNA hybridization; (ii) detecting the presence of "marker" gene functions; (iii) assessing the level of transcription as measured by the expression of specific mRNA transcripts in the host cell; or (iv) detecting the presence of mature polypeptide product, e.g., by immunoassay, as known in the art.

4.4.3. Expression And Purification Of Recombinant Polypeptides

Once a polynucleotide molecule of the present invention has been stably introduced into an appropriate host cell, the transformed host cell is clonally propagated, and the resulting cells are grown under conditions conducive to the maximum production of the encoded polypeptide. Such conditions typically include growing transformed cells to high density. Where the expression vector comprises an inducible promoter, appropriate induction conditions such as, e.g., temperature shift, exhaustion of nutrients, addition of gratuitous inducers (e.g., analogs of carbohydrates, such as isopropyl-β-D-thiogalactopyranoside (IPTG)), accumulation of excess metabolic by-products, or the like, are employed as needed to induce expression.

Where the polypeptide is retained inside the host cells, the cells are harvested and lysed, and the product is substantially purified or isolated from the lysate under extraction conditions known in the art to minimize protein degradation such as, e.g., at 4° C., or in the presence of protease inhibitors, or both. Where the polypeptide is secreted from the host cells, the exhausted nutrient medium can simply be collected and the polypeptide substantially purified or isolated therefrom.

The polypeptide can be substantially purified or isolated from cell lysates or culture medium, as necessary, using standard methods, including but not limited to one or more of the following methods: ammonium sulfate precipitation, size fractionation, ion exchange chromatography, HPLC, density centrifugation, and affinity chromatography. If the polypeptide lacks biological activity, it can. be detected as based, e.g., on size, or reactivity with a polypeptide-specific antibody, or by the presence of a fusion tag. For use in practicing the present invention, the polypeptide can be in an unpurified state as secreted into the culture fluid or as present in a cell lysate, but is preferably substantially purified or isolated therefrom. As used herein, a polypeptide is "substantially purified" where the polypeptide constitutes at least about 20 wt % of the protein in a particular preparation. Also, as used herein, a polypeptide is "isolated" where the polypeptide constitutes at least about 80 wt% of the protein in a particular preparation.

Thus, the present invention provides a substantially purified or isolated polypeptide encoded by a polynucleotide of the present invention. In a non-limiting embodiment, the polypeptide is a N. caninum protein selected from the group consisting of GRA1, GRA2, SAG1, MIC1 and MAG1 proteins. In a preferred embodiment, the N. caninum GRA1 protein has the amino acid sequence of SEQ ID NO:2. In another preferred embodiment, the N. caninum GRA2 protein has the amino acid sequence of SEQ ID NO:5. In another preferred embodiment, the N. caninum SAG1 protein has the amino acid sequence of SEQ ID NO:7. In another preferred embodiment, the N. caninum MIC1 protein has the amino acid sequence of SEQ ID NO:9. In another preferred embodiment, the N. caninum MAG1 protein has the amino acid sequence of SEQ ID NO:13.

The present invention further provides polypeptides that are homologous to any of the aforementioned N. caninum proteins, as the term "homologous" is defined above for polypeptides. Polypeptides of the present invention that are homologous to any of the aforementioned GRA1, GRA2, SAG1, MIC1 or MAG1 proteins of N. caninum do not include polypeptides having the native amino acid sequence of a T. gondii GRA, SAG, MIC or MAG protein, and further have no more than about 90%, and preferably no more than about 80%, amino acid sequence identity to such a T. gondii polypeptide, wherein sequence identity is determined by use of the BLASTP algorithm (GenBank, NCBI).

The present invention further provides polypeptides consisting of a substantial portion of any one of the aforementioned polypeptides of the present invention. As used herein, a "substantial portion" of a polypeptide of the present invention, or "peptide fragment," means a polypeptide consisting of less than the complete amino acid sequence of the corresponding full-length polypeptide, but comprising at least about 10%, and more preferably at least about 20%, of the amino acid sequence thereof, and that is useful in practicing the present invention, as defined above for polypeptides. Particularly preferred are peptide fragments that are immunogenic, i.e., capable of inducing an immune response which results in production of antibodies that react specifically against the corresponding full-length Neospora polypeptide.

The present invention further provides fusion proteins comprising any of the aforementioned polypeptides fused to a carrier or fusion partner as known in the art.

The present invention further provides a method of preparing any of the aforementioned polypeptides, comprising culturing a host cell transformed with a recombinant expression vector, said recombinant expression vector comprising a polynucleotide molecule comprising a nucleotide sequence encoding the particular polypeptide, which polynucleotide molecule is in operative association with one or more regulatory elements, under conditions conducive to the expression of the polypeptide, and recovering the expressed polypeptide from the cell culture.

4.5. Use Of Polypeptides

Once a polypeptide of the present invention of sufficient purity has been obtained, it can be characterized by standard methods, including by SDS-PAGE, size exclusion chromatography, amino acid sequence analysis, immunological activity, biological activity, etc. The polypeptide can be further characterized using hydrophilicity analysis (see, e.g., Hopp and Woods, 1981, Proc. Natl. Acad. Sci. USA 78:3824), or analogous software algorithms, to identify hydrophobic and hydrophilic regions. Structural analysis can be carried out to identify regions of the polypeptide that assume specific secondary structures. Biophysical methods such as X-ray crystallography (Engstrom, 1974, Biochem. Exp. Biol. 11: 7–13), computer modeling (Fletterick and Zoller (eds), 1986, in: *Current Communications in Molecular Biology*, Cold Spring Harbor Laboratory, Cold Spring Harbor, N.Y.), and nuclear magnetic resonance (NMR) can be used to map and study potential sites of interaction between the polypeptide and other putative interacting proteins/receptors/molecules. Information obtained from these studies can be used to design deletion mutants and vaccine compositions, and to design or select therapeutic or pharmacologic compounds that can specifically block the biological function of the polypeptide in vivo.

Polypeptides of the present invention are useful for a variety of purposes, including as components of vaccine compositions to protect mammals against neosporosis; or as diagnostic reagents, e.g., using standard techniques such as ELISA assays, to screen for Neospora-specific antibodies in blood or serum samples from animals; or as antigens to raise polyclonal or monoclonal antibodies, as described below, which antibodies are useful as diagnostic reagents, e.g., using standard techniques such as Western blot assays, to screen for Neospora-specific proteins in cell, tissue or fluid samples from an animal.

4.6. Analogs And Derivatives Of Polypeptides

Any polypeptide of the present invention can be modified at the protein level to improve or otherwise alter its biological or immunological characteristics. One or more chemical modifications of the polypeptide can be carried out using known techniques to prepare analogs therefrom, including but not limited to any of the following: substitution of one or more L-amino acids of the polypeptide with corresponding D-amino acids, amino acid analogs, or amino acid mimics, so as to produce, e.g., carbazates or tertiary centers; or specific chemical modification, such as, e.g., proteolytic cleavage with trypsin, chymotrypsin, papain or V8 protease, or treatment with $NaBH_4$ or cyanogen bromide, or acetylation, formylation, oxidation or reduction, etc. Alternatively or additionally, polypeptides of the present invention can be modified by genetic recombination techniques.

A polypeptide of the present invention can be derivatized by conjugation thereto of one or more chemical groups, including but not limited to acetyl groups, sulfur bridging groups, glycosyl groups, lipids, and phosphates, and/or by conjugation to a second polypeptide of the present invention, or to another protein, such as, e.g., serum albumin, keyhole limpet hemocyanin, or commercially activated BSA, or to a polyamino acid (e.g., polylysine), or to a polysaccharide, (e.g., sepharose, agarose, or modified or unmodified celluloses), among others. Such conjugation is preferably by covalent linkage at amino acid side chains and/or at the N-terminus or C-terminus of the polypeptide. Methods for carrying out such conjugation reactions are well-known in the field of protein chemistry.

Derivatives useful in practicing the claimed invention also include those in which a water-soluble polymer such as, e.g., polyethylene glycol, is conjugated to a polypeptide of the present invention, or to an analog or derivative thereof, thereby providing additional desirable properties while retaining, at least in part, the immunogenicity of the polypeptide. These additional desirable properties include, e.g., increased solubility in aqueous solutions, increased stability in storage, increased resistance to proteolytic degradation, and increased in vivo half-life. Water-soluble polymers suitable for conjugation to a polypeptide of the present invention include but are not limited to polyethylene glycol homopolymers, polypropylene glycol homopolymers, copolymers of ethylene glycol with propylene glycol, wherein said homopolymers and copolymers are unsubstituted or substituted at one end with an alkyl group, polyoxyethylated polyols, polyvinyl alcohol, polysaccharides, polyvinyl ethyl ethers, and $\alpha,\beta$-poly[2-hydroxyethyl]-DL-aspartamide. Polyethylene glycol is particularly preferred. Methods for making water-soluble polymer conjugates of polypeptides are known in the art and are described in, among other places, U.S. Pat. No. 3,788,948; U.S. Pat. No. 3,960,830; U.S. Pat. No. 4,002,531; U.S. Pat. No. 4,055,635; U.S. Pat. No. 4,179,337; U.S. Pat. No. 4,261,973; U.S. Pat. No. 4,412,989; U.S. Pat. No. 4,414,147; U.S. Pat. No. 4,415,665; U.S. Pat. No. 4,609,546; U.S. Pat. No. 4,732,863; U.S. Pat. No. 4,745,180; European Patent (EP) 152,847; EP 98,110; and Japanese Patent 5,792,435, which patents are incorporated herein by reference.

4.7. Antibodies

The present invention further provides isolated antibodies directed against a polypeptide of the present invention. In a preferred embodiment, antibodies can be raised against a GRA1, GRA2, SAG1, MIC1 or MAG1 protein from *N. caninum* using known methods. Various host animals selected from pigs, cows, horses, rabbits, goats, sheep, or mice, can be immunized with a partially or substantially purified, or isolated, *N. caninum* protein, or with a homolog, fusion protein, substantial portion, analog or derivative thereof, as these are described above. An adjuvant, such as described below, can be used to enhance antibody production.

Polyclonal antibodies can be obtained and isolated from the serum of an immunized animal and tested for specificity against the antigen using standard techniques. Alternatively, monoclonal antibodies can be prepared and isolated using any technique that provides for the production of antibody molecules by continuous cell lines in culture. These include but are not limited to the hybridoma technique originally described by Kohler and Milstein (Nature, 1975, 256: 495–497); the human B-cell hybridoma technique (Kosbor et al., 1983, Immunology Today 4:72; Cote et al., 1983, Proc. Natl. Acad. Sci. USA 80: 2026–2030); and the EBV-hybridoma technique (Cole et al., 1985, *Monoclonal Antibodies and Cancer Therapy,* Alan R. Liss, Inc., pp. 77–96). Alternatively, techniques described for the production of single chain antibodies (see, e.g., U.S. Pat. No. 4,946,778) can be adapted to produce N. caninum antigen-specific single chain antibodies. These publications are incorporated herein by reference.

Antibody fragments that contain specific binding sites for a polypeptide of the present invention are also encompassed within the present invention, and can be generated by known techniques. Such fragments include but are not limited to F(ab')$_2$ fragments, which can be generated by pepsin digestion of an intact antibody molecule, and Fab fragments, which can be generated by reducing the disulfide bridges of the F(ab')$_2$ fragments. Alternatively, Fab expression libraries can be constructed (Huse et al., 1989, Science 246: 1275–1281) to allow rapid identification of Fab fragments having the desired specificity to the *N. caninum* protein.

Techniques for the production and isolation of monoclonal antibodies and antibody fragments are well-known in the art, and are additionally described, among other places, in Harlow and Lane, 1988, *Antibodies: A Laboratory Manual,* Cold Spring Harbor Laboratory, and in J. W. Goding, 1986, *Monoclonal Antibodies: Principles and Practice,* Academic Press, London, which are incorporated herein by reference.

4.8. Targeted Mutation Of Neospora Genes

Based on the disclosure of the polynucleotide molecules of the present invention, genetic constructs can be prepared for use in disabling or otherwise mutating a Neospora GRA1, GRA2, SAG1, MIC1 or MAG1 gene (which genes are hereinafter referred to collectively or individually as the "Neospora genes" or a "Neospora gene," respectively). Each of the Neospora genes can be mutated using an appropriately designed genetic construct in combination with genetic techniques now known or to be developed in the future. For example, a Neospora gene can be mutated using a genetic construct of the present invention that functions to: (a) delete all or a portion of the coding sequence or regulatory sequence of the Neospora gene; or (b) replace all or a portion of the coding sequence or regulatory sequence of the Neospora gene with a different nucleotide sequence; or (c) insert into the coding sequence or regulatory sequence of the Neospora gene one or more nucleotides, or an oligonucleotide molecule, or polynucleotide molecule, which can comprise a nucleotide sequence from Neospora or from a heterologous source; or (d) carry out some combination of (a), (b) and (c).

Neospora cells in which a Neospora gene has been mutated are useful in practicing the present invention where mutating the gene reduces the pathogenicity of the Neospora cells carrying the mutated gene compared to cells of the same strain of Neospora where the gene has not been so mutated, and where such Neospora cells carrying the disabled gene can be used in a vaccine composition, particularly in a modified live vaccine, to induce or contribute to the induction of, a protective response in a mammal against neosporosis. In a preferred embodiment, the mutation serves to partially or completely disable the Neospora gene, or partially or completely disable the protein encoded by the Neospora gene. In this context, a Neospora gene or protein is considered to be partially or completely disabled if either no protein product is made (for example, the gene is deleted), or a protein product is made that can no longer carry out its normal biological function or can no longer be transported to its normal cellular location, or a product is made that carries out its normal biological function but at a significantly reduced rate, or if such mutation results in a detectable decrease in the pathogenicity of cells of a pathogenic strain of Neospora wherein the gene has been so mutated compared to cells of the same strain but in which the gene has not be so mutated.

In a non-limiting embodiment, a genetic construct of the present invention is used to mutate a wild-type Neospora gene by replacement of the coding sequence of the wild-type gene, or a promoter or other regulatory region thereof, or a portion thereof, with a different nucleotide sequence such as, e.g., a mutated coding sequence or mutated regulatory region, or portion thereof. Mutated Neospora gene sequences for use in such a genetic construct can be produced by any of a variety of known methods, including by use of error-prone PCR, or by cassette mutagenesis. For example, oligonucleotide-directed mutagenesis can be employed to alter the coding sequence or promoter sequence of a wild-type Neospora gene in a defined way, e.g., to introduce a frame-shift or a termination codon at a specific point within the sequence. Alternatively or additionally, a mutated nucleotide sequence for use in the genetic construct of the present invention can be prepared by insertion into the coding sequence or promoter sequence of one or more nucleotides, oligonucleotide molecules or polynucleotide molecules, or by replacement of a portion of the coding sequence or promoter sequence with one or more different nucleotides, oligonucleotide molecules or polynucleotide molecules. Such oligonucleotide molecules or polynucleotide molecules can be obtained from any naturally occurring source or can be synthetic. The inserted sequence can serve simply to disrupt the reading frame of the Neospora gene, or can further encode a heterologous gene product such as a selectable marker.

Alternatively or additionally, random mutagenesis can be used to produce a mutated Neospora gene sequence for use in a genetic construct of the present invention. Random mutagenesis can be carried out by any techniques now known or to be developed in the future such as, e.g., by exposing cells carrying a Neospora gene to ultraviolet radiation or x-rays, or to chemical mutagens such as N-methyl-N'-nitrosoguanidine, ethyl methane sulfonate, nitrous acid or nitrogen mustards, and then selecting for cells carrying a mutation in the particular gene. See, e.g., Ausubel, 1989, above, for a review of mutagenesis techniques.

Mutations to produce modified Neospora cells that are useful in practicing the present invention, as defined above, can occur anywhere in the Neospora gene, including in the ORF, or in the promoter or other regulatory region, or in any other sequences that naturally comprise the gene or ORF. Such Neospora cells include mutants in which a modified form of the protein normally encoded by the Neospora gene is produced, or in which no protein normally encoded by the Neospora gene is produced, and can be null, conditional or leaky mutants.

Alternatively, a genetic construct of the present invention can comprise nucleotide sequences that naturally flank the Neospora gene or ORF in situ, such as those presented in SEQ ID NOS:1, 3, 4, 6, 8, 10, 11 and 12, with only a portion or no nucleotide sequences from the coding region of the gene itself. Such a genetic construct would be useful, e.g., to delete the entire Neospora gene or ORF.

In a preferred embodiment, a genetic construct of the present invention comprises a polynucleotide molecule that can be used to disable a Neospora gene, comprising: (a) a polynucleotide molecule having a nucleotide sequence that is otherwise the same as a nucleotide sequence encoding a GRA1, GRA2, SAG1, MIC1 or MAG1 protein from *N. caninum*, but which nucleotide sequence further comprises one or more disabling mutations; or (b) a polynucleotide molecule comprising a nucleotide sequence that naturally flanks the ORF of a Neospora gene in situ. Once transformed into cells of a strain of Neospora, the polynucleotide molecule of the genetic construct is specifically targeted to the particular Neospora gene by homologous recombination, and thereby either replaces the gene or portion thereof or inserts into the gene. As a result of this recombination event, the Neospora gene otherwise native to that particular strain of Neospora is disabled.

Methods for carrying out homologous gene replacement in parasitic protozoans are known in the art, and are described, among other places, in Cruz and Beverley, 1990, Nature 348:171–173; Cruz et al., 1991, Proc. Natl. Acad. Sci. USA 88:7170–7174; Donald and Roos, 1994, Mol. Biochem. Parasitol. 63:243–253; and Titus et al., 1995, Proc. Natl. Acad. Sci. USA 92:10267–10271, all of which are incorporated herein by reference.

For targeted gene mutation through homologous recombination, the genetic construct is preferably a plasmid, either circular or linearized, comprising a mutated nucleotide sequence as described above. In a non-limiting embodiment, at least about 200 nucleotides of the mutated sequence are used to specifically direct the genetic construct of the present invention to the particular targeted Neospora gene for homologous recombination, although shorter lengths of nucleotides can also be effective. In addition, the plasmid preferably comprises an additional nucleotide sequence encoding a reporter gene product or other selectable marker that is constructed so that it will insert into the Neospora genome in operative association with the regulatory element sequences of the native Neospora gene to be disrupted. Reporter genes that can be used in practicing the invention are well-known in the art and include those encoding CAT, green fluorescent protein, and β-galactosidase, among others. Nucleotide sequences encoding selectable markers are also well-known in the art, and include those that encode gene products conferring resistance to antibiotics or anti-metabolites, or that supply an auxotrophic requirement. Examples of such sequences include those that encode pyrimethamine resistance, or neomycin phosphotransferase (which confers resistance to aminoglycosides), or hygromycin phosphotransferase (which confers resistance to hygromycin).

Methods that can be used for creating the genetic constructs of the present invention are well-known in the art, and include in vitro recombinant techniques, synthetic techniques, and in vivo genetic recombination, as described, among other places, in Maniatis et al., 1989, above; Ausubel et al., 1989, above; Sambrook et al., 1989, above; Innis et al., 1995, above; and Erlich, 1992, above.

Neospora cells can be transformed or transfected with a genetic construct of the present invention in accordance with known techniques, such as, e.g., by electroporation. Selection of transformants can be carried out using standard techniques, such as by selecting for cells expressing a selectable marker associated with the construct. Identification of transformants in which a successful recombination event has occurred and the particular target gene has been disabled can be carried out by genetic analysis, such as by Southern blot analysis, or by Northern analysis to detect a lack of mRNA transcripts encoding the particular protein, or by the appearance of a novel phenotype, such as reduced pathogenicity, or cells lacking the particular protein, as determined, e.g., by immunological analysis, or some combination thereof.

Neospora cells that can be modified according to the present invention are preferably tachyzoites, but can alternatively be bradyzoites or oocysts. Although cells in certain stages of the Neospora life cycle are diploid, tachyzoites are haploid. Thus, the use of tachyzoites in the production of modified Neospora cells expressing the appropriate mutant phenotype is preferred because tachyzoites require only a single successful recombination event to disrupt the particular Neospora gene. Alternatively, in diploid cells of Neospora, two alleles must be disrupted for each gene. This can be accomplished by sequentially targeting the first allele and then the second allele with genetic constructs bearing two different selectable markers.

In a further non-limiting embodiment, the genetic construct of the present invention can additionally comprise a different gene or coding region from Neospora or from a different pathogen that infects the animal, which gene or coding region encodes an antigen useful to induce, or contribute to the induction of, a separate and distinct protective immune response in the animal upon vaccination with the modified live Neospora cells of the present invention. This additional gene or coding region can be further engineered to contain a signal sequence that leads to secretion of the encoded antigen from the modified live Neospora cell, thereby allowing for the antigen to be displayed to the immune system of the vaccinated animal.

The present invention thus provides modified live Neospora cells in which the GRA1, GRA2, SAG1, MIC1 or MAG1 gene has been mutated. The present invention further provides modified live Neospora cells in which a combination of two or more of the GRA1, GRA2, SAG1, MIC1, and MAG1 genes have been mutated, which cells can be prepared using the general methods presented above. In addition, the present invention provides a method of preparing modified live Neospora cells, comprising: (a) transforming cells of Neospora with a genetic construct of the invention; (b) selecting transformed cells in which the GRA1, GRA2, SAG1, MIC1, or MAG1 gene has been mutated by the genetic construct; and (c) selecting from among the cells of step (b) those cells that can be used in a vaccine to protect a mammal against neosporosis.

4.9. Culturing Neospora Cells

Neospora cells for use in the present invention can be cultured and maintained in vitro by infecting any receptive host cell line, preferably a mammalian cell line, with tachyzoites according to known techniques described in the art. Mammalian cell lines in which tachyzoites of Neospora can be cultured include, e.g., human foreskin fibroblasts (Lindsay et al., 1993, Am. J. Vet. Res. 54:103–106), bovine cardiopulmonary aortic endothelial cells (Marsh et al., 1995, above), bovine monocytes (Lindsay and Dubey, 1989, above), and monkey kidney cells, among others. For example, tachyzoites of N. caninum can be cultured in monolayers of Hs68 human foreskin fibroblast cells (ATCC Accession No. CRL-1635) (Lindsay et al, 1993, above); and MARC145 monkey kidney cells infected with tachyzoites of N. caninum strain NC-1 for use in the present invention are on deposit with the ATCC (Accession No. 12231). Bradyzoites can be similarly cultured and manipulated.

Mammalian cell cultures can be grown, and cell cultures that have been infected with Neospora cells can be maintained, in any of several types of culture media described in the art. For example, stationary monolayer cultures of bovine cardiopulmonary aortic endothelial cells infected with tachyzoites of N. caninum can be grown in Dulbecco's Minimum Essential Medium (DMEM; Gibco Laboratories, N.Y.), supplemented with 10% (v/v) heat-inactivated fetal bovine serum (FBS) or adult equine serum (ES), 2 mM L-glutamine, 50 U/ml penicillin, and 50 $\mu$g/ml streptomycin (Conrad et al., 1993, above). Monolayers of Hs68 human foreskin fibroblast cells can be maintained in RPMI 1640 containing 2% (v/v) FBS, 1.0 mM sodium pyruvate, $1 \times 10^4$ U/ml penicillin, $1 \times 10^4$ $\mu$g/ml streptomycin, $5 \times 10^2$ mM 2-mercaptoethanol and 0.3 mg/ml L-glutamine (maintenance medium). Monolayer cultures of Hs68 human foreskin fibroblast cells infected with Neospora can be maintained in identical media, but in which the FBS is increased to 10% (v/v) (growth medium).

Neospora-infected monolayer cultures of mammalian cells are typically maintained under standard tissue culture conditions such as, e.g., at 37° C. and 5% $CO_2$. Tachyzoites are typically passaged to uninfected monolayer cultures when 70–90% of the mammalian cells in the culture have become infected, which can be determined microscopically using standard techniques. Tachyzoites can be collected from the infected mammalian cell cultures by lysing the host cells using any standard technique and collecting the tachyzoites, e.g., by filtration or by centrifugation.

Modified live Neospora cells of the present invention can also be cultured in mammalian cells, as described above.

4.10. Anti-Neospora Vaccines

The present invention further provides a vaccine against neosporosis, comprising an immunologically effective amount of one or more proteins or polypeptides of the present invention, and a veterinarily acceptable carrier. In a preferred embodiment, the vaccine comprises a N. caninum protein selected from the group consisting of GRA1, GRA2, SAG1, MIC1 and MAG1.

The present invention further provides a vaccine against neosporosis, comprising an immunologically effective amount of one or more polynucleotide molecules of the present invention, and a veterinarily acceptable carrier. In a preferred embodiment, the vaccine comprises a polynucleotide molecule having a nucleotide sequence encoding a N. caninum protein selected from the group consisting of GRA1, GRA2, SAG1, MIC1, and MAG1.

The present invention further provides a vaccine against neosporosis, comprising an immunologically effective amount of modified Neospora cells of the present invention, and a veterinarily acceptable carrier. In a preferred embodiment, the modified Neospora cells for use in the vaccine of the present invention are live cells of N. caninum which express a GRA1, GRA2$^-$, SAG1$^-$, MIC1$^-$, or MAG1$^-$ phenotype. Alternatively, the vaccine of the present invention can comprise any of such modified Neospora cells of the present invention that have been inactivated. Inactivation of modified Neospora cells can be carried out using any techniques known in the art, including by chemical treatment, such as with binary ethylenimine (BEI), or beta-propiolactone, or by freeze-thawing or heat treatment, or by homogenization of cells, or by a combination of these types of techniques. Vaccines prepared from homogenized, modified Neospora cells can consist of either the entire unfractionated cell homogenate, or an immunologically effective subfraction thereof. As used herein, the term "immunologically effective amount" refers to that amount of antigen, e.g., protein, polypeptide, polynucleotide molecule, or modified cells, capable of inducing a protective response against neosporosis when administered to a member of a mammalian species after either a single administration, or after multiple administrations.

The phrase "capable of inducing a protective response" is used broadly herein to include the induction or enhancement of any immune-based response in the animal in response to vaccination, including either an antibody or cell-mediated immune response, or both, that serves to protect the vaccinated animal against neosporosis. The terms "protective response" and "protect" as used herein refer not only to the absolute prevention of neosporosis or absolute prevention of infection by a neosporosis-causing pathogen, but also to any detectable reduction in the degree or rate of infection by such a pathogen, or any detectable reduction in the severity of the disease or any symptom or condition resulting from infection by the pathogen, including, e.g., any detectable reduction in the rate of formation, or in the absolute number, of lesions formed in one or more tissues, or any detectable reduction in the occurrence of abortion, or the transmission of infection from a pregnant mammal to its fetus or from a mammal parent to its offspring, in the vaccinated animal as compared to an unvaccinated infected animal of the same species.

In a further preferred embodiment, the vaccine of the present invention is a combination vaccine for protecting a mammal against neosporosis and, optionally, one or more other diseases or pathological conditions that can afflict the mammal, which combination vaccine comprises an immunologically effective amount of a first component comprising a polypeptide, polynucleotide molecule, or modified Neospora cells of the present invention; an immunologically effective amount of a second component that is different from the first component, and that is capable of inducing, or contributing to the induction of, a protective response against a disease or pathological condition that can afflict the mammal; and a veterinarily acceptable carrier.

The second component of the combination vaccine is selected based on its ability to induce, or contribute to the induction of, a protective response against either neosporosis or another disease or pathological condition that can afflict members of the mammalian species, as known in the art. Any antigenic component now known in the art, or to be determined in the future, to be useful in a vaccine composition in the particular mammalian species can be used as the second component of the combination vaccine. Such antigenic components include but are not limited to those that provide protection against pathogens selected from the group consisting of bovine herpes virus (syn., infectious bovine rhinotracheitis), bovine respiratory syncitial virus, bovine viral diarrhea virus, parainfluenza virus types I, II, or III, Leptospira spp., Campylobacter spp., *Staphylococcus*

*aureus, Streptococcus agalactiae,* Mycoplasma spp., Klebsiella spp., Salmonella spp., rotavirus, coronavirus, rabies, *Pasteurella hemolytica, Pasteurella multocida,* Clostridia spp., *Tetanus toxoid, E. coli,* Cryptosporidium spp., Eimeria spp., Trichomonas spp., and other eukaryotic parasites, among others.

In a non-limiting embodiment, the combination vaccine of the present invention comprises a combination of two or more components selected from the group consisting of an immunologically effective amount of a protein or polypeptide of the present invention, an immunologically effective amount of a polynucleotide molecule of the present invention, and an immunologically effective amount of modified Neospora cells of the present invention. In a preferred embodiment, the combination vaccine of the present invention comprises a combination of two or more components selected from the group consisting of *N. caninum* GRA1, GRA2, SAG1, MIC1, and MAG1 proteins, polynucleotide molecules encoding any of the *N. caninum* GRA1, GRA2, SAG1, MIC1, and MAG1 proteins, and modified live Neospora cells exhibiting any of the GRA1$^-$, GRA2$^-$, SAG1$^-$, MIC1$^-$, and MAG1$^-$ phenotypes.

The vaccines of the present invention can further comprise one or more additional immunomodulatory components including, e.g., an adjuvant or cytokine, as described below.

The present invention further provides a method of preparing a vaccine against neosporosis, comprising combining an immunologically effective amount of a *N. caninum* protein or polypeptide, or polynucleotide molecule, or modified Neospora cells of the present invention, with a veterinarily acceptable carrier, in a form suitable for administration to a mammal. In a preferred embodiment, the protein is a *N. caninum* protein selected from the group consisting of GRA1, GRA2, SAG1, MIC1 and MAG1; the polynucleotide molecule preferably comprises a nucleotide sequence encoding a *N. caninum* protein selected from the group consisting of GRA1, GRA2, SAG1, MIC1 and MAG1; and the modified Neospora cells preferably are live cells that exhibit a phenotype selected from the group consisting of GRA1$^-$, GRA2$^-$, SAG1$^-$, MIC1$^-$, and MAG1$^-$.

A vaccine comprising modified live Neospora cells of the present invention can be prepared using an aliquot of culture fluid containing said Neospora cells, either free in the medium or residing in mammalian host cells, or both, and can be administered directly or in concentrated form to the mammal. Alternatively, modified live Neospora cells can be combined with a veterinarily acceptable carrier, with or without an immunomodulatory agent, selected from those known in the art and appropriate to the chosen route of administration, preferably where at least some degree of viability of the modified live Neospora cells in the vaccine composition is maintained. Modified Neospora cells that can be used in the vaccine of the present invention are preferably tachyzoites, but can alternatively be bradyzoites or oocysts, or some combination thereof.

Vaccine compositions of the present invention can be formulated following accepted convention to include veterinarily acceptable carriers, such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Suitable other vaccine vehicles and additives, including those that are particularly useful in formulating modified live vaccines, are known or will be apparent to those skilled in the art,. See, e.g., Remington's *Pharmaceutical Science,* 18th ed., 1990, Mack Publishing, which is incorporated herein by reference.

The vaccine of the present invention can further comprise one or more additional immunomodulatory components such as, e.g., an adjuvant or cytokine, among others. Non-limiting examples of adjuvants that can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block co polymer (CytRx, Atlanta GA), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant. Specific non-limiting examples of oil-in-water emulsions useful in the vaccine of the invention include modified SEAM62 and SEAM ½ formulations. Modified SEAM62 is an oil-in-water emulsion containing 5% (v/v) squalene (Sigma), 1% (v/v) SPAN® 85 detergent (ICI Surfactants), 0.7% (v/v) TWEEN® detergent (ICI Surfactants), 2.5% (v/v) ethanol, 200 µg/ml Quil A, 100 µg/ml cholesterol, and 0.5% (v/v) lecithin. Modified SEAM ½ is an oil-in-water emulsion comprising 5% (v/v) squalene, 1% (v/v) SPAN® 85 detergent, 0.7% (v/v) Tween 80 detergent, 2.5% (v/v) ethanol, 100 µg/ml Quil A, and 50 µg/ml cholesterol. Other immunomodulatory agents that can be included in the vaccine include, e.g., one or more interleukins, interferons, or other known cytokines. Where the vaccine comprises modified live Neospora cells, the adjuvant is preferably selected based on the ability of the resulting vaccine formulation to maintain at least some degree of viability of the modified live Neospora cells.

Where the vaccine composition comprises a polynucleotide molecule, the polynucleotide molecule can either be DNA or RNA, although DNA is preferred, and is preferably administered to a mammal to be protected against neosporosis in an expression vector construct, such as a recombinant plasmid or viral vector, as known in the art. Examples of recombinant viral vectors include recombinant adenovirus vectors and recombinant retrovirus vectors. However, a preferred vaccine formulation comprises a non-viral DNA vector, most preferably a DNA plasmid-based vector. The polynucleotide molecule may be associated with lipids to form, e.g., DNA-lipid complexes, such as liposomes or cochleates. See, e.g., International Patent Publication WO 93/24640.

An expression vector useful as a vaccinal agent in a DNA vaccine preferably comprises a nucleotide sequence encoding one or more antigenic Neospora proteins, or a substantial portion of such a nucleotide sequence, in operative association with one or more transcriptional regulatory elements required for expression of the Neospora coding sequence in a eukaryotic cell, such as, e.g., a promoter sequence, as known in the art. In a preferred embodiment, the regulatory element is a strong viral promoter such as, e.g., a viral promoter from RSV or CMV. Such an expression vector also preferably includes a bacterial origin of replication and a prokaryotic selectable marker gene for cloning purposes, and a polyadenylation sequence to ensure appropriate termination of the expressed mRNA. A signal sequence may also be included to direct cellular secretion of the expressed protein.

The requirements for expression vectors useful as vaccinal agents in DNA vaccines are further described in U.S. Pat.

No. 5,703,055, U.S. Pat. No. 5,580,859, U.S. Pat. No. 5,589,466, International Patent Publication WO 98/35562, and in various scientific publications, including Ramsay et al., 1997, Immunol. Cell Biol. 75:360–363; Davis, 1997, Cur. Opinion Biotech. 8:635–640; Maniackan et al., 1997, Critical Rev. Immunol. 17:139–154; Robinson, 1997, Vaccine 15(8):785–787; Lai and Bennett, 1998, Critical Rev. Immunol. 18:449–484; and Vogel and Sarver, 1995, Clin. Microbiol. Rev. 8(3):406–410, among others.

Where the vaccine composition comprises modified live Neospora cells, the vaccine can be stored cold or frozen. Where the vaccine composition instead comprises a protein, polypeptide, polynucleotide molecule, or inactivated modified Neospora cells of the present invention, the vaccine may be stored frozen, or in lyophilized form to be rehydrated prior to administration using an appropriate diluent.

The vaccine of the present invention can optionally be formulated for sustained release of the antigen. Examples of such sustained release formulations include antigen in combination with composites of biocompatible polymers, such as, e.g., poly(lactic acid), poly(lactic-co-glycolic acid), methylcellulose, hyaluronic acid, collagen and the like. The structure, selection and use of degradable polymers in drug delivery vehicles have been reviewed in several publications, including A. Domb et al., 1992, Polymers for Advanced Technologies 3: 279–292, which is incorporated herein by reference. Additional guidance in selecting and using polymers in pharmaceutical formulations can be found in the text by M. Chasin and R. Langer (eds), 1990, "Biodegradable Polymers as Drug Delivery Systems" in: *Drugs and the Pharmaceutical Sciences*, Vol. 45, M. Dekker, N.Y., which is also incorporated herein by reference. Alternatively, or additionally, the antigen can be microencapsulated to improve administration and efficacy. Methods for microencapsulating antigens are well-known in the art, and include techniques described, e.g., in U.S. Pat. No. 3,137,631; U.S. Pat. No. 3,959,457; U.S. Pat. No. 4,205,060; U.S. Pat. NO. 4,606,940; U.S. Pat. No. 4,744,933; U.S. Pat. No. 5,132,117; and International Patent Publication WO 95/28227, all of which are incorporated herein by reference.

Liposomes can also be used to provide for the sustained release of antigen. Details concerning how to make and use liposomal formulations can be found in, among other places, U.S. Pat. No. 4,016,100; U.S. Pat. No. 4,452,747; U.S. Pat. No. 4,921,706; U.S. Pat. No. 4,927,637; U.S. Pat. No. 4,944,948; U.S. Pat. No. 5,008,050; and U.S. Pat. No. 5,009,956, all of which are incorporated herein by reference.

The present invention further provides a method of vaccinating a mammal against neosporosis, comprising administering to the mammal an immunologically effective amount of a vaccine of the present invention. The vaccine is preferably administered parenterally, e.g., either by subcutaneous or intramuscular injection. However, the vaccine can alternatively be administered by intraperitoneal or intravenous injection, or by other routes, including, e.g., orally, intranasally, rectally, vaginally, intra-ocularly, or by a combination of routes, and also by delayed release devices as known in the art. The skilled artisan will be able to determine the most optimal route of vaccine administration, and will also recognize acceptable formulations for the vaccine composition according to the chosen route of administration.

An effective dosage can be determined by conventional means, starting with a low dose of antigen, and then increasing the dosage while monitoring the effects. Numerous factors may be taken into consideration when determining an optimal dose per animal. Primary among these is the species, size, age and general condition of the animal, the presence of other drugs in the animal, the virulence of a particular species or strain of Neospora against which the animal is being vaccinated, and the like. The actual dosage is preferably chosen after consideration of the results from other animal studies.

The dose amount of a Neospora protein or polypeptide of the present invention in a vaccine of the present invention preferably ranges from about 10 µg to about 10 mg, more preferably from about 50 µg to about 1 mg, and most preferably from about 100 µg to about 0.5 mg. The dose amount of a Neospora polynucleotide molecule of the present invention in a vaccine of the present invention preferably ranges from about 50 µg to about 1 mg. The dose amount of modified Neospora cells of the present invention in a vaccine of the present invention preferably ranges from about $1\times10^3$ to about $1\times10^1$ cells/ml, and more preferably from about $1\times10^5$ to about $1\times10^7$ cells/ml. A suitable dosage size ranges from about 0.5 ml to about 10 ml, and more preferably from about 1 ml to about 5 ml. The dose amounts of these antigens are also applicable to combination vaccines of the present invention. Where the second component of the combination vaccine is an antigen other than a Neospora protein, polypeptide, polynucleotide or modified cell of the present invention, the dose amount of the second component for use in the combination vaccine can be determined from prior vaccine applications of that second component, as known in the art.

The vaccine of the present invention is useful to protect mammals against neosporosis. As used herein, the term "mammal" refers to any mammalian species that can be protected against neosporosis using the vaccine of the invention, including dogs, cows, goats, sheep and horses, among others. The vaccine of the invention can be administered at any time during the life of a particular animal depending upon several factors including, e.g., the timing of an outbreak of neosporosis among other animals, etc. The vaccine can be administered to animals of weaning age or younger, or to more mature animals, e.g., as a pre-breeding vaccine to protect against Neospora-related congenital disease or abortion. Effective protection may require only a primary vaccination, or one or more booster vaccinations may also be needed. One method of detecting whether adequate immune protection has been achieved is to determine seroconversion and antibody titer in the animal after vaccination. The timing of vaccination and the number of boosters, if any, will preferably be determined by a veterinarian based on analysis of all relevant factors, some of which are described above.

The present invention further provides a kit for vaccinating a mammal against neosporosis, comprising a container having an immunologically effective amount of a polypeptide, polynucleotide molecule, or modified Neospora cells of the present invention, or a combination thereof. The kit can optionally comprise a second container having a veterinarily acceptable carrier or diluent. In a preferred embodiment, the polypeptide is selected from the group consisting of GRA1, GRA2, SAG1, MIC1 and MAG1 proteins of *N. caninum*; the polynucleotide molecule preferably has a nucleotide sequence that encodes a *N. caninum* protein selected from the group consisting of GRA1, GRA2, SAG1, MIC1, and MAG1; and the modified Neospora cells preferably are live cells that express a $GRA1^-$, $GRA2^-$, $SAG1^-$, $MIC1^-$ or $MAG1^-$ phenotype.

The following example is illustrative only, and is not intended to limit the scope of the present invention.

5. EXAMPLE: ISOLATION OF N. CANINUM cDNA AND GENE SEQUENCES

5.1. Identification of λ Clones Containing GRA1, GRA2, SAG1 and MIC1 cDNAs

A cDNA library of *N. caninum* tachyzoites was obtained from Dr. T. Baszler, Washington State University, Pullman, Wash. Briefly, this library was constructed using RNA purified from *N. caninum* NC-1 tachyzoites. cDNAs were cloned in bacteriophage λZAPExpress (Stratagene, La Jolla, Calif.) following addition of EcoRI and Xhol linkers to the cDNA ends. The library was estimated to contain ~99% recombinants based on the formation of white plaques when aliquots of the library were mixed with *E. coli* XL-1 Blue MRA(P2) (Stratagene) and plated on NZY agar plates containing IPTG.

The recombinant insert DNA sequences of individual putative λZAPExpress clones identified as described above were subjected to PCR analyses essentially as described by Krishnan etal., 1991, Nucl. Acids. Res. 19:6177–6182; and Krishnan etal., 1993, Meth. Enzym. 218:258–279, which publications are incorporated herein by reference. Thus, plugs of agar containing well separated bacteriophage λ plaques were recovered using a sterile Pasteur pipette and immersed in 100 μl of sterile water for at least 1 hr. About 10 μl of the diffused bacteriophage λ particles was used to perform PCR in a total volume of 100 μl containing: (1) 100 ng each of λDASH-T3 and λDASH-T7 oligonucleotide primers specific to the λ bacteriophage vectors, i.e., λZAPExpress, with specificity to the sequences adjacent to the cloning sites (i.e., EcoRI and Xhol), and oriented in a 5' to 3' direction towards the insert DNA sequences; (2) 200 μM dNTPs; (3) PCR buffer (Life Technologies, Inc., Gaithersburg, Md.); and (4) ~1 unit of Taq DNA polymerase buffer (Life Technologies, Inc.). The sequence of λDASH-T3 is 5'-MTTAACCCTCACTAAAGGG (SEQ ID NO:14). The sequence of λDASH-T7 is 5'-GTMTACGACTCAC TATAGGGC (SEQ ID NO:15). Thermal cycling conditions were as follows: 94° C., 5 min, 1 cycle; 94° C., 1 min, 55° C., 1 min, 72° C, 1 min, 30 cycles; 72° C, 7 min, 1 cycle. An aliquot of the reaction mixture (typically 10 μl) was examined by standard agarose gel electrophoresis, ethidium bromide staining and visualization under UV illumination. The PCR mixtures were purified by ion exchange column chromatography using a PCR purification system (Qiagen), and sequenced directly using the λDASH-T3 and λDASH-T7 primers employing fluorescent labeling and the Sanger dideoxy chain termination DNA sequencing technology. Sequences were analyzed for homology to other known sequences by comparison to DNA sequence databases at the National Center for Biotechnology Information, Bethesda, Md., 20894, USA. Four sequences, with homology to T gondii GRAL, GRA2, SAGi and MIC1 genes, respectively, were identified.

5 5.2. Identification of Complete ORFs for *N. caninum* GRA1, GRA2, SAG1 and MIC1 cDNAs The above-described bacteriophage λZAPExpress particles identified as containing *N. caninum* sequences having homology to *T. gondii* GRA1, GRA2, SAG1, and MIC1 genes, respectively, were subjected to an in vivo excision protocol following manufacturer's instructions (Stratagene) to recover the insert sequences in plasmid pBluescript. Briefly, the phage particles were allowed to infect *E. coli* XL-1 Blue MRF co-infected with ExAssist helper phage (Stratagene). Following this treatment, the supernatant was collected and used to mix with *E. coli* XLOLR cells (Stratagene). Aliquots of the cell suspension were then plated on media containing kanamycin (~50 μg/ml), and kanamycin-resistant colonies were examined for plasmid profile. Plasmid DNA was purified and the recombinant portion sequenced using the Sanger dideoxy chain termination DNA sequencing technology. DNA sequences obtained were analyzed by DNASTAR (DNASTAR, Inc., Madison, Wis.) to identify ORFs and other features. The sequences were also analyzed using BLAST algorithms (National Center for Biotechnology Information) for homology comparison to DNA sequences in the public databases.

The recombinant plasmid clone identified as containing the complete *N. caninum* GRA1 ORF was designated as pRC77 (ATCC 209685). The total length of the cDNA insert sequence in pRC77 is 1,265 bp, with the GRA1 ORF extending from nts 205–777 (SEQ ID NO:1). The deduced amino acid sequence of the *N. caninum* GRA1 protein is presented as SEQ ID NO:2.

The nucleotide sequence of the *N. caninum* GRA1 ORF has ~55% similarity to the nucleotide sequence of the *T. gondii* GRA1 ORF. The deduced amino acid sequence of the *N. caninum* GRA1 protein has ~51% similarity to the deduced amino acid sequence of the *T. gondii* GRA1 protein.

The recombinant plasmid clone identified as containing the complete *N. caninum* GRA2 ORF was designated as pRC5 (ATCC 209686). The total length of the cDNA insert sequence in pRC5 is 1,031 bp, with the GRA2 ORF extending from nts 25–660 (SEQ ID NO:4). The deduced amino acid sequence of the *N. caninum* GRA2 protein is presented as SEQ ID NO:5. The nucleotide sequence of the *N. caninum* GRA2 ORF has ~37% similarity to the nucleotide sequence of the *T. gondii* GRA2 ORF. The deduced amino acid sequence of the *N. caninum* GRA2 protein has ~26% similarity to the deduced amino acid sequence of the *T. gondii* GRA2 protein.

The recombinant plasmid clone identified as containing the complete *N. caninum* SAG1 ORF was designated as pRC102 (ATCC 209687). The total length of the cDNA insert sequence in pRC102 is 1,263 bp, with the SAG1 ORF extending from nts 130–1,089 (SEQ ID NO:6). The deduced amino acid sequence of the *N. caninum* SAG1 protein is presented as SEQ ID NO:7. The nucleotide sequence of the *N. caninum* SAG1 ORF has ~58% similarity to the nucleotide sequence of the *T. gondii* SAG1 ORF. The deduced amino acid sequence of the *N. caninum* SAG1 protein has ~49% similarity to the deduced amino acid sequence of the *T. gondii* SAG1 protein.

The recombinant plasmid clone identified as containing the complete *N. caninum* MIC1 ORF was designated as pRC340 (ATCC 209688). The total length of the cDNA insert sequence in pRC340 is 2,069 bp, with the MIC1 ORF extending from nts 138–1,520 (SEQ ID NO:8). The deduced amino acid sequence of the *N. caninum* MIC1 protein is presented as SEQ ID NO:9. The nucleotide sequence of the *N. caninum* MIC1 ORF has ~58% similarity to the nucleotide sequence of the *T. gondii* MIC1 ORF. The deduced amino acid sequence of the *N. caninum* MIC1 protein has ~47% similarity to the deduced amino acid sequence of the *T. gondii* MIC1 protein.

5.3. Identification Of The GRA1 Gene Sequence

A genomic DNA library of *N. caninum* strain NC-1 was constructed in bacteriophage λ-II vector (Stratagene) according to conventional techniques. cDNA sequences derived from pRC77 (ATCC 209685) were PCR amplified as follows, and the resulting PCR amplified DNA fragment was used as a probe to screen the N. caninum strain NC-1 genomic DNA library. Primers bd219 and bd220 specific to N. caninum GRA1 cDNA were used to amplify a 563 bp fragment corresponding to the ORF of N. caninum GRA1 cDNA (pRC77). bd219 is 5'-GCCGCGACTTCTTTT TCTCT (SEQ ID NO:16) and bd220 is 5'-CTCGATCGCC TCCTTTACTG (SEQ ID NO:17). The 563 bp fragment was purified by electrophoresis using SeaPlaque low melting agarose (LMA) (FMC Bioproducts). The band was excised from the gel and subsequently used in random prime labeling reactions to generate a probe in preparation for screening a Neospora genomic library. 2.5×10⁵ pfu from a N. caninum genomic library (λDASH Stratagene #845201) were plaque-lifted onto Hybond N+ nylon membrane (Amersham). Duplicate filters were screened using the 563 bp GRA1 cDNA fragment as a probe. Nine duplicate pfus were scored positive and subsequently cored in 1 ml SM buffer. Four of these clones (# 5–8) were carried forward to secondary screening. On secondary screening, 500–1000 pfu per clone were plaque-lifted onto duplicate filters. All four Gra1 clones were positive on secondary screening and were isolated as individual plaques.

A λ clone designated as Gra1#8 was identified by this procedure, and was used as a template for PCR amplification using primers bd256 and bd254. Primer bd256 is 5'-TGCTAGTACTGGCGAGTGAA (SEQ ID NO:18). Primer bd254 is 5'-CAGGTTTGCCACACATTTTT (SEQ ID NO:19). The PCR fragment obtained was subcloned into pGEM-T EASY vector (Promega, Madison, Wis.). The cloned fragment was sequenced employing fluorescent labelling and Sanger dideoxy chain termination sequencing technology. Sequence analysis revealed that the cloned fragment contained the GRAI gene. The GRA1 gene sequence (SEQ ID NO:3) contains an ORF from nt 605 to nt 855 and from nt 983 to nt 1304, which shares complete identity to the GRA1 cDNA sequence (SEQ ID NO:1) of pRC77 (ATCC 209685) from nt 205 to nt 777. However, the GRA1 gene sequence (SEQ ID NO:3) differs from the cDNA sequence (SEQ ID NO:1) at a single nucleotide position in the 3' untranslated region at nt 1728 of the GRA1 gene where a thymine resides, instead of a guanine at nt 1201 of pRC77. This difference may be due to a RFLP or a sequencing error in pRC77 because this nucleotide discrepancy was confirmed in 2 separate subclones from the GRA1#8 λ genomic clone. The GRA1 gene sequence (SEQ ID NO:3) further comprises an intron extending from nt 856 to nt 982. Furthermore, three promoter motifs have been identified within 150 bp 5' of the mRNA start site that are similar to those found in T. gondii GRA genes (Mercier et al., 1996, Mol. Microbiol. 21:421–428).

5.4. Identification Of The SAG1 Gene Sequence

Oligonucleotide primers specific to the SAG1 gene were synthesized based on the SAG1 ORF of the DNA sequence obtained from pRC102. The first primer, designated as NCSAG1 5', was 5'-ATGTTTCCTCCTCGGGCAGTG (SEQ ID NO:20); and the second primer, designated as NCSAG1 3', was 5'-TCACGCGACGCCAGCCGCTATCG (SEQ ID NO:21). It was later determined that primer NCSAG1 5', as presented above, was inadvertently designed to include an additional three nucleotides (CCT), and the presence of these three additional nucleotides was thus taken into account when determining the actual SAG1 gene sequence.

PCR was performed using primers NCSAG1 5' (SEQ ID NO:20) and NCSAG1 3' (SEQ ID NO:21) on N. caninum strain NC-1 genomic DNA as template. An ~1 kb amplified fragment was obtained, which was cloned in plasmid pCR2.1 and in pBlunt (Invitrogen, Carlsbad, Calif.) according to manufacturer's recommendations. Recombinant plasmids identified to contain the genomic SAG1 PCR fragment were sequenced employing fluorescent labeling and Sanger dideoxy chain termination sequencing technology using standard 'universal', 'reverse' and the following oligonucleotides: NCSAG1200: 5'-GCCCTGACAATTCGACCGCC (SEQ ID NO:22); NCSAG1500: 5'-CCCACMCATCC MGTCGTTC (SEQ ID NO:23); NCSAG1660: 5'-GT TTTGCACCATCCTTAGTG (SEQ ID NO:24); and NCSAG1320: 5'-GAGAGTTTGCTTTGCACCG (SEQ ID NO:25). The DNA sequences obtained were assembled using the DNAStar software package, and were found to be identical to the sequence of the SAG1 ORF deduced from pRC102. Thus, the genomic sequence of the SAG1 gene is identical to that obtained from cDNA sequencing.

5.5. Identification Of The MIC1 Gene Sequence

A. 2.2 kb DNA fragment was PCR amplified from N. caninum genomic DNA using oligonucleotides specific for the 5' and 3' ends of the MIC1 cDNA fragment (see sequence of pRC340). Thermal cycling conditions were as follows: 94° C., 1 min, 1 cycle; 94° C., 45 sec, 54° C., 45 sec, 72° C., 2 min, 29 cycles; 72° C., 5 min, 1 cycle. This ~2.2 kb fragment was cloned into pCR2.1 and into pZEROBLUNT (Invitrogen, Carlsbad, Calif.). Recombinant plasmids were identified by standard restriction analysis, and representative clones were sequenced using fluorescent labelling and Sanger dideoxy chain termination technology. Locations of exons and introns were identified by comparison to the MIC1 cDNA sequence from pRC340.

The total length of the MIC1 gene region is 2278 bp (SEQ ID NO:10), comprising an ORF from nt 1 to nt 73, nt 345 to nt 811, nt 1187 to nt 1265, and nt 1515 to nt 2278, with three intervening introns.

5.6. Identification Of The MAG1 Gene Sequence

BspDI, EcoRI and Hindlll Vectorette libraries (Genosys) were prepared according to manufacturer's protocols using genomic clone Gra1#8 as template DNA. Using the anti-sense primer bd234 specific for 5' GRA1 cDNA, and Vectorette primer II (ER-70), a ~2 kb fragment was amplified from the Hindill Vectorette library using Klentaq (AB Peptide Inc.) and PFU (Stratagene) polymerases. Primer bd234 is 5'-CCAGCCGAGTTCGTGTTCAGA (SEQ ID NO:26), and primer ER-70 is CMCGTGGATCCGATTCMGCTTC (SEQ ID NO:27). The product was run on a 1% LMA gel, excised, and used directly in a cloning reaction with pGEM-T EASY vector. Transformation into E. coli DH5α produced several white colonies. Notl restriction analysis of DNA from twenty different white clones indicated that 18 of 20 clones contained the appropriate sized insert. Subclone 2 was selected to be grown as stock and this plasmid was renamed bd245. The PCR product from the Vectorette 2 kb Gra1 promoter fragment was sequenced from both ends using nested primer bd218 and the Vectorette sequencing primer. The sequence of primer bd218 is 5'-AAAGCTCTTCGGCAGTTCAA (SEQ ID NO:28). The complete sequence of plasmid bd245 was generated by standard primer walking using Sanger fluorescent dideoxy chain termination sequencing technology.

Primer bd252 was used in combination with a variant of primer T7, and Gra1#8 DNA as template, in a PCR to map one end of clone Gra1#8. Primer bd252 is 5'-CCGCGCTACCACTTTCCA (SEQ ID NO:29). The T7 primer variant is 5'-GTAATACGACTCACTATA (SEQ ID NO:30). A ~2.5 kb fragment was amplified using primer bd252 and the T7 variant, which product was subcloned into pGEM-T EASY vector, and this plasmid was named bd282. Primer walking, using fluorescent labeling and Sanger dideoxy chain termination sequencing technology, was employed to complete the entire sequence of plasmid bd282.

Sequences from plasmids bd245 and bd282 were used to generate the contiguous sequence shown in SEQ ID NO:11, encoding the MAG1 gene which was identified using WU-BLAST2 (Washington University BLAST version 2). Results indicate that this sequence has homology to the *T. gondii* MAG1 gene (Accession No. U09029). Putative exon/intron boundaries were identified by intron splice site consensus sequences and alignment with the *T. gondii* MAG1 sequence, which suggested an mRNA transcript from nt 704 to nt 820 (exon 1), from nt 1301 to nt 1399 (exon 2), from nt 1510 to nt 1808 (exon 3), and from nt 1921 to nt 3297 (exon 4), with intervening introns. Based on these putative exon/intron boundaries, a proposed cDNA sequence is presented as SEQ ID NO:12, and an amino acid sequence deduced therefrom is provided as SEQ ID NO:13. Comparison of exon and intron boundaries between *T. gondii* and *N. caninum* indicate that exons 1–3 and introns 1–2 of the MAG1 gene are relatively positionally conserved between the two organisms. Intron 3 and exon 4 splice sites are unique to *N. caninum* MAG1. SEQ ID NO:11 also comprises a portion of the GRA1 gene sequence of GRA1, from nt 1 to nt 126, and the complete intervening putative bidirectional GRA1IMAG1 promoter region, from nt 127 to nt 703.

DNA from lambda Gra1#8 clone was digested with NotI to release insert DNA, which was subsequently extracted with phenol/chloroform, precipitated and resuspended in water. DNA from this preparation was ligated to purified NotI digested BS KS+ vector DNA (Stratagene), and thereafter transformed into *E. coli* DH5α cells. Clones were screened by PCR using primers specific for GRA1 and MAG1 genes, and further verified by NotI restriction digestion for the presence of the ~16 kb lambda GRA1#8 NotI insert. The primers used for PCR were GRA1 primers 219 (SEQ ID NO:16) and 220 (SEQ ID NO:17), and MAG1 primers 261 and 270. Primer 261 is 5'-CCGCAACGTGCTGTTCCTA (SEQ ID NO:31); and primer 270 is 5'-CATCAGAGAAACTGGAGT (SEQ ID NO:32). A positive plasmid clone containing the BS KS+ vector ligated to the NotI insert from lambda Gra1#8 was identified and named bd304 (ATCC 203413).

5.7. Identification Of The MAG1 And GRA1 Promoters of Neospora

5.7.1. Background On *T. gondii* GRA1 Promoter Elements

Functional mutational analysis of the *T. gondii* GRA1 promoter and sequence comparison to another well-defined *T. gondii* promoter (SAG1) identified a heptanucleotide motif (TGAGACG) which confers basal GRA1 promoter activity in an orientation-independent manner (Mercier et al., 1996, Mol. Micro. 21:421–428). Two additional heptanucleotide motifs in the GRA1 promoter confer additional transcriptional activity. The *T. gondii* GRA1 promoter is contained within the upstream, proximal region from −129 to −47 relative to the GRA1 transcription start site. Significant promoter elements in this *T. gondii* GRA1 region include 1 CAAT box, 1 heptanucleotide motif in direct orientation and 2 heptanucleotide motifs in an inverse orientation. Three additional heptanucleotide motifs were identified upstream (−349 to −204) of the *T. gondii* GRA1 promoter but do not confer significant increase to the −129 to −47 promoter element.

5.7.2. Neospora MAG1 -GRA1 Promoter Elements

Genomic sequence analysis of the complete MAG1-GRA1 region of *N. caninum* strain NC-1 indicates that the two genes are arranged in a head to head configuration. There is a 577 bp region between the putative translational start sites for the MAG1 and GRA1 genes (SEQ ID NO:11, from nt 127 to nt 703) that contains the putative MAG1IGRA1 bidirectional promoter. Sequence analysis of this 577 bp region identifies three inverted heptanucleotide motifs (CGTCTCA or CGTCTCT) as described for the *T. gondii* GRA1 promoter (Mercier et al., 1996, above). Two CAAT boxes flank these heptanucleotide motifs; one CAAT box is oriented toward the GRA1 gene and the second CAAT box is oriented toward the MAG1 gene. The Table below lists the promoter elements found in the *N. caninum* MAG1IGRA1 bidirectional promoter region.

TABLE

| promoter element | position to putative transcriptional start site defined by PRC77[a] |
|---|---|
| CAAT box | −133 to −130 |
| CAAT box (reverse)* | −49 to −52 |
| CGTCTCA** | −125 to −119 |
| CGTCTCA** | −106 to −100 |
| CGTCTCT** | −70 to −64 |

[a]Nucleotide positions are in reference to the putative transcription start site defined by the 5' end of the GRA1 cDNA (pRC77).
*This CAAT box is read from the complement strand and is oriented toward the MAG1 gene (65kDa).
**Inverted heptanucleotide promoter motifs, as defined by Mercier et al. 1996, above.

5.7.3. Construction Of Neospora GRA1 Promoter Construct

The functionality of the 577 bp putative MAG1 IGRA1 bidirectional promoter containing the two heptanucleotide motifs and two CAAT boxes was tested by engineering a plasmid containing the LacZ reporter gene downstream of this defined sequence and then transfecting this plasmid into NC-1 tachyzoites. A Bluescript plasmid, designated as GLS, containing the *T. gondii* GRA1 promoter driving LacZ expression and containing a *T. gondii* SAG1 3' end, was provided by Dr. David Sibley, Washington University School of Medicine, St. Louis, Mo., USA. Hindll/NsiI digestion of plasmid GLS removed the *T. gondii* GRA1 promoter fragment, and subsequent LMA purification was performed to generate a promoter-less LacZ reporter vector. Primers Hindlil-bd256 (5'-GGCCAAGCTTGCTAG TACTGGCGA; SEQ ID NO:33) and bd260-NsiI (5'-ATCCMTGCATCTTGCTGAATGCCTTAAAAG; SEQ ID NO:34) were used in an amplification reaction with lambda clone gra1#8 as template, and PFU and Klentaq polymerases, to generate an ~600 bp promoter fragment containing the 5' untranslated region from the Neospora GRA1 gene. This fragment was digested with Hindlil/NsiI, purified on LMA, and subsequently used in a ligation reaction with the above described promoter-less LacZ reporter vector to generate plasmid clone bd266. A PCR reaction with primers HindIll-bd256 and bd260-NsiI was performed with plasmid clone bd266 to verify insertion of the *N. caninum* GRA1 promoter.

N. caninum NC-1 tachyzoites ($1 \times 10^7$) were transfected by electroporation with 5 μg or 50 μg of uncut plasmid bd266 or plasmid GLS at 1.4V, 10 uF, in cytomix buffer as described by Howe et al., 1997, METHODS: A COMPANION TO METHODS IN ENZYMOLOGY 13:1–11. Electroporated NC-1 cells were allowed to infect MARC-145 monkey kidney cells in a T25 flask (80% confluency) for 3 days before harvesting for a β-galactosidase assay. Cells were harvested by removing 3 ml of media and using the remaining 1 ml of media to scrape cells from flask. Harvested cells were transferred to a microcentrifuge and spun. Supernatant was discarded, and the pelleted cells were resuspended in 100 μl of lysis buffer (Howe et al., 1997, above). Tubes were stored at −20° C. until the β-galactosidase assay was performed.

To conduct the β-galactosidase assay, tubes were thawed, mixed, incubated at 50° C. for 1 hr, and then spun in a microcentrifuge. Fifty μl of supernatant was used per sample. The β-galactosidase assay was performed as described by Howe et al.,1997, above. A standard curve was prepared using a strain of N. caninum that had been stably transfected with the plasmid GLS, as provided by Dr. David Sibley. Tachyzoites were harvested, counted, resuspended in lysis buffer at $10^4$ parasites/ml, and subsequently processed as above (i.e., incubated at 50° C. for 1 hr.). Twelve serial dilutions from this preparation were made in a range of from about 20,000 to about 10 parasites per well, and were used to create a standard curve in the β-galactosidase assay.

5.7.4. Results

Samples containing cell lysate from N. caninum strain NC-1 transfected with plasmid bd266 gave the highest β-galactosidase readings compared to samples containing cell lysate from N. caninum strain NC-1 transfected with plasmid GLS. Using the extracted value from the standard curve for bd266 (50 μg plasmid), the β-galactosidase reading was equivalent to 7013 parasites from the N. caninum cell line stably transformed with plasmid GLS described above. These experiments provide the first evidence that the N. caninum GRA1 promoter is functional, and that the promoter elements lie within the ~600bp genomic fragment defined by primers HindIII-bd256 and bd260-NsiI.

6. EXAMPLE: EXPRESSION AND IMMUNOREACTIVITY OF A RECOMBINANT N. CANINUM MIC1 PROTEIN

DNA sequences representing the MIC1 ORF were PCR-amplified and cloned into pQE50 (Qiagen), which is a recombinant system that facilitates inducible high level expression of the cloned sequence. The recombinant plasmid was designated as pQEmic1. Whole cell lysates from uninduced and induced E. coli cells containing pQEmic1 were examined by SDS-PAGE and Coomassie blue protein staining. A polypeptide with a molecular weight of ~57 kDa was identified in induced, but not in uninduced, E. coli cells carrying pQEmic1. The molecular weight of the MIC1 polypeptide as estimated from the deduced amino acid sequence of MIC1 (SEQ ID NO:9) is ~49 kDa.

Whole cell lysates of induced and uninduced E. coli carrying pQEmic1 were run on SDS-PAGE, and the proteins were transferred to PVF membranes (Novex) by standard procedures. The membranes were then blocked using 1% polyvinyl alcohol (PVA) in phosphate buffered saline (PBS). Following this, the membranes were rinsed three times in PBS containing 0.05% Tween-20 (PBST). The membranes were then incubated for about 1 hr either in a solution containing pooled polyclonal antisera from a naturally N. caninum-infected cattle herd (a gift from Dr. John Ellis, University of Technology, Sydney, Australia), or in a solution containing polyclonal antisera from rabbits experimentally infected with T. gondii (a gift from Dr. R. A. Cole, National Wildlife Health Center, Madison, Wis.). The membranes were then washed 3× with PBST, and reacted with goat anti-bovine or anti-rabbit IgG/alkaline phosphate conjugate (Kirkegaard and Perry Labs, Gaithersburg, Md.), as appropriate, diluted 1:500 according to manufacturer's recommendations. The membranes were washed in PBST again and bands were detected by incubating the membranes briefly in BCIP/NBT reagent ((Kirkegaard and Perry Labs), followed by rinsing in $dH_2O$. The recombinantly-expressed MIC1 protein was found to have specific reactivity to both N. caninum and T. gondii polyclonal antisera.

7. EXAMPLE: VACCINE FORMULATIONS

A vaccine against neosporosis is formulated by combining a N. caninum protein of the present invention, such as, e.g., SAG1, at about 100 μg/ml with an equal volume of modified SEAM62 adjuvant, followed by gentle mixing, and storage at 4° C., for primary and boost immunizations. A primary dose of about 2 ml (total 100 μg) is administered subcutaneously to cattle, followed by a booster vaccination three weeks later. After two weeks following boost vaccination, cattle can be bred. Vaccines comprising a GRA1, GRA2, MIC1 or MAG1 protein of the present invention, or combinations thereof, can also be formulated and administered in this manner.

Deposit Of Biological Materials

The following biological materials were deposited with the American Type Culture Collection (ATCC) at 12301 Parklawn Drive, Rockville, Md., 20852, USA, on Mar. 19, 1998, and were assigned the following accession numbers:

| Plasmid | ATCC Accession No. |
| --- | --- |
| pRC77 | 209685 |
| pRC5 | 209686 |
| pRC102 | 209687 |
| pRC340 | 209688 |

The following additional biological material was deposited with the ATCC, at 10801 University Blvd, Manassas, Va., 20110, USA, on Nov. 9, 1998, and was assigned the following accession number:

| Plasmid | ATCC Accession No. |
| --- | --- |
| bd304 | 203413 |

All patents, patent applications, and publications cited above are incorporated herein by reference in their entirety.

The present invention is not limited in scope by the specific embodiments described, which are intended as single illustrations of individual aspects of the invention. Functionally equivalent compositions and methods are within the scope of the invention. Indeed, various modifications of the invention, in addition to those shown and described herein, will become apparent to those skilled in the art from the foregoing description. Such modifications are intended to fall within the scope of the appended claims.

What is claimed is:

1. An isolated polynucleotide molecule comprising a nucleotide sequence encoding a protein comprising the amino acid sequence of SEQ ID NO:2.

2. An isolated polynucleotide molecule comprising a nucleotide sequence selected from the group consisting of the nucleotide sequence of SEQ ID NO:1 from nt 205 to nt 777, the nucleotide sequence of SEQ ID NO:3 from nt 605 to nt 1304, and the nucleotide sequence of the GRA1-encoding ORF of plasmid pRC77 (ATCC209685).

3. An isolated polynucleotide molecule comprising a nucleotide sequence that hybridizes under conditions of 0.5 M NaHPO$_4$, 7% sodium dodecyl sulfate (SDS), 1mM EDTA at 65° C., and washing in 0.2 ×SSC/0.1% SDS at 42° C., to the compliment of a polynucleotide molecule having a nucleotide sequence that encodes the amino acid sequence of SEQ ID NO:2, wherein the isolated polynucleotide molecule can detect the presence of a Neospora-specific polynucleotide in a fluid or tissue sample from a Neospora-infected animal; provided that the isolated polynucleotide molecule does not encode a polypeptide having more than 90% amino acid sequence identity to a native GRA polypeptide from *Toxoplasma gondii*.

4. The polynucleotide molecule of claim 3, comprising a nucleotide sequence that hybridizes under conditions of 0.5 M NaHPO$_4$, 7% SDS, 1 mM EDTA at 65° C., and washing in 0.1×SSC/0.1% SDS at 68° C., to the complement of a polynucleotide molecule having a nucleotide sequence that encodes the amino acid sequence of SEQ ID NO:2.

5. The polynucleotide molecule of claim 3, comprising a nucleotide sequence that hybridizes under conditions of 0.5 M NaHPO$_4$, 7% SDS, 1 mM EDTA at 65° C., and washing in 0.1×SSC/0.1% SDS at 68° C. to the complement of a polynucleotide molecule consisting of a nucleotide sequence selected from the group consisting of the nucleotide sequence of SEQ ID NO:1 from nt 205 to nt 777, and the nucleotide sequence of SEQ ID NO:3 from nt 605 to nt 1304.

6. The isolated polynucleotide molecule of claim 3, which does not encode a polypeptide having more 80% amino acid sequence identity to a native GRA polypeptide from *Toxoplasma gondii*.

7. An isolated polynucleotide molecule comprising a nucleotide sequence selected from the group consisting of SEQ ID NO:1 from nt 1 to nt 204; SEQ ID NO:1 from nt 778 to nt 1265; SEQ ID NO:3 from nt 1 to nt 604; SEQ ID NO:3 from nt 605 to nt 855; SEQ ID NO:3 from nt 856 to nt 982; SEQ ID NO:3 from nt 983 to nt 1304; and SEQ ID NO:3 from nt 1305 to nt 1774.

8. A recombinant vector comprising a polynucleotide molecule comprising a nucleotide sequence encoding a protein comprising the amino acid sequence of SEQ ID NO:2.

9. The recombinant vector of claim 8, wherein the nucleotide sequence of the polynucleotide molecule is selected from the group consisting of the nucleotide sequence of SEQ ID NO:1 from nt 205 to nt 777, the nucleotide sequence of SEQ ID NO:3 from nt 605 to nt 1304, and the nucleotide sequence of the GRA1-encoding ORF of plasmid pRC77 (ATCC 209685).

10. The recombinant vector of claim 9 which is plasmid pRC77 (ATCC 209685).

11. A recombinant vector comprising a polynucleotide molecule comprising a nucleotide sequence that hybridizes under conditions of 0.5 M NaHPO$_4$, 7% sodium dodecyl sulfate (SDS), 1mM EBTA at 65° C., and washing in 0.2 ×SSC/0.1% SDS at 42° C., to the compliment of a polynucleotide molecule having a nucleotide sequence that encodes the amino acid sequence of SEQ ID NO:2, wherein the polynucleotide molecule can detect the presence of a Neospora-specific polynucleotide in a fluid or tissue sample from a Neospora-infected animal; provided that the polynucleotide molecule does not encode a polypeptide having more than 90% amino acid sequence identity to a native GRA polypeptide from *Toxoplasma gondii*.

12. A host cell into which a polynucleotide molecule comprising a nucleotide sequence encoding a protein comprising the amino acid sequence of SEQ ID NO:2, or a recombinant vector comprising said polynucleotide molecule, has been introduced.

13. A host cell into which a polynucleotide molecule, or a recombinant vector comprising said polynucleotide molecule, has been introduced, said polynucleotide molecule comprising a nucleotide sequence that hybridizes under conditions of 0.5 M NaHPO$_4$, 7% SDS, 1 mM EDTA at 65° C., and washing in 0.1 ×SSC/0.1 % SDS at 68° C. to the complement of a polynucleotide molecule consisting of a nucleotide sequence selected from the group consisting of the nucleotide sequence of SEQ ID NO:1 from nt 205 to nt 777, and the nucleotide sequence of SEQ ID NO:3 from nt 605 to nt 1 304, wherein the isolated polynucleotide molecule can detect the presence of a Neospora-specific polynucleotide in a fluid or tissue sample from a Neospora-infected animal, provided that the polynucleotide molecule does not encode a polypeptide having more than 90% amino acid sequence identity to a native GRA polypeptide from *Toxoplasma gondii*.

14. A method of preparing a polypeptide comprising the amino acid sequence of SEQ ID NO:2, comprising culturing a host cell into which a polynucleotide molecule comprising a nucleotide sequence encoding a protein comprising the amino acid sequence of SEQ ID NO:2, or a recombinant vector comprising said polynucleotide molecule, has been introduced, which polynucleotide molecule is in operative association with one or more regulatory elements, under conditions conducive to the expression of the polypeptide, and recovering the expressed polypeptide from the cell culture.

* * * * *